United States Patent
Xu et al.

(10) Patent No.: US 11,584,745 B2
(45) Date of Patent: Feb. 21, 2023

(54) AROMATIC HETEROCYCLIC COMPOUND, INTERMEDIATE THEREOF, PREPARATION METHOD THEREFOR, AND PHARMACEUTICAL COMPOSITION AND USE THEREOF

(71) Applicant: SHANGHAI YINGLI PHARMACEUTICAL CO., LTD, Shanghai (CN)

(72) Inventors: Zusheng Xu, Shanghai (CN); Yangtong Lou, Shanghai (CN); Li Chen, Shanghai (CN); Kun Zeng, Shanghai (CN); Qingrui Sun, Shanghai (CN); Xiaoli Lei, Shanghai (CN)

(73) Assignee: SHANGHAI YINGLI PHARMACEUTICAL CO., LTD, Shanghai (CN)

( * ) Notice: Subject to any disclaimer, the term of this patent is extended or adjusted under 35 U.S.C. 154(b) by 343 days.

(21) Appl. No.: 16/964,531

(22) PCT Filed: Dec. 28, 2018

(86) PCT No.: PCT/CN2018/124666
§ 371 (c)(1),
(2) Date: Jul. 23, 2020

(87) PCT Pub. No.: WO2019/144764
PCT Pub. Date: Aug. 1, 2019

(65) Prior Publication Data
US 2021/0032241 A1 Feb. 4, 2021

(30) Foreign Application Priority Data
Jan. 24, 2018 (CN) .................. 201810068775.0

(51) Int. Cl.
*C07D 471/04* (2006.01)
(52) U.S. Cl.
CPC ................... *C07D 471/04* (2013.01)
(58) Field of Classification Search
CPC .................................................. C07D 471/04

USPC ......................................................... 514/300
See application file for complete search history.

(56) References Cited

FOREIGN PATENT DOCUMENTS

| | | | |
|---|---|---|---|
| CN | 101875674 | * | 11/2010 |
| CN | 110066276 A | | 7/2019 |
| WO | 02094833 A1 | | 11/2002 |
| WO | 2004013135 A1 | | 2/2004 |
| WO | 2004048383 A1 | | 6/2004 |
| WO | 2009022171 A1 | | 2/2009 |
| WO | 2009133070 A1 | | 11/2009 |
| WO | 2012002680 A2 | | 1/2012 |
| WO | 2016133838 A1 | | 8/2016 |

OTHER PUBLICATIONS

International Search Report dated Apr. 3, 2019 issued in International Application No. PCT/CN2018/124666, 8 pages.
First Office Action dated Dec. 18, 2019 issued in Chinese application No. 201810068775.0, 11 pages.
Written Opinion dated Apr. 3, 2019 issued in International Application No. PCT/CN2018/124666, 12 pages.

* cited by examiner

*Primary Examiner* — Niloofar Rahmani
(74) *Attorney, Agent, or Firm* — Foley & Lardner LLP

(57) ABSTRACT

Disclosed are an aromatic heterocyclic compound, an intermediate thereof, a preparation method therefor, and a pharmaceutical composition and use thereof. The aromatic heterocyclic compound of the present invention is a new ALK5 inhibitor, and is used for treating and/or preventing various ALK5-mediated diseases.

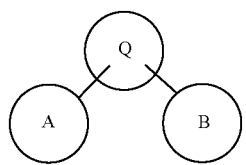

16 Claims, No Drawings

AROMATIC HETEROCYCLIC COMPOUND, INTERMEDIATE THEREOF, PREPARATION METHOD THEREFOR, AND PHARMACEUTICAL COMPOSITION AND USE THEREOF

CROSS-REFERENCE TO RELATED APPLICATIONS

The present application is a 371 of PCT/CN2018/124666, filed Dec. 28, 2018, which is based upon and claims the priority to Chinese patent application CN201810068775.0, filed on Jan. 24, 2018, both of which are hereby incorporated by reference in their entireties.

TECHNICAL FIELD

The present invention relates to an aromatic heterocyclic compound, intermediate thereof, preparation method therefor, and pharmaceutical composition and use thereof.

BACKGROUND

Transforming growth factor-β (TGF-β) is a multifunctional cytokine that participates in the regulation of cell proliferation, differentiation and apoptosis through complex receptor signaling pathways on the cell surface in manners of autocrine, paracrine and endocrin. TGF-β and activins, inhibitors, bone morphogenetic proteins, Mullerian-inhibiting substance and other related proteins belong to the transforming growth factor β superfamily (TGF-β superfamily, TGF-βs).

TGF-β has three main cell receptors: type I, type II and type III receptors. Type I and type II receptors are transmembrane serine/threonine kinases, both of which transmit information at the same time, type III receptors do not transmit information, the function of which is mainly to transmit TGF-β to type II receptors, so as to indirectly affect signal transduction through providing ligands for the receptor II.

The signal transduction pathway of TGF-β is mainly the TGF-β-Smad signaling pathway. The Smad protein family is an intracellular signal transduction protein discovered in recent years. It is known that there are 8 kinds of Smad protein molecules in the human body. After activating TGF-β in the form of an inactive protein complex, TGF-β interacts with type II receptor (TGFβR II) and type I receptor (TGFβR I, also known as ALK5 (activin-like kinase 5)) on the cell surface to form a double dimer receptor complex. Type II receptor phosphorylates and activates type I receptor, and then the Smad protein molecule (Smad2/3) is phosphorylated by type I receptor to which it is attached and releases into the cytoplasm, and forms a complex with the Smad4 protein which then transfers to the nucleus, thereby combining different transcription factors and transcription co-activators or transcription co-inhibitors to regulate the transcription of TGF-β target genes and produce biological effects. The TGF-β-Smad signaling pathway has important regulatory effects on cell proliferation, differentiation, apoptosis, attachment, migration, synthesis of extracellular matrix, wound repair, immune function and so on (Nature 2003, 425, 577). Studies have shown that abnormal TGF-β signaling is associated with many diseases, such as cancer, renal fibrosis, liver fibrosis, lung fibrosis, viral infections, chronic nephritis, acute nephritis, diabetic nephropathy, osteoporosis, arthritis, wound healing, ulcers, corneal trauma, cardiac valve stenosis, congestive cardiac necrosis, neurological impairment, Alzheimer's syndrome, peritoneal or subcutaneous adhesions, arteriosclerosis tumor, metastasis growth and so on. An important node TGFβR I (ALK5) in the TGF-β signaling pathway is an ideal target for the treatment of these diseases, by inhibiting ALK5 phosphorylation of its downstream signal Smad2 or Smad3, blocking or partially blocking the propagation of TGF-β signal into the cell, thereby correcting the abnormal TGF-β signaling, which can treat and prevent various ALK5-mediated diseases (Nat Rev Drug Discov. 2012 October, 11(10): 790-811; Pharmacology & Therapeutics 147 (2015) 22-31).

The prior art has disclosed some compounds as ALK5 inhibitors, for example: WO2012002680, WO2009022171, WO2009133070, WO2004048383, WO2004013135, WO2002094833 and so on.

The inventors have discovered through research that a class of aromatic heterocyclic compounds can be used as ALK5 inhibitors and are useful for treating and/or preventing various diseases mediated by ALK5.

Content of the Present Invention

The present invention provides an aromatic heterocyclic compound, an intermediate, a preparation method, a pharmaceutical composition and a use thereof. The aromatic heterocyclic compound of the present invention is a novel ALK5 inhibitor, which is used for treating and/or preventing various ALK5-mediated diseases.

The present invention provides an aromatic heterocyclic compound represented by the general formula I or a pharmaceutically acceptable salt thereof:

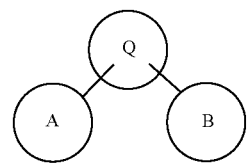

I wherein,

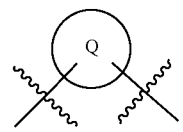

is

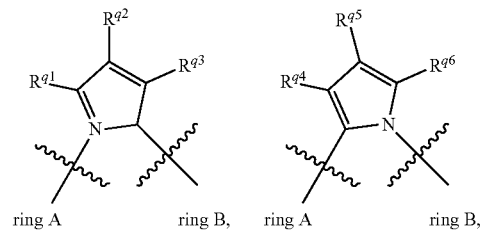

-continued

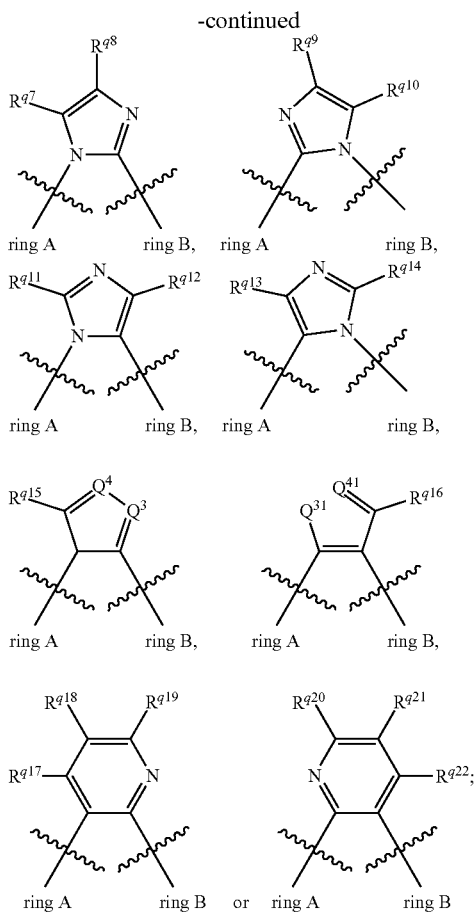

ring A　ring B,　ring A　ring B, ring A　ring B,　ring A　ring B, ring A　ring B,　ring A　ring B, ring A　ring B　or　ring A　ring B;

in ring Q, $R^{q1}$, $R^{q2}$, $R^{q3}$, $R^{q4}$, $R^{q5}$, $R^{q6}$, $R^{q7}$, $R^{q8}$, $R^{q9}$, $R^{q10}$, $R^{q11}$, $R^{q12}$, $R^{q13}$, $R^{q14}$, $R^{q15}$, $R^{q16}$, $R^{q17}$, $R^{q18}$, $R^{q19}$, $R^{q20}$, $R^{q21}$ and $R^{q22}$ are each independently hydrogen, deuterium, halogen, sulfonic acid group, substituted or unsubstituted $C_{1-6}$ alkyl, substituted or unsubstituted $C_{2-8}$ alkenyl, substituted or unsubstituted $C_{2-8}$ alkynyl, substituted or unsubstituted $C_{3-10}$ cycloalkyl, substituted or unsubstituted $C_{2-8}$ heterocycloalkyl, substituted or unsubstituted $C_{6-20}$ aryl, substituted or unsubstituted $C_{2-10}$ heteroaryl, cyano, $-OR^{61}$, $-SR^{62}$, $-NR^{a63}R^{a64}$, $-C(O)R^{65}$, $-C(O)OR^{66}$, $-OC(O)R^{67}$, $-OC(O)OR^{68}$, $-C(O)NR^{a69}R^{a610}$, $-N(R^{611})C(O)R^{612}$, $S(O)R^{613}$, $-S(O)_2R^{614}$, $-S(O)_2NR^{a615}R^{a616}$, $-OC(O)NR^{a617}R^{a618}$, $-N(R^{619})C(O)OR^{620}$, $-N(R^{621})C(O)NR^{a622}R^{a623}$, $-N(R^{624})S(O)_2R^{625}$ or $-OP(O)(OR^{626})_2$; $R^{61}$, $R^{62}$, $R^{a63}$, $R^{a64}$, $R^{65}$, $R^{66}$, $R^{67}$, $R^{68}$, $R^{a69}$, $R^{a610}$, $R^{611}$, $R^{612}$, $R^{613}$, $R^{614}$, $R^{a615}$, $R^{a616}$, $R^{a617}$, $R^{a618}$, $R^{619}$, $R^{620}$, $R^{621}$, $R^{a622}$, $R^{a623}$, $R^{624}$, $R^{625}$ and $R^{626}$ are each independently hydrogen, substituted or unsubstituted $C_{1-6}$ alkyl, substituted or unsubstituted $C_{2-8}$ alkenyl, substituted or unsubstituted $C_{2-8}$ alkynyl, substituted or unsubstituted $C_{3-10}$ cycloalkyl, substituted or unsubstituted $C_{2-8}$ heterocycloalkyl, substituted or unsubstituted $C_{6-20}$ aryl, or substituted or unsubstituted $C_{2-10}$ heteroaryl;
in $R^{q1}$, $R^{q2}$, $R^{q3}$, $R^{q4}$, $R^{q5}$, $R^{q6}$, $R^{q7}$, $R^{q8}$, $R^{q9}$, $R^{q10}$, $R^{q11}$, $R^{q12}$, $R^{q13}$, $R^{q14}$, $R^{q15}$, $R^{q16}$, $R^{q17}$, $R^{q18}$, $R^{q19}$, $R^{q20}$, $R^{q21}$ and $R^{q22}$, substituents in the substituted $C_{1-6}$ alkyl, substituted $C_{2-8}$ alkenyl, substituted $C_{2-8}$ alkynyl, substituted $C_{3-10}$ cycloalkyl, substituted $C_{2-8}$ heterocycloalkyl, substituted $C_{6-20}$ substituted aryl and substituted $C_{2-10}$ heteroaryl are each independently one or more of the following groups: deuterium, halogen, $C_{1-6}$ alkyl, halogen substituted $C_{1-6}$ alkyl, $C_{2-8}$ alkenyl, $C_{2-8}$ alkynyl, $C_{3-10}$ cycloalkyl, $C_{2-8}$ heterocycloalkyl, $C_{6-20}$ aryl, $C_{2-10}$ heteroaryl, cyano, $-OR^{71}$, $-SR^{72}$, $-NR^{a73}R^{a74}$, $-C(O)R^{75}$, $-C(O)OR^{76}$, $-OC(O)R^{77}$, $-OC(O)OR^{78}$, $-C(O)NR^{a79}R^{a710}$, $-N(R^{711})C(O)R^{712}$, $S(O)R^{713}$, $-S(O)_2R^{714}$, $-S(O)_2NR^{a715}R^{a716}$, $-OC(O)NR^{a717}R^{a718}$, $-N(R^{719})C(O)OR^{720}$, $-N(R^{721})C(O)NR^{a722}R^{a723}$, $-N(R^{724})S(O)_2R^{725}$ or $-OP(O)(OR^{726})_2$; when there are multiple substituents, the substituents are the same or different; $R^{71}$, $R^{72}$, $R^{a73}$, $R^{a74}$, $R^{75}$, $R^{76}$, $R^{77}$, $R^{78}$, $R^{a79}$, $R^{a710}$, $R^{711}$, $R^{712}$, $R^{713}$, $R^{714}$, $R^{a715}$, $R^{a716}$, $R^{a717}$, $R^{a718}$, $R^{719}$, $R^{720}$, $R^{721}$, $R^{a722}$, $R^{a723}$, $R^{724}$, $R^{725}$ and $R^{726}$ are each independently $C_{1-6}$ alkyl, halogen substituted $C_{1-6}$ alkyl, $C_{2-8}$ alkenyl, $C_{2-8}$ alkynyl, $C_{3-10}$ cycloalkyl, $C_{2-8}$ heterocycloalkyl, $C_{6-20}$ aryl or $C_{2-10}$ heteroaryl; in $R^{61}$, $R^{62}$, $R^{a63}$, $R^{a64}$, $R^{65}$, $R^{66}$, $R^{67}$, $R^{68}$, $R^{a69}$, $R^{a610}$, $R_{611}$, $R^{612}$, $R^{613}$, $R^{a614}$, $R^{a615}$, $R^{a616}$, $R^{a617}$, $R^{a618}$, $R^{619}$, $R^{620}$, $R^{621}$, $R^{a622}$, $R^{a623}$, $R^{624}$, $R^{625}$ and $R^{626}$, substituents in the substituted $C_{1-6}$ alkyl, substituted $C_{2-8}$ alkenyl, substituted $C_{2-8}$ alkynyl, substituted $C_{3-10}$ cycloalkyl, substituted $C_{2-8}$ heterocycloalkyl, substituted $C_{6-20}$ aryl and substituted $C_{2-10}$ heteroaryl are each independently one or more of the following groups: deuterium, halogen, cyano, $C_{1-6}$ alkyl, halogen substituted $C_{1-6}$ alkyl, $C_{2-8}$ alkenyl, $C_{2-8}$ alkynyl, $C_{3-10}$ cycloalkyl, $C_{2-8}$ heterocycloalkyl, $C_{6-20}$ aryl, $C_{2-10}$ heteroaryl, $-OR^c$, $-SR^{c1}$, $-NR^{b1}R^{b2}$, $-C(O)R^{c2}$, $-C(O)OR^{c3}$, $-OC(O)R^{c4}$, $-OC(O)OR^{c5}$, $-C(O)NR^{b3}R^{b4}$, $-N(R^{c6})C(O)OR^{c7}$, $S(O)R^{c8}$, $-S(O)_2R^{c9}$, $-S(O)_2NR^{b5}R^{b6}$, $-N(R^{c10})C(O)R^{c11}$, $-N(R^{c12})C(O)NR^{b7}R^{b8}$ or $-N(R^{c13})S(O)_2R^{c14}$; $R^c$, $R^{c1}$, $R^{b1}$, $R^{b2}$, $R^{c2}$, $R^{c3}$, $R^{c4}$, $R^{c5}$, $R^{b3}$, $R^{b4}$, Rob, $R^{c7}$, $R^{c8}$, $R^{c9}$, $R^{b5}$, $R^{b6}$, $R^{c10}$, $R^{c12}$, $R^{b7}$, $R^{b8}$, $R^{c13}$ and $R^{c14}$ are each independently hydrogen, hydroxyl, $C_{1-6}$ alkyl, halogen substituted $C_{1-6}$ alkyl, $C_{3-10}$ cycloalkyl, $C_{2-8}$ heterocycloalkyl, $C_{6-20}$ aryl or $C_{2-10}$ heteroaryl;

$Q^3$ and $Q^{31}$ are independently S or O;

$Q^4$ and $Q^{41}$ are independently $CR^{q23}$ or N; $R^{q23}$ and $R^{q1}$ have the same definition;

or two adjacent $R^{qx}$ and the atoms to which they are connected form a ring structure; the ring structure is substituted or unsubstituted $C_{3-10}$ cycloalkyl, substituted or unsubstituted $C_{2-8}$ heterocycloalkyl, substituted or unsubstituted $C_{6-20}$ aryl, or substituted or unsubstituted $C_{2-10}$ heteroaryl; in the ring structure, substituents in the substituted $C_{3-10}$ cycloalkyl, substituted $C_{2-8}$ heterocycloalkyl, substituted $C_{6-20}$ aryl or substituted $C_{2-10}$ heteroaryl are each independently one or more of the following groups: deuterium, halogen, cyano, $C_{1-6}$ alkyl, halogen substituted $C_{1-6}$ alkyl, $C_{2-8}$ alkenyl, $C_{2-8}$ alkynyl, $-OR^{a15}$, $-SR^{a16}$, $-C(O)OR^{a17}$, $-COR^{a18}$, $-C(O)NH_2$, $C_{3-10}$ cycloalkyl, $C_{2-8}$ heterocycloalkyl, $C_{6-20}$ aryl, $C_{2-10}$ heteroaryl; $R^{a15}$, $R^{a16}$, $R^{a17}$ and $R^{a18}$ are each independently hydrogen or $C_{1-6}$ alkyl; when there are multiple substituents, the substituents are the same or different;

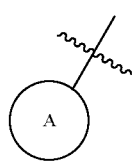

is

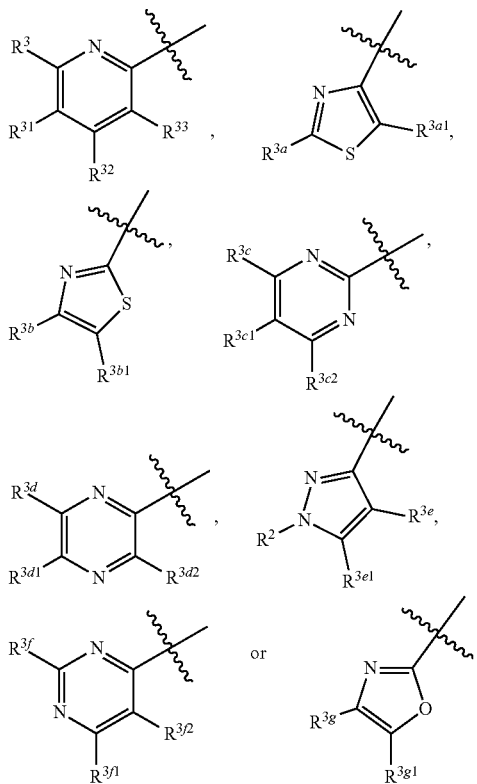

in ring A, $R^3$, $R^{31}$, $R^{32}$, $R^{33}$, $R^{3a}$, $R^{3a1}$, $R^{3b}$, $R^{3b1}$, $R^{3c}$, $R^{3c1}$, $R^{3c2}$, $R^{3d}$, $R^{3d1}$, $R^{3d2}$, $R^{3e}$, $R^{3e1}$, $R^{3f}$, $R^{3f1}$, $R^{3f2}$, $R^{3g}$ and $R^{3g1}$ are each independently hydrogen, halogen, cyano, nitro, —$NR^{a3}R^{a4}$, —$OR^{a5}$, —$SR^{a6}$, —$C(O)OR^{a7}$, —$C(O)NR^{a8}R^{a9}$, —$COR^{a10}$, substituted or unsubstituted $C_{1-6}$ alkyl, substituted or unsubstituted $C_{2-8}$ alkenyl, substituted or unsubstituted $C_{2-8}$ alkynyl, substituted or unsubstituted $C_{3-10}$ cycloalkyl, substituted or unsubstituted $C_{2-8}$ heterocycloalkyl, substituted or unsubstituted $C_{4-8}$ cycloalkenyl, substituted or unsubstituted $C_{6-20}$ aryl, or substituted or unsubstituted $C_{2-10}$ heteroaryl;

$R^{a4}$, $R^{a5}$, $R^{a6}$, $R^{a7}$, $R^{a9}$ and $R^{a10}$ are each independently hydrogen, substituted or unsubstituted $C_{1-6}$ alkyl, $C_{2-8}$ alkenyl, $C_{2-8}$ alkynyl, $C_{3-10}$ cycloalkyl, $C_{2-8}$ heterocycloalkyl, $C_{6-20}$ aryl or $C_{2-10}$ heteroaryl;

$R^{a3}$ and $R^{a8}$ are each independently hydrogen, substituted or unsubstituted $C_{1-6}$ alkyl, $C_{2-8}$ alkenyl, $C_{2-8}$ alkynyl, hydroxyl, $C_{3-10}$ cycloalkyl, $C_{2-8}$ heterocycloalkyl, $C_{6-20}$ aryl or $C_{2-10}$ heteroaryl;

in $R^3$, $R^{31}$, $R^{32}$, $R^{33}$, $R^{3a}$, $R^{3a1}$, $R^{3b}$, $R^{3b1}$, $R^{3c}$, $R^{3c1}$, $R^{3c2}$, $R^{3d1}$, $R^{3d2}$, $R^{3e}$, $R^{3e1}$, $R^{3f}$, $R^{3f1}$, $R^{3f2}$, $R^{3g}$ and $R^{3g1}$, substituents in the substituted $C_{1-6}$ alkyl, substituted $C_{2-8}$ alkenyl, substituted $C_{2-8}$ alkynyl, substituted $C_{3-10}$ cycloalkyl, substituted $C_{2-8}$ heterocycloalkyl, substituted $C_{4-8}$ cycloalkenyl, substituted $C_{6-20}$ aryl and substituted $C_{2-10}$ heteroaryl, and substituents in the substituted $C_{1-6}$ alkyl in $R^{a3}$, $R^{a4}$, $R^{a5}$, $R^{a6}$, $R^{a7}$, $R^{a8}$, $R^{a9}$ and $R^{a10}$ are each independently one or more of the following groups: deuterium, halogen, cyano, $C_{1-6}$ alkyl, halogen substituted $C_{1-6}$ alkyl, $C_{2-8}$ alkenyl, $C_{2-8}$ alkynyl, —$OR^{a15}$, —$SR^{a16}$, —$C(O)OR^{a17}$, —$COR^{a18}$, —$C(O)NH_2$, $C_{3-10}$ cycloalkyl, $C_{2-8}$ heterocycloalkyl, $C_{6-20}$ aryl, or $C_{2-10}$ heteroaryl; $R^{a15}$, $R^{a16}$, $R^{a17}$ and $R^{a18}$ are each independently hydrogen or $C_{1-6}$ alkyl; when there are multiple substituents, the substituents are the same or different;

$R^2$ is hydrogen, cyano, $C_{1-6}$ alkyl, $C_{3-10}$ cycloalkyl, $C_{2-8}$ heterocycloalkyl, —$C(O)OR^{a19}$ or $C_{1-6}$ alkyl substituted by —$OR^{a20}$; $R^{a19}$ and $R^{a20}$ are independently $C_{1-6}$ alkyl;

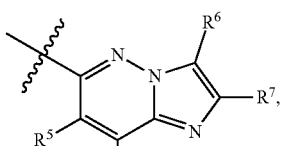

is

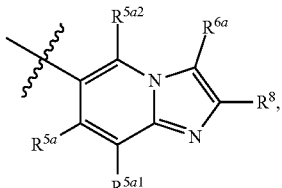

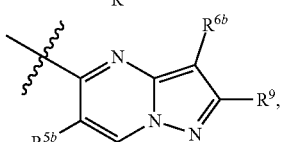

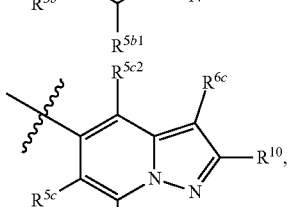

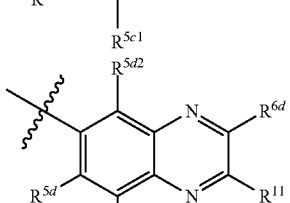

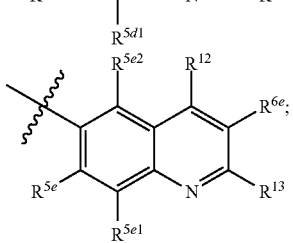

in ring B, $R^5$, $R^{51}$, $R^{5a}$, $R^{5a1}$, $R^{5a2}$, $R^{5b}$, $R^{5b1}$, $R^{5c}$, $R^{5c1}$, $R^{5c2}$, $R^{5d}$, $R^{5d1}$, $R^{5d2}$, $R^{5e}$, $R^{5e1}$ and $R^{5e2}$ are each independently hydrogen, deuterium or halogen;

$R^6$, $R^{6a}$, $R^{6b}$, $R^{6c}$, $R^{6d}$ and $R^{6e}$ have the same definition as $R^{q1}$; provided that $R^6$, $R^{6a}$, $R^{6b}$, $R^{6c}$, $R^{6d}$ and $R^{6e}$ are not cyano;

$R^7$, $R^8$, $R^9$, $R^{10}$, $R^{11}$, $R^{12}$ and $R^{13}$ are each independently hydrogen, deuterium or halogen;

or in the above groups or substituents, when $NR^X R^Y$ is present, then $R^X$, $R^Y$ and N to which they are attached form substituted or unsubstituted 3-8 membered heterocyclyl; heteroatom in the 3-8 membered heterocyclyl is selected from N, N and O, N and S, or N, O and S; the number of heteroatom is 1, 2, 3 or 4; substituents in the substituted 3-8 membered heterocyclyl are one or more of the following groups: deuterium, halogen, cyano, $C_{1-6}$ alkyl, $C_{2-8}$ alkenyl, $C_{2-8}$ alkynyl, $-OR^{a81}$, $-SR^{a82}$, $-C(O)OR^{a83}$, $-COR^{a84}$, $-C(O)NH_2$, $C_{3-10}$ cycloalkyl, $C_{2-8}$ heterocycloalkyl, $C_{6-20}$ aryl or $C_{2-10}$ heteroaryl; $R^{a81}$, $R^{a82}$, $R^{a83}$ and $R^{a84}$ are each independently hydrogen or $C_{1-6}$ alkyl;

when ring Q is

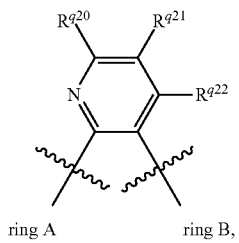

ring A      ring B, then

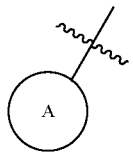

A is not

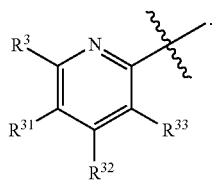

In the present invention, $-NR^X R^Y$ is, for example, $-NR^{a3}R^{a4}$, $-NR^{a8}R^{a9}$, $-NR^{a63}R^{a64}$, $-NR^{a69}R^{a610}$, $-NR^{a615}R^{a616}$, $-NR^{a617}R^{a618}$, $-NR^{a622}R^{a623}$, $-NR^{a73}R^{a74}$, $-NR^{a79}R^{a710}$, $-NR^{a715}R^{a716}$, $-NR^{a717}R^{a718}$, $-NR^{a722}R^{a723}$, $-NR^{b1}R^{b2}$, $-NR^{b3}R^{b4}$, $-NR^{b5}R^{b6}$ or $-NR^{b7}R^{b8}$.

Two adjacent $R^{qx}$ and the atoms to which they are connected form a ring structure, wherein, the two adjacent $R^{qx}$ are, for example, $R^{q1}$ and $R^{q2}$; $R^{q2}$ and $R^{q3}$; $R^{q4}$ and $R^{q5}$; $R^{q5}$ and $R^{q6}$; $R^{q7}$ and $R^{q8}$; $R^{q9}$ and $R^{q10}$; $R^{q17}$ and $R^{q18}$; $R^{q18}$ and $R^{q19}$; $R^{q20}$ and $R^{q21}$; $R^{q21}$ and $R^{q22}$; when $Q^4$ and $Q^{41}$ are $CR^{23}$, then the two adjacent $R^{qx}$ can also be $R^{q15}$ and $R^{q23}$; $R^{q16}$ and $R^{q23}$.

In the present invention, the $C_{1-6}$ alkyl in the term substituted or unsubstituted $C_{1-6}$ alkyl and the term $C_{1-6}$ alkyl are independently preferably $C_{1-4}$ alkyl; the $C_{1-4}$ alkyl is preferably methyl, ethyl, n-propyl, isopropyl, n-butyl, isobutyl, or tert-butyl.

In the present invention, the $C_{2-8}$ alkenyl in the term substituted or unsubstituted $C_{2-8}$ alkenyl and the term $C_{2-8}$ alkenyl are independently preferably $C_{2-4}$ alkenyl. The $C_{2-4}$ alkenyl is preferably vinyl, propenyl, allyl,

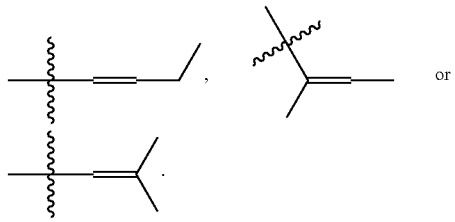

In the present invention, the $C_{2-8}$ alkynyl in the term substituted or unsubstituted $C_{2-8}$ alkynyl and the term $C_{2-8}$ alkynyl are independently $C_{2-4}$ alkynyl. The $C_{2-4}$ alkynyl is preferably ethynyl, propynyl, butynyl or 3-methylpropynyl.

In the present invention, the $C_{3-10}$ cycloalkyl in the term substituted or unsubstituted $C_{3-10}$ cycloalkyl and the term $C_{3-10}$ cycloalkyl are independently preferably cyclopropyl, cyclobutyl, cyclopentyl, cyclohexyl, cycloheptyl, cyclooctyl, cyclononyl, cyclodecyl, bicyclo[3.1.1]heptyl, bicyclo[2.2.1]heptyl, bicyclo[2.2.2]octyl, bicyclo[3.2.2]nonyl, bicyclo[3.3.1]nonyl or bicyclo[4.2.1]nonyl.

In the present invention, the $C_{2-8}$ heterocycloalkyl in the term substituted or unsubstituted $C_{2-8}$ heterocycloalkyl and the term $C_{2-8}$ heterocycloalkyl are independently preferably azetidinyl, azepanyl, aziridine, diazcycloheptyl, 1,3-dioxanyl, 1,3-dioxopenyl, 1,3-dithiopentyl, 1,3-dithianyl, imidazolinyl, imidazolidinyl, isothiazolidinyl, isothiazolyl, isoxazolinyl, morpholinyl, oxadiazolinyl, oxadiazolidinyl, oxazolinyl, oxazolidinyl, piperazinyl, piperidinyl, pyranyl, pyrazolinyl, pyrazolidinyl, pyrrolinyl, pyrrolidinyl, tetrahydrofuranyl, tetrahydrothienyl, thiadiazolinyl, thiadiazolidinyl, thiazolinyl, thiazolidinyl, thiomorpholinyl, 1,1-dioxothiomorpholinyl, thiopyranyl, trithianyl, 2,3-dihydrobenzofuran-2-yl, 2,3-dihydrobenzofuran-3-yl, indoline-1-yl, indoline-2-yl, indoline-3-yl, 2,3-dihydrobenzothiophene-2-yl, decahydroquinolinyl, decahydroisoquinolinyl, octahydro-1H-indolyl or octahydrobenzofuranyl.

In the present invention, the $C_{4-8}$ cycloalkenyl in the term substituted or unsubstituted $C_{4-8}$ cycloalkenyl and the term $C_{4-8}$ cycloalkenyl are independently preferably cyclobutenyl, cyclopentenyl, cyclohexenyl, cycloheptenyl, cyclooctenyl, norbornenyl or bicyclo[2.2.2]octenyl.

In the present invention, the $C_{6-20}$ aryl in the term substituted or unsubstituted $C_{6-20}$ aryl or the term $C_{6-20}$ aryl are independently preferably phenyl, naphthyl, anthryl, phenanthryl, azulenyl, indan-1-yl, indan-2-yl, indan-3-yl, indan-4-yl, 2,3-indoline-4-yl, 2,3-indoline-5-yl, 2,3-indoline-6-yl, 2,3-indoline-7-yl, inden-1-yl, inden-2-yl, inden-3-yl, inden-4-yl, dihydronaphthalene-2-yl, dihydronaphthalene-3-yl, dihydronaphthalene-4-yl, dihydronaphthalene-1-yl, 5,6,7,8-tetrahydronaphthalene-1-yl, 5,6,7,8-tetrahydronaphthalene-2-yl, 2,3-dihydrobenzofuran-4-yl, 2,3-dihydrobenzofuran-5-yl, 2,3-dihydrobenzofuran-6-yl, 2,3-dihydrobenzofuran-7-yl, benzo[d][1,3]dioxol-4-yl, benzo[d][1,3]dioxol-5-yl, 2H-benzofuran-2-one-5-yl, 2H-benzofuran-2-one-6-yl, 2H-benzofuran-2-one-7-yl, 2H-benzofuran-2-one-8-yl, isoindoline-1,3-dione-4-yl, isoindoline-1,3-dione-5-yl, inden-1-one-4-yl, inden-1-one-5-yl, inden-1- one-6-yl, inden-1-one-7-yl, 2,3-dihydrobenzo[b] [1,4] dioxane-5-yl, 2,3-dihydrobenzo[b][1,4]dioxane-6-yl, 2H-benzo[b] [1,4] oxazine3 (4H)-one-5-yl, 2H-benzo[b] [1,4]oxazine3 (4H)-one-6-yl, 2H-benzo[b] [1,4] oxazine3 (4H)-one-7-yl, 2H-benzo[b] [1,4]oxazine3 (4H)-one-8-yl, benzo[d]oxazine-2(3H)-one-5-yl, benzo[d]oxazine-2(3H)-one-6-yl, benzo[d]oxazine-2(3H)-one-7-yl, benzo[d]oxazine-2(3H)-one-8-yl, quinazolin-4(3H)-one-5-yl, quinazolin-4(3H)-one-6-yl, quinazolin-4(3H)-one-7-yl, quinazolin-4(3H)-one-8-yl, quinoxalin-2(1H)-one-5-yl, quinoxalin-2(1H)-one-6-yl, quinoxaline-2(1H)-one-7-yl, quinoxaline-2(1H)-one-8-yl, benzo[d] thiazol-2(3H)-one-4-yl, benzo[d] thiazol-2(3H)-one-5-yl, benzo[d]thiazo-2(3H)-one-6-yl or benz[d]thiazole-2(3H)-one-7-yl.

In the present invention, the $C_{2-10}$ heteroaryl in the term substituted or unsubstituted $C_{2-10}$ heteroaryl and the term $C_{2-10}$ heteroaryl are independently preferably furanyl, imidazolyl, isoxazolyl, isothiazolyl, oxadiazolyl, oxazolyl, pyridyl, pyridazinyl, pyrimidinyl, pyrazinyl, pyrazolyl, pyrrolyl, tetrazolyl, thiadiazolyl, thiazolyl, thienyl, triazolyl, triazinyl, benzimidazolyl, benzofuranyl, benzothienyl, benzoxadiazolyl, benzothiazolyl, cinnolinyl, 5,6-dihydroquinolin-2-yl, 5,6-dihydroquinolin-1-yl, furopyridinyl, indazolyl, indolyl, isoquinolinyl, naphthyridinyl, purinyl, quinolinyl, 5,6,7,8-tetrahydroquinolin-2-yl, 5,6,7,8-tetrahydroquinolin-3-yl, 5,6,7,8-tetrahydroquinolin-4-yl, 5,6,7,8-tetrahydroisoquinolin-1-yl, thienopyridyl, 4,5,6,7-tetrahydro [c][1,2,5] oxadiazolyl or 6,7-dihydropyro [c][1,2,5] oxadiazol-4(5H) one.

In a preferred embodiment of the invention, in ring Q, $R^{q1}, R^{q2}, R^{q3}, R^{q4}, R^{q5}, R^{q6}, R^{q7}, R^{q8}, R^{q9}, R^{q10}, R^{q11}, R^{q12}, R^{q13}, R^{q14}, R^{q15}, R^{q16}, R^{q17}, R^{q18}, R^{q19}, R^{q20}, R^{q21}$ and $R^{q22}$ are each independently hydrogen, deuterium, halogen, sulfonic acid group, $C_{1-6}$ alkyl, $C_{2-8}$ alkenyl, $C_{2-8}$ alkynyl, $C_{3-10}$ cycloalkyl, $C_{2-8}$ heterocycloalkyl, $C_{6-20}$ aryl, $C_{2-10}$ heteroaryl, cyano, —$OR^{61}$, —$SR^{62}$, —$NR^{a63}R^{a64}$, —$C(O)R^{65}$, —$C(O)OR^{66}$, —$OC(O)R^{67}$, —$OC(O)OR^{68}$, —$C(O)NR^{a69}R^{a610}$, —$N(R^{611})C(O)R^{612}$, $S(O)R^{613}$, —$S(O)_2R^{614}$, —$S(O)_2NR^{a615}R^{a616}$, —$OC(O)NR^{a617}R^{a618}$, $N(R^{619})C(O)OR^{620}$, —$N(R^{621})C(O)NR^{a622}R^{a623}$, —$N(R^{624})S(O)_2R^{625}$ or —$OP(O)(OR^{626})_2$, $R^{61}, R^{62}, R^{a63}, R^{a64}, R^{65}, R^{66}, R^{67}, R^{68}, R^{a69}, R^{a610}, R^{611}, R^{612}, R^{613}, R^{614}, R^{a615}, R^{a616}, R^{a617}, R^{a618}, R^{619}, R^{620}, R^{621}, R^{a622}, R^{a623}, R^{624}, R^{625}$ and $R^{626}$ are as defined above; or two adjacent $R^{qx}$ and the atoms to which they are connected form a ring structure; the ring structure is substituted or unsubstituted $C_{3-10}$ cycloalkyl, substituted or unsubstituted $C_{2-8}$ heterocycloalkyl, substituted or unsubstituted $C_{6-20}$ aryl, or substituted or unsubstituted $C_{2-10}$ heteroaryl; substituents in the substituted $C_{3-10}$ cycloalkyl, substituted $C_{2-8}$ heterocycloalkyl, substituted $C_{6-20}$ aryl and substituted $C_{2-10}$ heteroaryl are as defined above.

In a preferred embodiment of the invention, in ring Q, $R^{q1}, R^{q2}, R^{q3}, R^{q4}, R^{q5}, R^{q6}, R^{q7}, R^{q8}, R^{q9}, R^{q10}, R^{q11}, R^{q12}, R^{q13}, R^{q14}, R^{q15}, R^{q16}, R^{q17}, R^{q18}, R^{q19}, R^{q20}, R^{q21}$ and $R^{q22}$ are each independently hydrogen, deuterium, halogen or $C_{1-6}$ alkyl.

In a preferred embodiment of the invention, in ring Q, $R^{q1}, R^{q2}, R^{q3}, R^{q4}, R^{q5}, R^{q6}, R^{q7}, R^{q8}, R^{q9}, R^{q10}, R^{q11}, R^{q12}, R^{q13}, R^{q14}, R^{q15}, R^{q16}, R^{q17}, R^{q18}, R^{q19}, R^{q20}, R^{q21}$ and $R^{q22}$ are each independently hydrogen or $C_{1-6}$ alkyl.

In a preferred embodiment of the invention, ring Q is

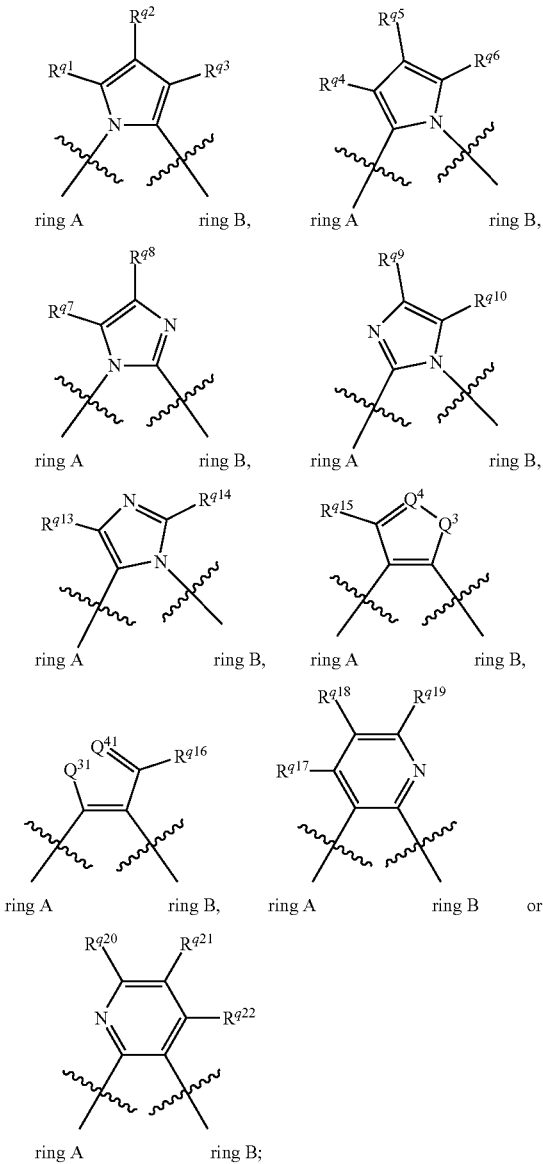

$R^{q1}, R^{q2}, R^{q3}, R^{q4}, R^{q5}, R^{q6}, R^{q7}, R^{q8}, R^{q13}, R^{q14}, R^{q15}, R^{q16}, R^{q17}, R^{q18}, R^{q19}, R^{q20}, R^{q21}$ and $R^{q22}$ are as defined above; preferably, $R^{q5}$ and $R^{q6}$ together with the atoms to which they are attached form $C_{6-20}$ aryl, such as phenyl.

In a preferred embodiment of the invention, ring Q is

-continued

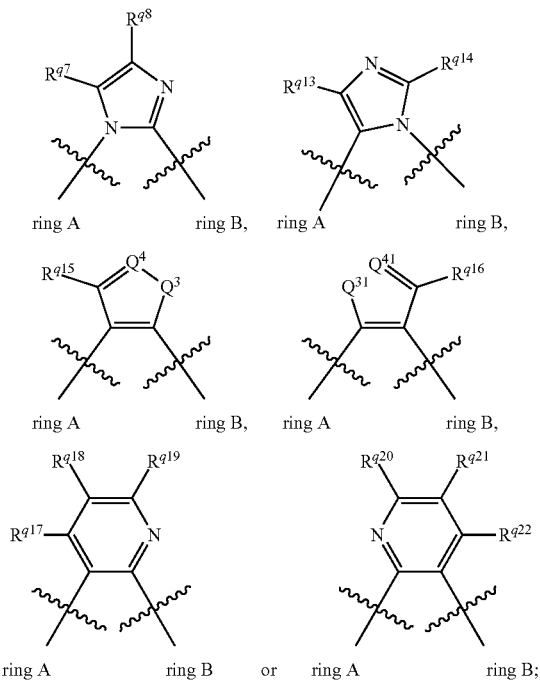

$R^{q1}$, $R^{q2}$, $R^{q3}$, $R^{q4}$, $R^{q5}$, $R^{q6}$, $R^{q7}$, $R^{q8}$, $R^{q13}$, $R^{q14}$, $R^{q15}$, $R^{q16}$, $R^{q17}$, $R^{q18}$, $R^{q19}$, $R^{q20}$, $R^{q21}$ and $R^{q22}$ are as defined above.

In a preferred embodiment of the invention, ring Q is

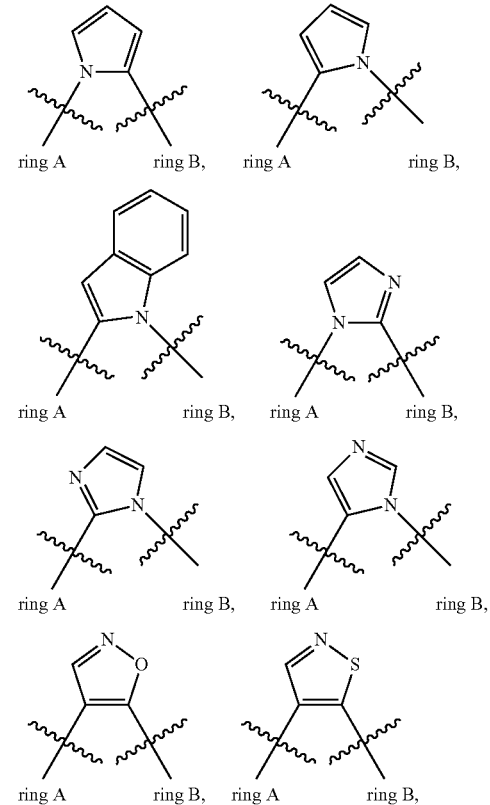

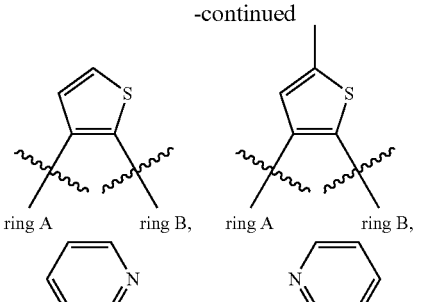

further preferably is

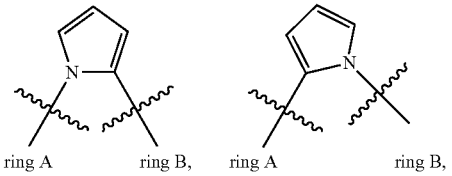

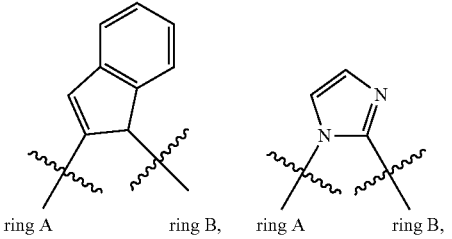

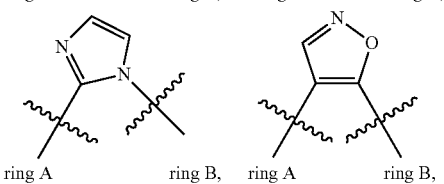

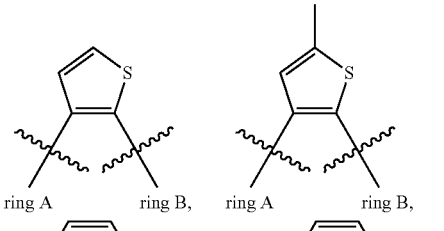

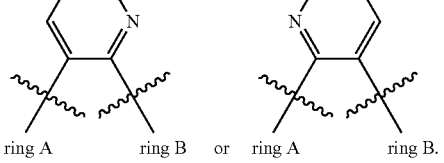

In a preferred embodiment of the invention, in ring A, $R^3$, $R^{31}$, $R^{32}$, $R^{33}$, $R^{3a}$, $R^{3a1}$, $R^{3b}$, $R^{3b1}$, $R^{3c}$, $R^{3c1}$, $R^{3c2}$, $R^{3d}$, $R^{3d1}$, $R^{3d2}$, $R^{3e}$, $R^{3e1}$, $R^{3f}$, $R^{3f1}$, $R^{3f2}$, $R^{3g}$ and $R^{3g1}$ are each independently hydrogen, halogen, cyano, nitro, —NR$^{a3}$R$^{a4}$, —OR$^{a5}$, —SR$^{a6}$, —C(O)OR$_{a7}$, —C(O)NR$^{a8}$R$^{a9}$, —COR$^{a10}$, substituted or unsubstituted C$_{1-6}$ alkyl, substituted or unsubstituted C$_{2-8}$ heterocycloalkyl, substituted or unsubstituted C$_{6-20}$ aryl, or substituted or unsubstituted $C_{2-10}$ heteroaryl; wherein $R^{a3}$, $R^{a4}$, $R^{a5}$, $R^{a6}$, $R^{a7}$, $R^{a8}$, $R^{a9}$ and $R^{a10}$ are as defined above; the substituted or unsubstituted $C_{1-6}$ alkyl, the substituted or unsubstituted $C_{2-8}$ heterocycloalkyl, the substituted or unsubstituted $C_{6-20}$ aryl, and the substituted or unsubstituted $C_{2-10}$ heteroaryl are as defined above.

In a preferred embodiment of the invention, in ring A, $R^3$, $R^{31}$, $R^{32}$, $R^{33}$, $R^{3a}$, $R^{3a1}$, $R^{3b}$, $R^{3b1}$, $R^{3c}$, $R^{3c1}$, $R^{3c2}$, $R^{3d}$, $R^{3d1}$, $R^{3d2}$, $R^{3e}$, $R^{3e1}$, $R^{3f}$, $R^{3f1}$, $R^{3f2}$, $R^{3g}$ and $R^{3g1}$ are each independently hydrogen, halogen, $OR^{a5}$, —$SR^{a6}$, —C(O)NR$^{a8}$R$^{a9}$, or substituted or unsubstituted $C_{1-6}$ alkyl; wherein $R^{a5}$, $R^{a6}$, $R^{a8}$ and $R^{a9}$ are as defined above; substituents in the substituted $C_{1-6}$ alkyl are as defined above.

In a preferred embodiment of the invention, in ring A, $R^3$, $R^{31}$, $R^{32}$, $R^{33}$, $R^{3a}$, $R^{3a1}$, $R^{3b}$, $R^{3b1}$, $R^{3c}$, $R^{3c1}$, $R^{3c2}$, $R^{3d}$, $R^{3d1}$, $R^{3d2}$, $R^{3e}$, $R^{3e1}$, $R^{3f}$, $R^{3f1}$, $R^{3f2}$, $R^{3g}$ and $R^{3g1}$ are each independently hydrogen, halogen, $OR^{a5}$, or substituted or unsubstituted $C_{1-6}$ alkyl; wherein $R^{a5}$ is preferably hydrogen or $C_{1-6}$ alkyl, substituents in the substituted $C_{1-6}$ alkyl are preferably one or more of the following substituents: deuterium or halogen.

In a preferred embodiment of the invention, in ring A, $R^3$, $R^{31}$, $R^{32}$, $R^{33}$, $R^{3a}$, $R^{3a1}$, $R^{3b}$, $R^{3b1}$, $R^{3c}$, $R^{3c1}$, $R^{3c2}$, $R^{3d}$, $R^{3d1}$, $R^{3d2}$, $R^{3e}$, $R^{3e1}$, $R^{3f}$, $R^{3f1}$, $R^{3f2}$, $R^{3g}$ and $R^{3g1}$ are each independently hydrogen, $C_{1-6}$ alkyl or halogen substituted $C_{1-6}$ alkyl, the number of halogen is one or more than one (for example, 1-6; such as 1-3).

In a preferred embodiment of the invention, in ring A, $R^3$, $R^{31}$, $R^{32}$, $R^{33}$, $R^{3a}$, $R^{3a1}$, $R^{3b}$, $R^{3b1}$, $R^{3c}$, $R^{3c1}$, $R^{3c2}$, $R^{3d}$, $R^{3d1}$, $R^{3d2}$, $R^{3e}$, $R^{3e1}$, $R^{3f}$, $R^{3f1}$, $R^{3f2}$, $R^{3g}$ and $R^{3g1}$ are each independently hydrogen, halogen, trifluoromethyl, difluoromethyl, deuterated methyl, methyl or methoxy.

In a preferred embodiment of the invention, in ring A, $R^3$, $R^{31}$, $R^{32}$, $R^{33}$, $R^{3a}$, $R^{3a1}$, $R^{3b}$, $R^{3b1}$, $R^{3c}$, $R^{3c1}$, $R^{3c2}$, $R^{3d}$, $R^{3d1}$, $R^{3d2}$, $R^{3e}$, $R^{3e1}$, $R^{3f}$, $R^{3f1}$, $R^{3f2}$, $R^{3g}$ and $R^{3g1}$ are each independently hydrogen, trifluoromethyl or methyl.

In a preferred embodiment of the invention, $R^2$ is hydrogen, $C_{1-6}$ alkyl or $C_{3-10}$ cycloalkyl.

In a preferred embodiment of the invention,

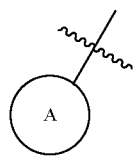

is

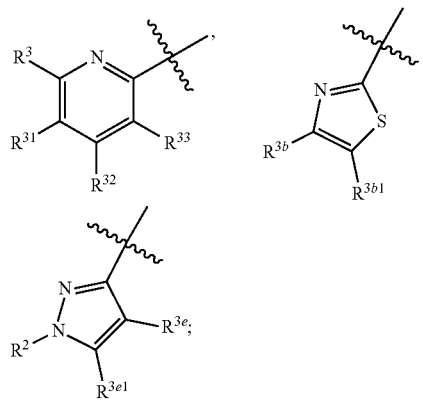

$R^3$, $R^{31}$, $R^{32}$, $R^{33}$, $R^{3b}$, $R^{3b1}$, $R^{2e}$, $R^{3e1}$ and $R^2$ are as defined above.

In a preferred embodiment of the invention,

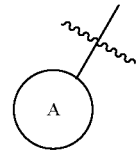

is

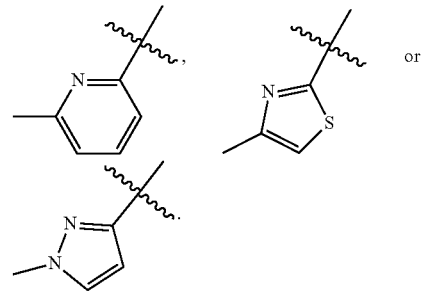

In a preferred embodiment of the invention, in ring B, $R^5$, $R^{51}$, $R^{5a}$, $R^{5a1}$, $R^{5a2}$, $R^{5b}$, $R^{5b1}$, $R^{5c}$, $R^{5c1}$, $R^{5c2}$, $R^{5d}$, $R^{5d1}$, $R^{5d2}$, $R^{5e}$, $R^{5e1}$ and $R^{5e2}$ are each independently hydrogen.

In a preferred embodiment of the invention, in ring B, $R^7$, $R^8$, $R^9$, $R^{10}$, $R^{11}$, $R^{12}$ and $R^{13}$ are each independently hydrogen.

In a preferred embodiment of the invention, in ring B, $R^6$, $R^{6a}$, $R^{6b}$, $R^{6c}$, $R^{6d}$ and $R^{6e}$ are each independently hydrogen, halogen, substituted or unsubstituted $C_{1-6}$ alkyl, substituted or unsubstituted $C_{2-8}$ heterocycloalkyl, substituted or unsubstituted $C_{6-20}$ aryl, substituted or unsubstituted $C_{2-11}$) heteroaryl, —$OR^{61}$, —$SR^{62}$, —$NR^{a63}R^{a64}$, —C(O)$R^{65}$, —C(O)$OR^{66}$, —OC(O)$R^{67}$, —OC(O)$OR^{68}$, —C(O)$NR^{a69}R^{a610}$, —N($R^{611}$)C(O)$R^{612}$, S(O)$R^{613}$, —S(O)$_2R^{614}$, —S(O)$_2NR^{a615}R^{a616}$, —OC(O)$NR^{a617}R^{a618}$, —N($R^{619}$)C(O)$OR^{620}$, —N($R^{621}$)C(O)$NR^{a622}R^{a623}$, —N($R^{624}$)S(O)$_2R^{625}$ or —OP(O)($OR^{626}$)$_2$, $R^{61}$, $R^{62}$, $R^{a63}$, $R^{a64}$, $R^{65}$, $R^{66}$, $R^{67}$, $R^{68}$, $R^{a69}$, $R^{a610}$, $R^{611}$, $R^{612}$, $R^{613}$, $R^{614}$, $R^{a615}$, $R^{a616}$, $R^{a617}$, $R^{a618}$, $R^{619}$, $R^{620}$, $R^{621}$, $R^{a622}$, $R^{a623}$, $R^{624}$, $R^{625}$ and $R^{626}$ are as defined above; substituents in the substituted $C_{1-6}$ alkyl, substituted $C_{2-8}$ heterocycloalkyl, substituted $C_{6-20}$ aryl or substituted $C_{2-11}$) heteroaryl are as defined above.

In a preferred embodiment of the present invention, in ring B, $R^6$, $R^{6a}$, $R^{6b}$, $R^{6c}$, $R^{6d}$ and $R^{6e}$ are each independently hydrogen, halogen, substituted or unsubstituted $C_{1-6}$ alkyl, substituted or unsubstituted $C_{2-8}$ heterocycloalkyl, substituted or unsubstituted $C_{6-20}$ aryl, substituted or unsubstituted $C_{2-10}$ heteroaryl, —$OR^{61}$, —$SR^{62}$, —$NR^{a63}R^{a64}$, —C(O)$R^{65}$) C(O)$OR^{66}$, —OC(O)$R^{67}$, —OC(O)$OR^{68}$, —C(O)$NR^{a69}R^{a610}$, —N($R^{611}$)C(O)$R^{612}$, S(O)$R^{613}$, —S(O)$_2R^{614}$, —S(O)$_2NR^{a615}R^{a616}$, —OC(O)$NR^{a617}R^{a618}$, —N($R^{619}$)C(O)$OR^{620}$, —N($R^{621}$)C(O)$NR^{a622}R^{a623}$, —N($R^{624}$)S(O)$_2R^{625}$ or —OP(O)($OR^{626}$)$_2$, $R^{61}$, $R^{62}$, $R^{a63}$, $R^{a64}$, $R^{65}$, $R^{66}$, $R^{67}$, $R^{68}$, $R^{a69}$, $R^{a610}$, $R^{611}$, $R^{612}$, $R^{613}$, $R^{614}$, $R^{a615}$, $R^{a616}$, $R^{a617}$, $R^{a618}$, $R^{619}$, $R^{620}$, $R^{621}$, $R^{a622}$, $R^{a623}$, $R^{624}$, $R^{625}$ and $R^{626}$ are as defined above; substituents in the substituted $C_{1-6}$ alkyl, substituted $C_{2-8}$ heterocycloalkyl, substituted $C_{6-20}$ aryl or substituted $C_{2-11}$) heteroaryl are as defined above.

In a preferred embodiment of the present invention, in ring B, $R^6$, $R^{6a}$, $R^{6b}$, $R^{6c}$, $R^{6d}$ and $R^{6e}$ are each independently hydrogen, halogen, substituted or unsubstituted $C_{1-6}$ alkyl, substituted or unsubstituted $C_{2-8}$ heterocycloalkyl, substituted or unsubstituted $C_{6-20}$ aryl, substituted or unsubstituted $C_{2-10}$ heteroaryl, —$OR^{61}$, —$SR^{62}$, —$C(O)R^{65}$, —$C(O)OR^{66}$ or —$C(O)NR^{a69}R^{a610}$, $R^{61}$, $R^{62}$, $R^{65}$, $R^{66}$, $R^{a69}$ and $R^{a610}$ are as defined above; substituents in the substituted $C_{1-6}$ alkyl, substituted $C_{2-8}$ heterocycloalkyl, substituted $C_{6-20}$ aryl or substituted $C_{2-11}$) heteroaryl are as defined above.

In a preferred embodiment of the present invention, in ring B, $R^6$, $R^{6a}$, $R^{6b}$, $R^{6c}$, $R^{6d}$ and $R^{6e}$ are each independently hydrogen, halogen, —$C(O)OR^{66}$ or —$C(O)NR^{a69}R^{a610}$, $R^{66}$, $R^{a69}$ and $R^{a610}$ are as defined above; preferably, $R^{66}$ is hydrogen or $C_{1-6}$ alkyl; and $R^{a69}$ and $R^{a610}$ are independently hydrogen or $C_{1-6}$ alkyl; preferably, $R^{a69}$ and $R^{a610}$ are hydrogen, or one is hydrogen, the other is $C_{1-6}$ alkyl.

In a preferred embodiment of the present invention, in ring B, $R^6$, $R^{6a}$, $R^{6b}$, $R^{6c}$, $R^{6d}$ and $R^{6e}$ are each independently hydrogen, halogen (e.g. Br),

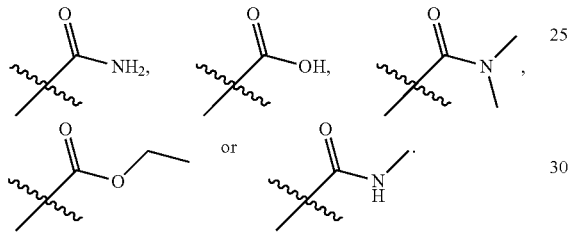

In a preferred embodiment of the present invention,

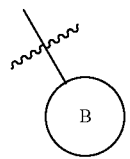

is

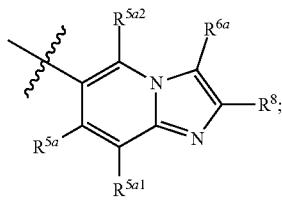

$R^{5a}$, $R^{5a1}$, $R^{5a2}$, $R^{6a}$ and $R^8$ are as defined above.

In a preferred embodiment of the present invention,

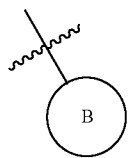

is

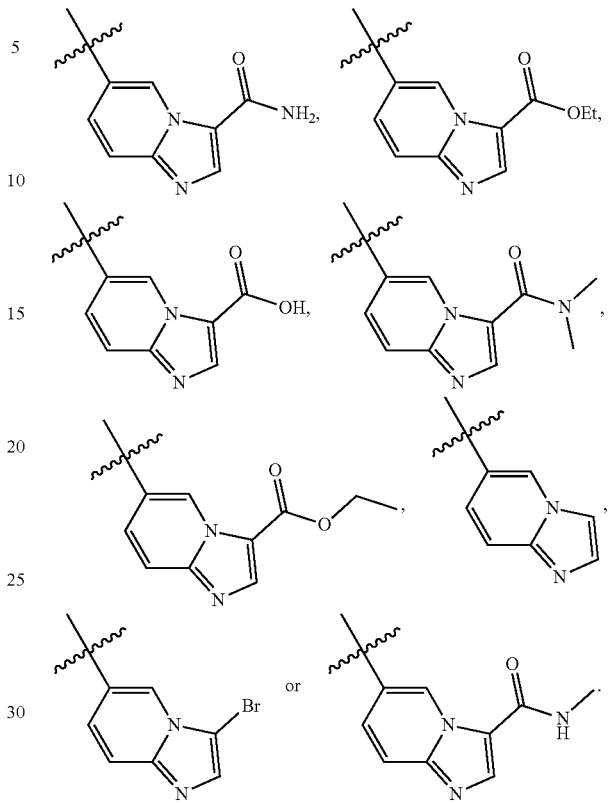

In a preferred embodiment of the present invention,
in ring Q, $R^{a1}$, $R^{q2}$, $R^{q3}$, $R^{q4}$, $R^{q5}$, $R^{q6}$, $R^{q7}$, $R^{q8}$, $R^{q9}$, $R^{q10}$, $R^{q11}$, $R^{q12}$, $R^{q13}$, $R^{q14}$, $R^{q15}$, $R^{q16}$, $R^{q17}$, $R^{q18}$, $R^{q19}$, $R^{q20}$, Roland, $R^{q22}$ are each independently hydrogen, deuterium, halogen or $C_{1-6}$ alkyl;
in ring A, $R^3$, $R^{31}$, $R^{32}$, $R^{33}$, $R^{3a}$, $R^{3a1}$, $R^{3b}$, $R^{3b1}$, $R^{3c}$, $R^{3c1}$, $R^{3c2}$, $R_{3d}$, $R^{3d1}$, $R^{3d2}$, $R^{3e}$, $R^{3e1}$, $R^{3f}$, $R^{3f1}$, $R^{3f2}$, $R^{3g}$ and $R^{3g1}$ are each independently hydrogen, halogen, —$OR^{a5}$, or substituted or unsubstituted $C_{1-6}$ alkyl; wherein $R^{a5}$ is preferably hydrogen or $C_{1-6}$ alkyl; the substituent in the substituted $C_{1-6}$ alkyl is preferably selected from one or more of the following groups: deuterium or halogen; $R^2$ is hydrogen, $C_{1-6}$ alkyl or $C_{3-10}$ cycloalkyl; and
in ring B, $R^5$, $R^{51}$, $R^{5a}$, $R^{5a1}$, $R^{5a2}$, $R^{5b}$, $R^{5b1}$, $R^{5c}$, $R^{5c1}$, $R^{5c2}$, $R^{5d}$, $R^{5d1}$, $R^{5d2}$, $R^{5e}$, $R^{5e1}$, $R^{5e2}$, $R^7$, $R^8$, $R^9$, $R^{10}$, $R^{11}$, $R^{12}$ and $R^{13}$ are hydrogen; $R^6$, $R^{6a}$, $R^{6b}$, $R^{6c}$, $R^{6d}$ and, $R^{6e}$ are each independently hydrogen, halogen, substituted or unsubstituted $C_{1-6}$ alkyl, substituted or unsubstituted $C_{2-8}$ heterocycloalkyl, substituted or unsubstituted $C_{6-20}$ aryl, substituted or unsubstituted $C_{2-10}$ heteroaryl, —$OR^{61}$, —$SR^{62}$, —$C(O)R^{65}$, —$C(O)OR^{66}$ or —$C(O)NR^{a69}R^{a610}$; $R^{61}$, $R^{62}$, $R^{65}$, $R^{66}$, $R^{a69}$ and, $R^{a610}$ are as defined above; substituents in the substituted $C_{1-6}$ alkyl, substituted $C_{2-8}$ heterocycloalkyl, substituted $C_{6-20}$ aryl or substituted $C_{2-11}$) heteroaryl are as defined above.

In a preferred embodiment of the present invention,
in ring Q, $R^{q1}$, $R^{q2}$, $R^{q3}$, $R^{q4}$, $R^{q5}$, $R^{q6}$, $R^{q7}$, $R^{q8}$, $R^{q9}$, $R^{q10}$, $R^{q11}$, $R^{q12}$, $R^{q13}$, $R^{q14}$, $R^{q15}$, $R^{q16}$, $R^{q17}$, $R^{q18}$, $R^{q19}$, $R^{q20}$, $R^{q21}$ and $R^{q22}$ are hydrogen or $C_{1-6}$ alkyl;
in ring A, $R^3$, $R^{31}$, $R^{32}$, $R^{33}$, $R^{3a}$, $R^{3a1}$, $R^{3b}$, $R^{3b1}$, $R^{3c}$, $R^{3c1}$, $R^{3c2}$, $R^{3d}$, $R^{3d1}$, $R^{3d2}$, $R^{3e}$, $R^{3e1}$, $R^{3f}$, $R^{3f1}$, $R^{3f2}$, $R^{3g}$ and $R^{3g1}$ are each independently hydrogen, $C_{1-6}$ alkyl or halogen substituted $C_{1-6}$ alkyl; the number of halogen is one or more than one (for example, 1-6; such as 1-3); $R^2$ is hydrogen, $C_{1-6}$ alkyl or $C_{3-10}$ cycloalkyl; and in ring B, $R^5$, $R^{51}$, $R^{5a}$, $R^{5a1}$, $R^{5a2}$, $R^{5b}$, $R^{5b1}$, $R^{5c}$, $R^{5c1}$, $R^{5c2}$, $R^{5d}$, $R^{5d1}$, $R^{5d2}$, $R^{5e}$, $R^{5e1}$, $R^{5e2}$, $R^7$, $R^8$, $R^9$, $R^{10}$, $R^{11}$, $R^{12}$ and $R^{13}$ are hydrogen; $R^6$, $R^{6a}$, $R^{6b}$, $R^{6c}$, $R^{6d}$ and $R^{6e}$ are each independently hydrogen, halogen, —C(O)$R^{65}$, or —C(O)NR$^{a69}$R$^{a610}$; $R^{66}$, $R^{a69}$ and $R^{a610}$ are as defined above; preferably, $R^{66}$ is hydrogen or $C_{1-6}$ alkyl; $R^{a69}$ and $R^{a610}$ are independently hydrogen or $C_{1-6}$ alkyl.

In a preferred embodiment of the present invention, ring Q is

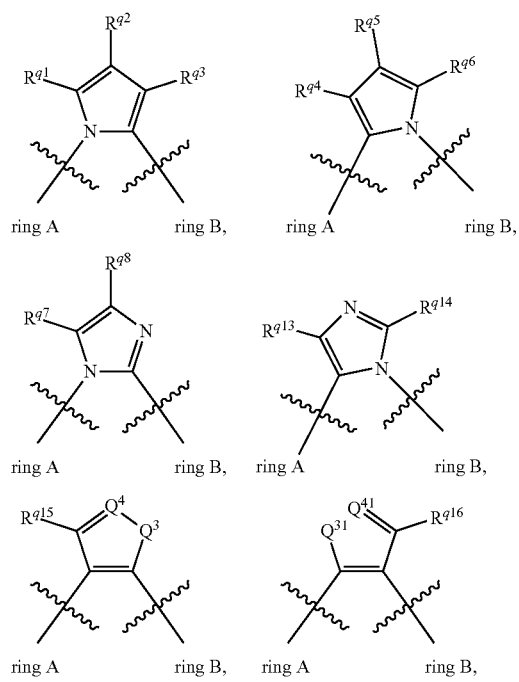

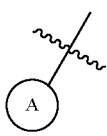

$R^{q1}$, $R^{q2}$, $R^{q3}$, $R^{q4}$, $R^{q5}$, $R^{q6}$, $R^{q7}$, $R^{q8}$, $R^{q13}$, $R^{q14}$, $R^{q15}$, $R^{q16}$, $R^{q17}$, $R^{q18}$, $R^{q19}$, $R^{q20}$, $R^{q21}$ and $R^{q22}$ are as defined above.

is

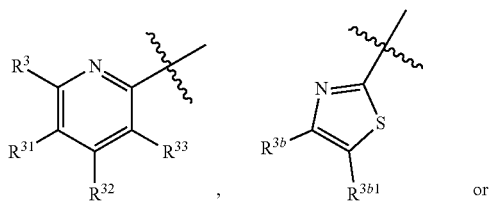

$R^3$, $R^{31}$, $R^{32}$, $R^{33}$, $R^{3b}$, $R^{3b1}$, $R^{3e}$, $R^{3e1}$ and $R^2$ are as defined above; and

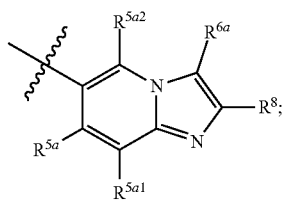

is

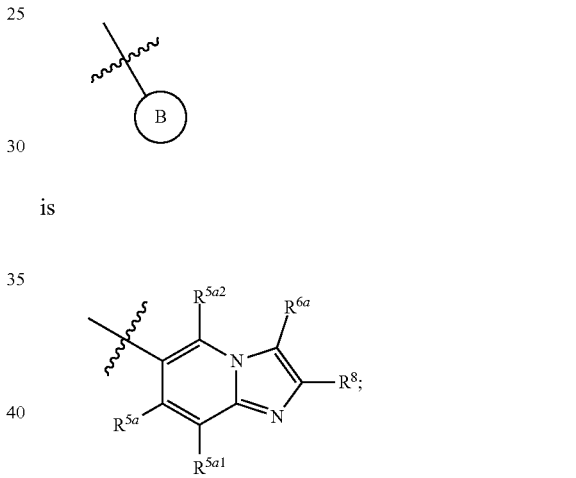

$R^{5a}$, $R^{5a1}$, $R^{5a2}$, $R^{6a}$ and $R^8$ are as defined above.

In a preferred embodiment of the present invention, ring Q is

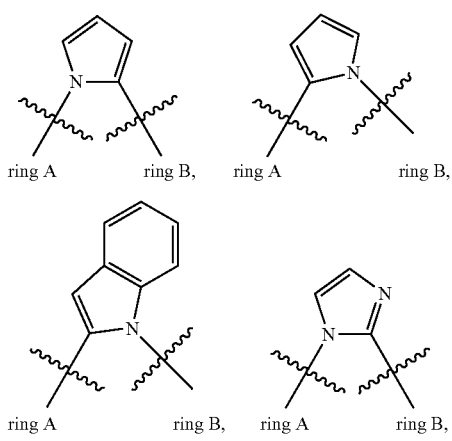

-continued
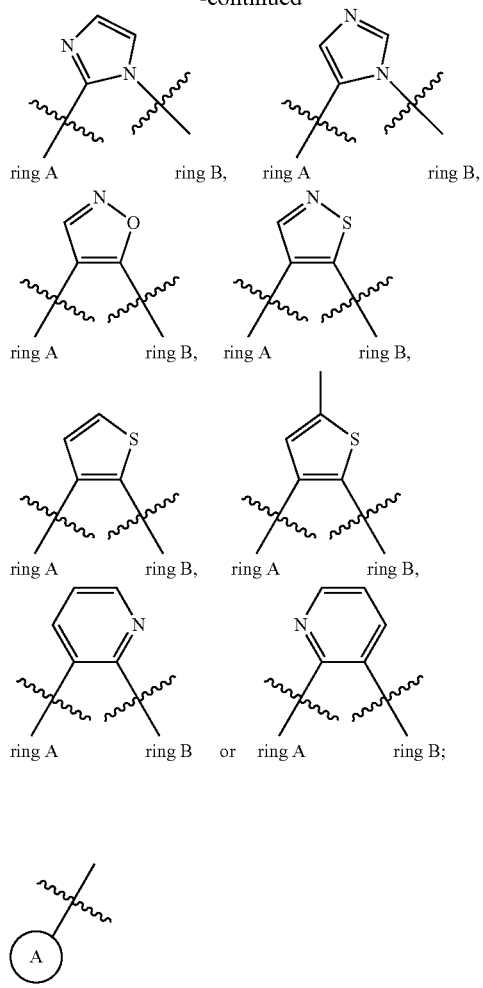
is
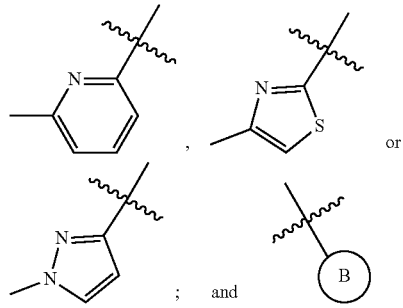
; and
is
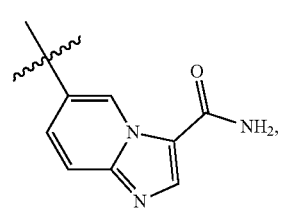
-continued
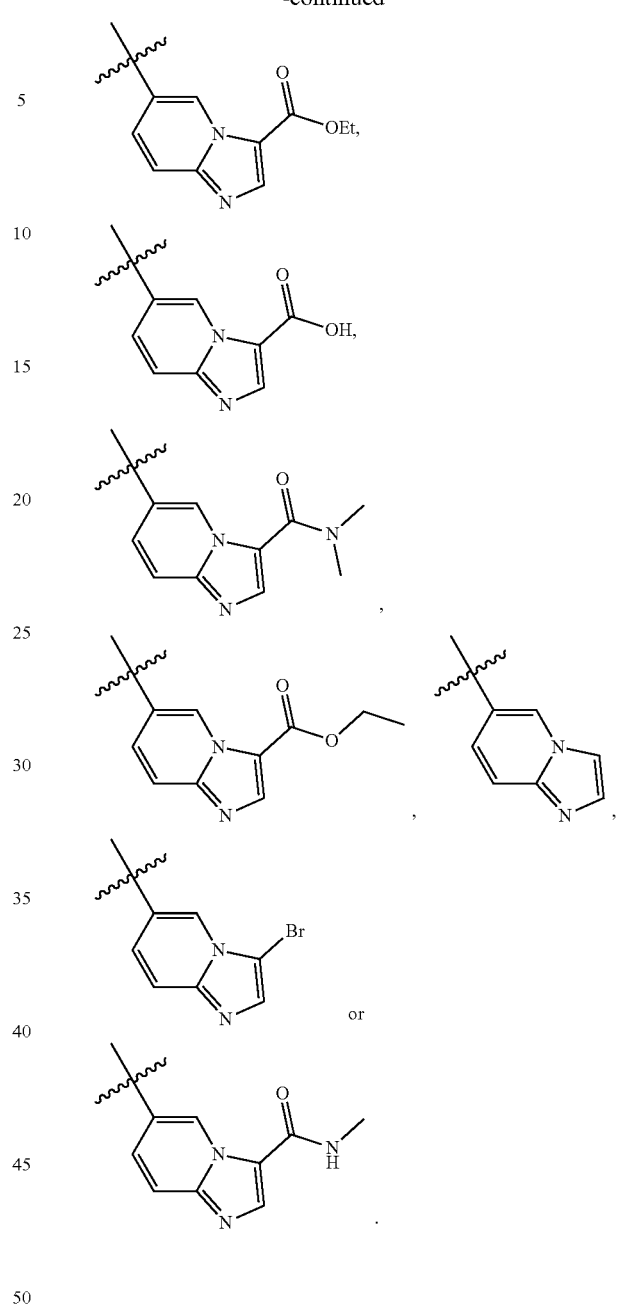
The aromatic heterocyclic compound represented by the general formula I is preferably selected from any one of the following compounds:
1
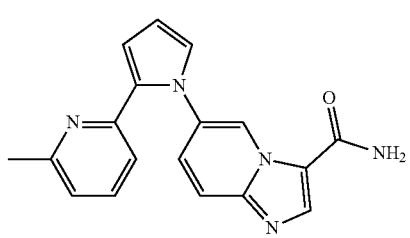

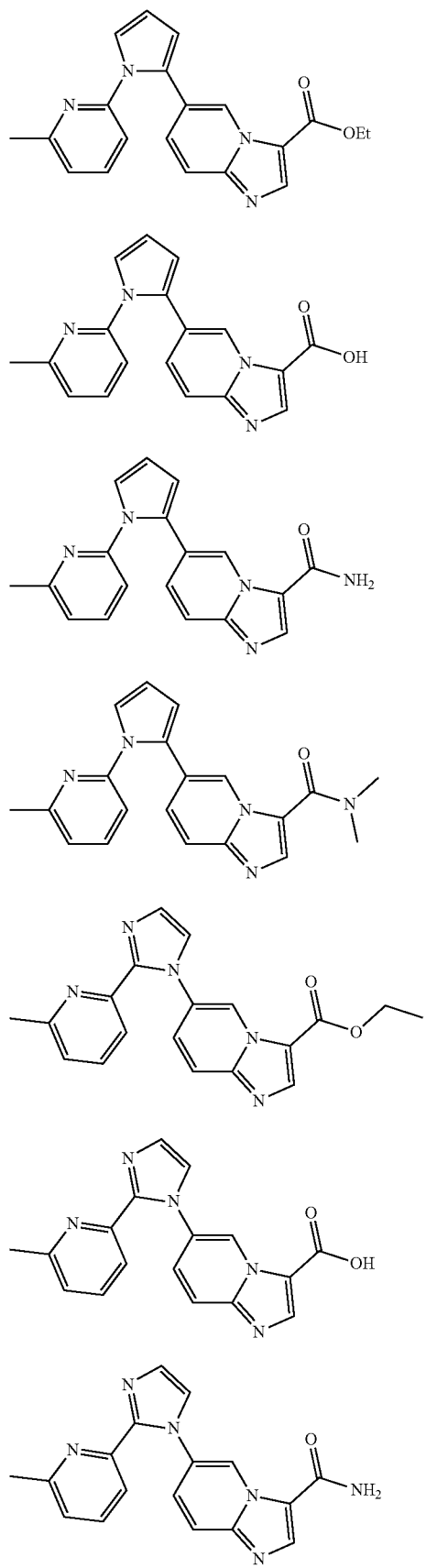
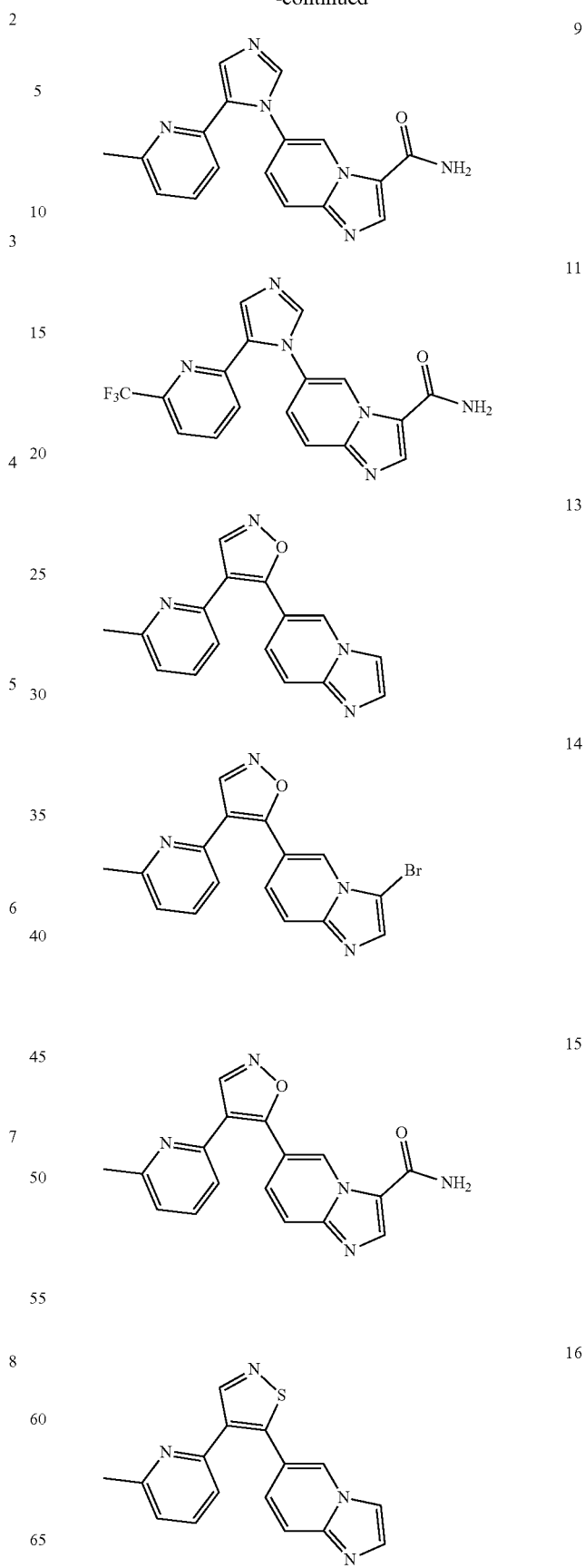

17

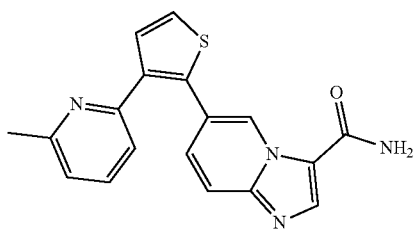

18

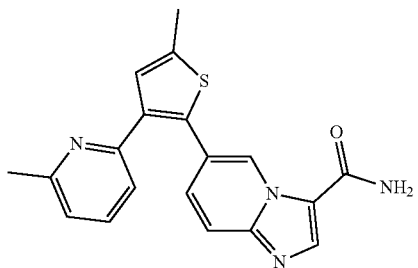

19

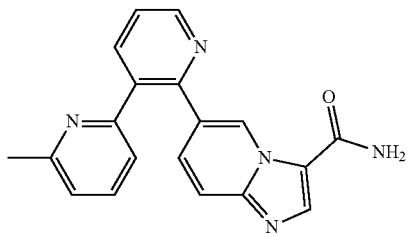

20

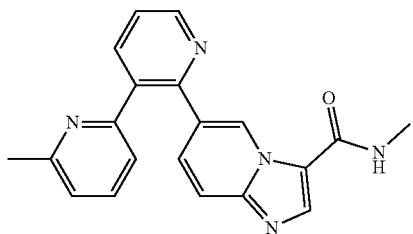

21

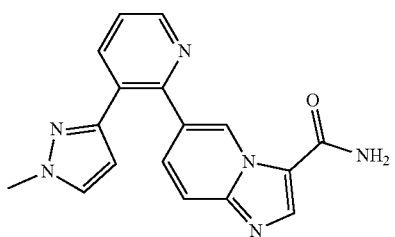

22

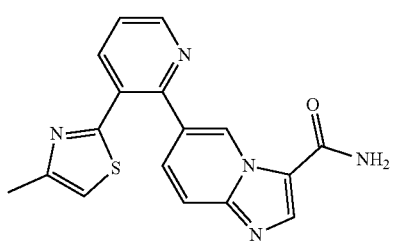

23

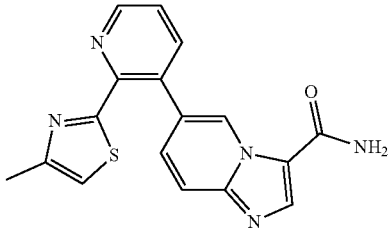

24

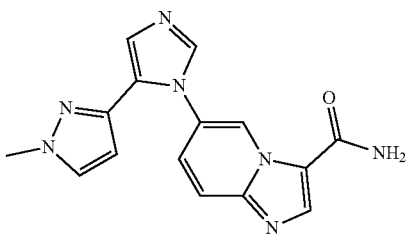

25

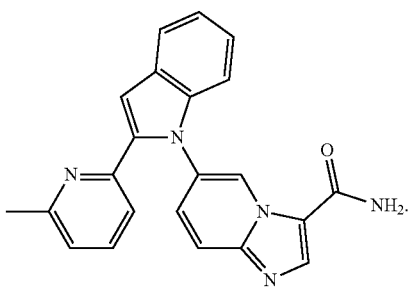

The aromatic heterocyclic compound represented by the general formula I and/or the pharmaceutically acceptable salt thereof of the present invention can be synthesized by known methods using commercially available raw materials.

The present invention also provides a method for preparing the aromatic heterocyclic compound represented by general formula I, which comprises the following steps: coupling compound I-A and compound I-B to obtain the aromatic heterocyclic compound represented by general formula I;

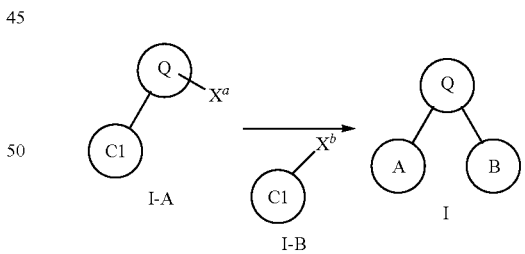

wherein, one of $X^a$ and $X^b$ is H, and the other is halogen, such as Cl, Br or I; in this case, $X^a$ is preferably hydrogen on the carbon atom between two nitrogen atoms in the imidazole ring;

or, one of $X^a$ and $X^b$ is an organotin reagent such as tri-n-butyltin reagent or an organoboron reagent such as boric acid, pinacol borate, etc., and the other is halogen, such as Cl, Br or I;

or one of $X^a$ and $X^b$ is —OPG1, and PG1 is groups like p-toluenesulfonyl or methanesulfonyl; and the other is organotin reagent such as tri-n-butyltin reagent or an organoboron reagent such as boric acid, pinacol borate, etc.;

one of ring C1 and ring C2 is ring A, and the other is ring B; ring A, ring B and ring Q are as defined above.

When ring Q is

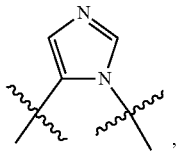 [SMILES: *c1cncn1*]

then it can be further prepared by the following method, which comprises the following steps: conducting a cyclization reaction on compound III-1 to obtain an aromatic heterocyclic compound represented by the general formula III;

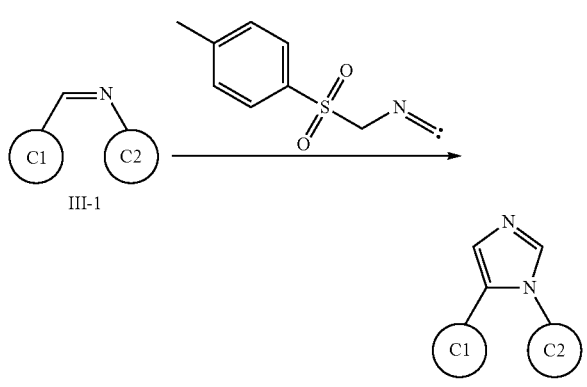

one of ring C1 and ring C2 is ring A, and the other is ring B; ring A and ring B are as defined above.

When ring Q is

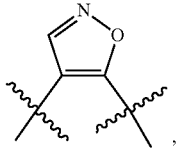 [SMILES: *c1cnoc1*]

then it can also be prepared by the following method, which comprises the following steps: conducting a cyclization reaction on compound VI-1 to obtain an aromatic heterocyclic compound represented by the general formula VI;

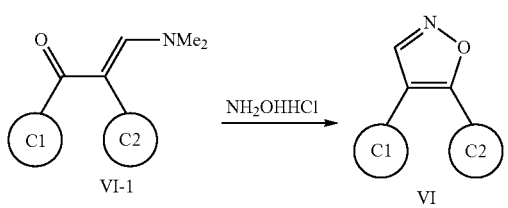

one of ring C1 and ring C2 is ring A, and the other is ring B; ring A and ring B are as defined above.

When ring Q is

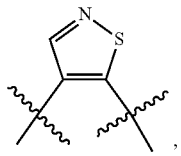 [SMILES: *c1cnsc1*]

then it can also be prepared by the following method, which comprises the following steps: conducting a cyclization reaction on compound V-1 to obtain an aromatic heterocyclic compound represented by the general formula V;

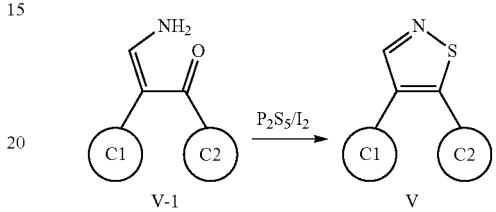

one of ring C1 and ring C2 is ring A, and the other is ring B; ring A and ring B are as defined above.

Wherein, some compounds can be synthesized by the method of route 1, which comprises the following steps: coupling N-boc-2-prryoleboronic acid with compound 1-4 to obtain compound 1-3, removing the boc from compound 1-3 to obtain compound I-1, then coupling compound I-1 with compound 1-2 to obtain an aromatic heterocyclic compound represented by formula I.

Synthetic Route 1:

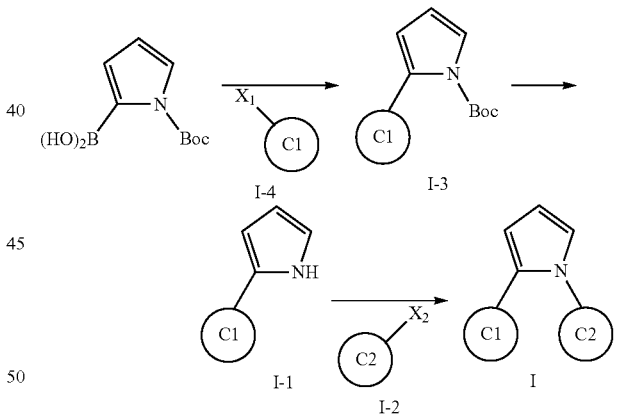

wherein, $X_1$ and $X_2$ are Cl, Br or I. When ring C1 is ring A, then ring C2 is ring B; or when ring C1 is ring B, then ring C2 is ring A. Ring A and ring B are as defined above.

For example:

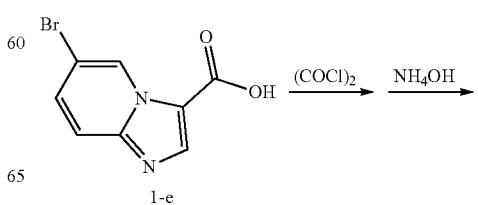

-continued

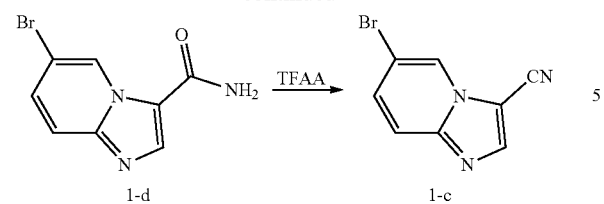

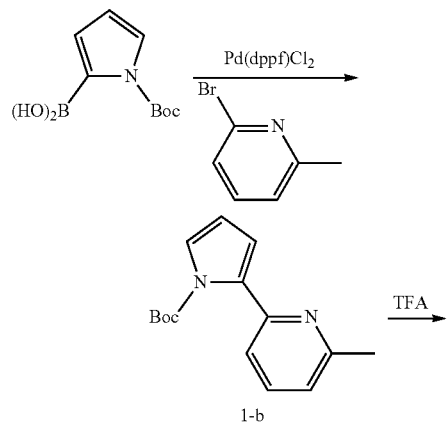

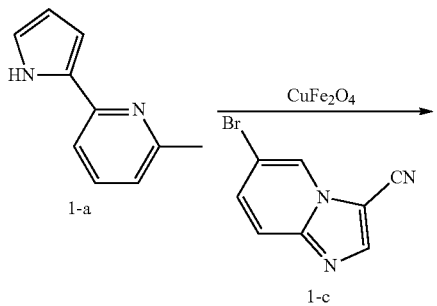

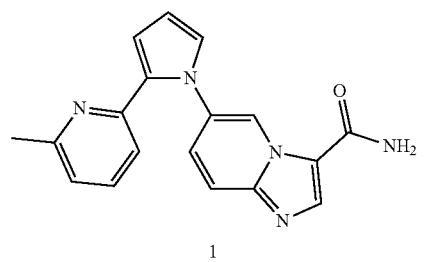

1

Other compounds can be synthesized by the method of route 2, which comprises the following steps: reacting compound imidazole with compound 1-4 in the presence of copper reagent to obtain compound II-1, and then coupling compound II-1 with compound 1-2 under the catalysis of palladium reagent to obtain compound II.

Synthetic Route 2:

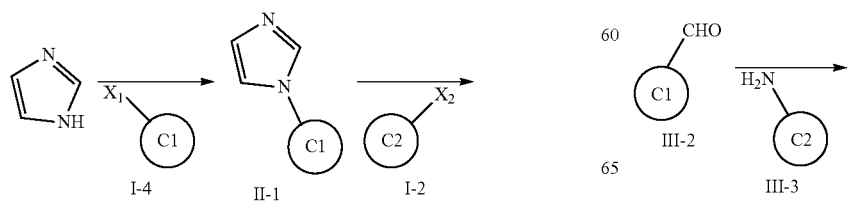

-continued

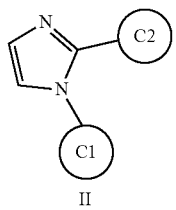

wherein, $X_1$ and $X_2$ are Cl, Br or I. When ring C1 is ring A, then ring C2 is ring B; or when ring C1 is ring B, then ring C2 is ring A. Ring A and ring B are as defined above.

For example:

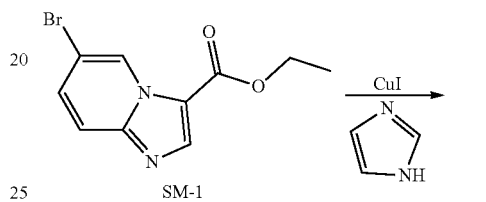

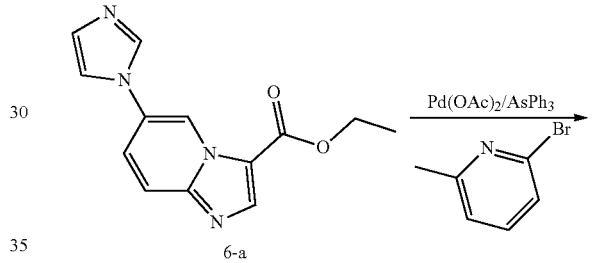

Other compounds are synthesized by the method of route 3, which comprises the following steps: reacting compound 111-2 with compound 111-3 in the presence of acid to obtain compound III-1, and then reacting compound III-1 with p-toluenesulfonylmethylisonitrile to obtain compound III Synthetic Route 3:

29

-continued

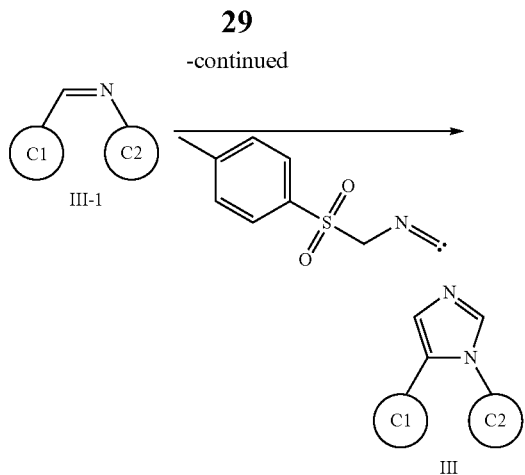

wherein, when ring C1 is ring A, then ring C2 is ring B; or when ring C1 is ring B, then ring C2 is ring A. Ring A and ring B are as defined above.

For example:

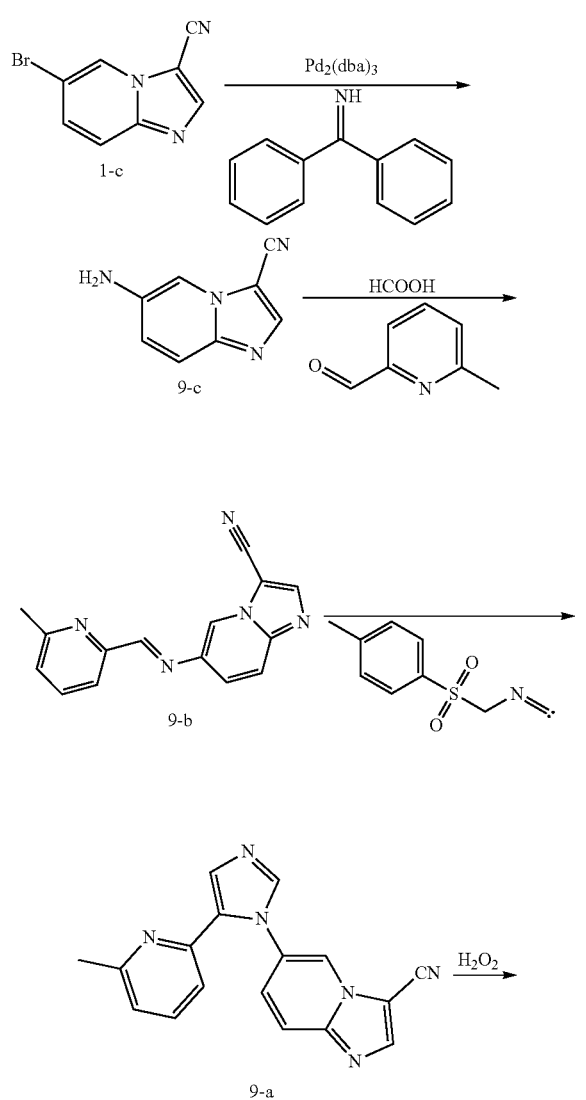

30

-continued

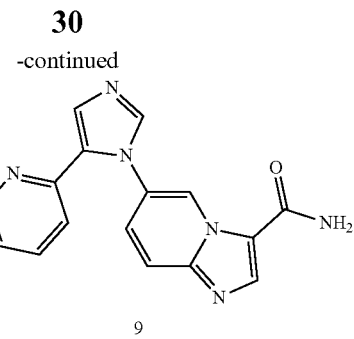

There are also some compounds synthesized by the method of route 4, which comprises the following steps: converting compound IV-5 to obtain compound IV-3, conducting a condensation reaction of compound IV-3 with compound IV-4 in the presence of strong base to obtain compound IV-2, and converting compound IV-2 to obtain compound IV-1, and which is further converted to obtain compound IV.

Synthetic Route 4:

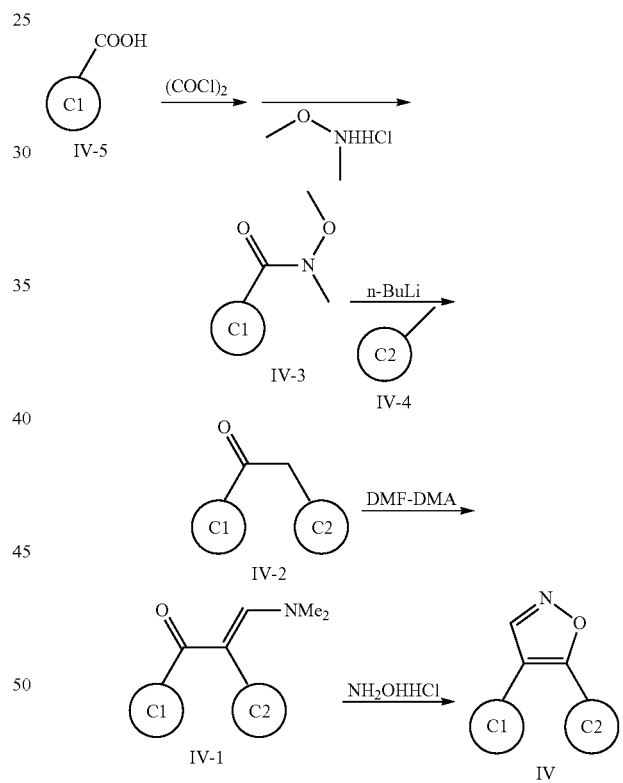

wherein, ring C2 is ring B; or when ring C1 is ring B, then ring C2 is ring A. Ring A and ring B are as defined above.

For example:

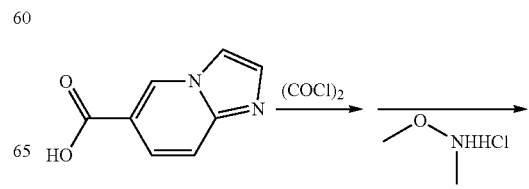

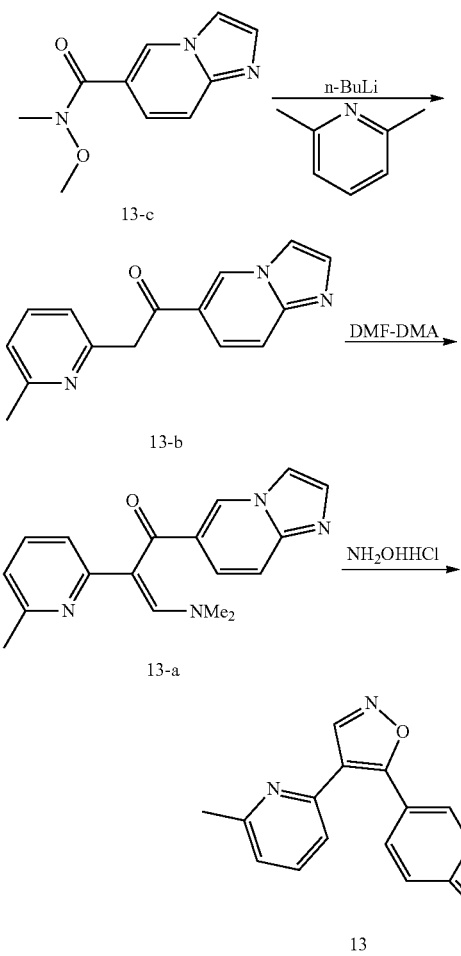

Compound IV can be further converted to compound V according to the following synthetic route 5, which comprises the following steps: hydrogenolyzing compound IV to obtain compound V-1, and converting compound V-1 to obtain compound V.

Synthetic Route 5:

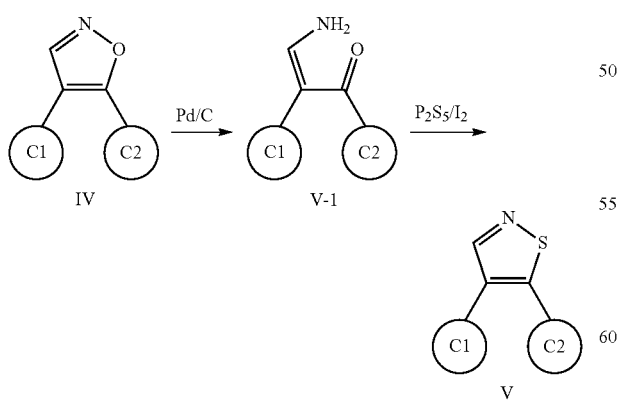

wherein, when ring C1 is ring A, then ring C2 is ring B; or when ring C1 is ring B, then ring C2 is ring A. Ring A and ring B are as defined above.

For example:

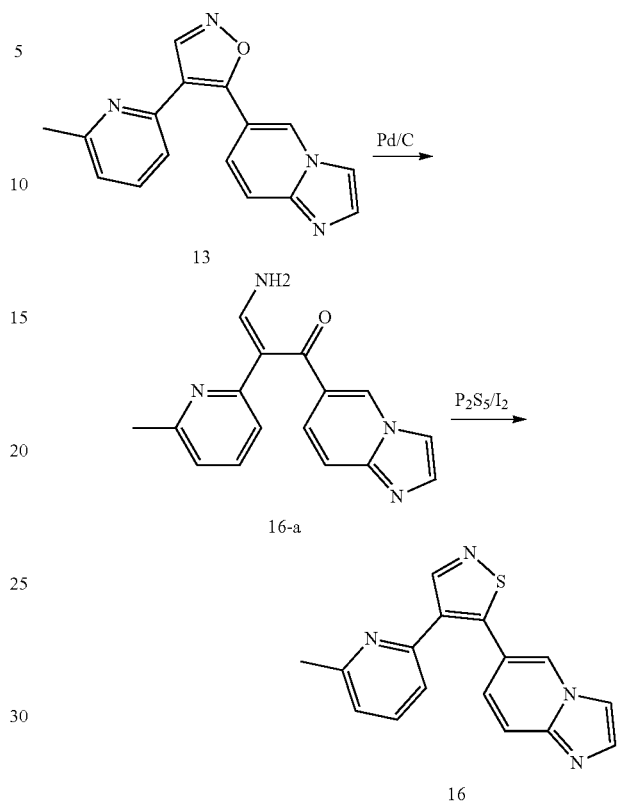

There are also some compounds synthesized by the method of route 6, which comprises the following steps: coupling compound VI-3 with compound VI-4 in the presence of palladium reagent to obtain compound VI-1, and then further coupling compound VI-1 with compound VI-2 in the presence of palladium reagent to obtain compound VI.

Synthetic Route 6:

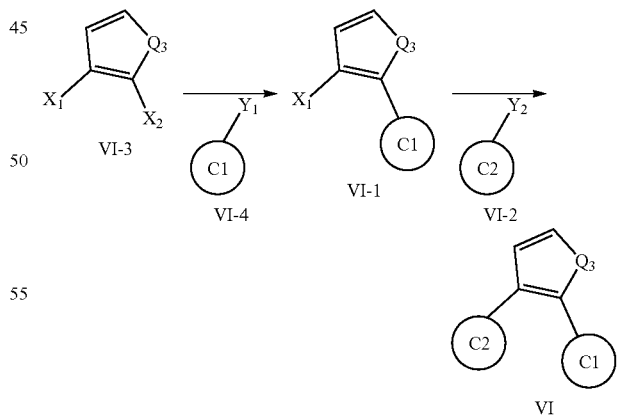

wherein, $X_1$ and $X_2$ are Cl, Br or I. When ring C1 is ring A, then ring C2 is ring B; or when ring C1 is ring B, then ring C2 is ring A. Ring A and ring B are as defined above. $Y_1$ and $Y_2$ are independently organotin reagents such as tri-n-butyltin reagent or organoboron reagents such as boric acid, pinacol borate and the like.

For example:

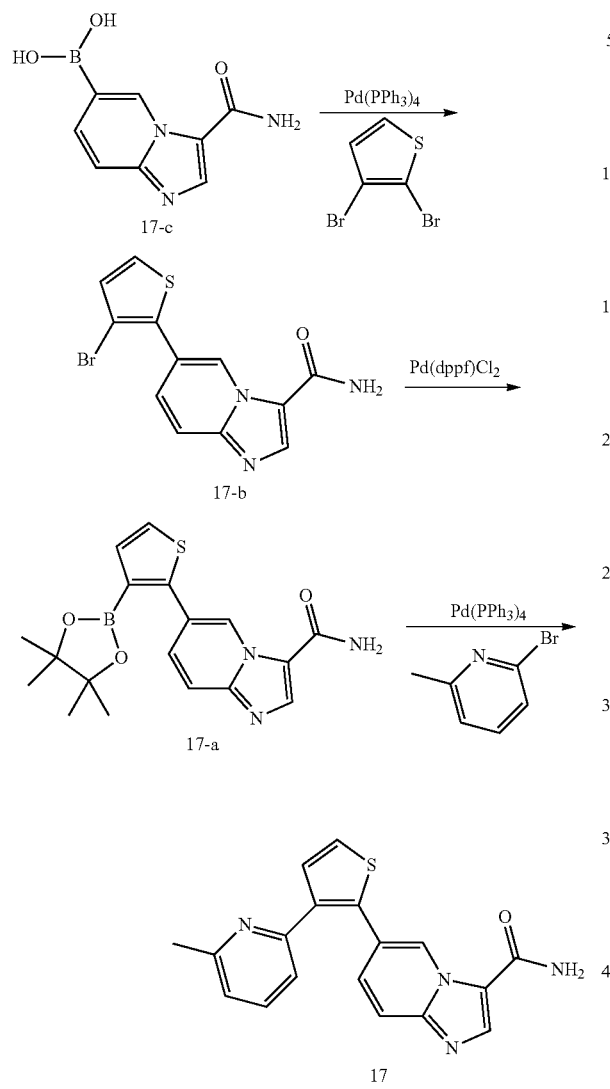

There are also some compounds synthesized by the method of route 7, which comprises the following steps: coupling compound VII-3 with compound VI-4 in the presence of palladium reagent to obtain compound VII-2, converting compound VII-2 to obtain compound VII-1, then coupling compound VII-1 with compound VI-2 in the presence of palladium reagent to obtain compound VII.

Synthetic Route 7:

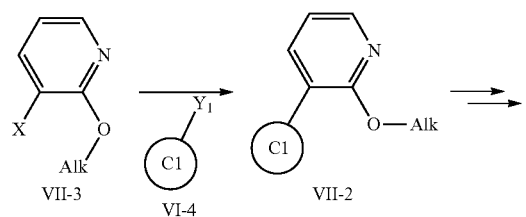

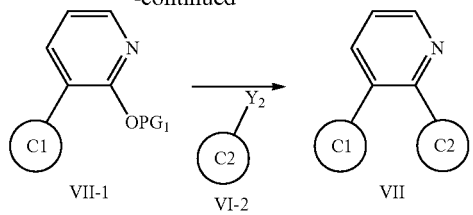

wherein, X is Cl, Br or I. When ring C1 is ring A, then ring C2 is ring B; or when ring C1 is ring B, then ring C2 is ring A. Ring A and ring B are as defined above. $Y_1$ and $Y_2$ are independently organotin reagents such as tri-n-butyltin reagent or organoboron reagents such as boric acid, pinacol borate and the like. Alk is $C_{1-6}$ alkyl. $PG_1$ is a group such as p-toluenesulfonyl and methanesulfonyl.

For example:

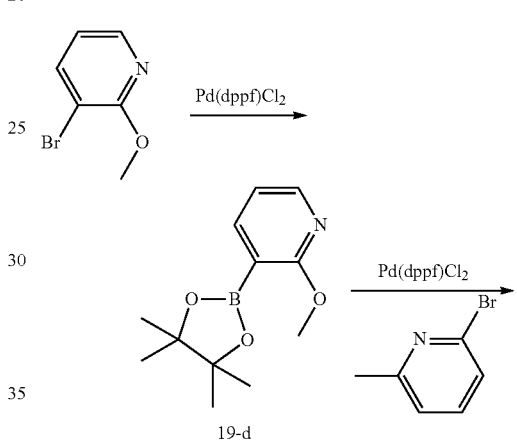

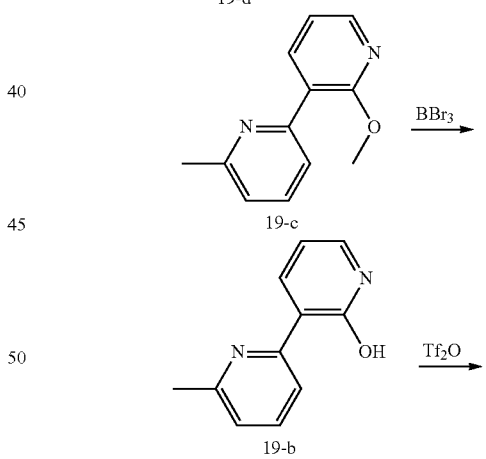

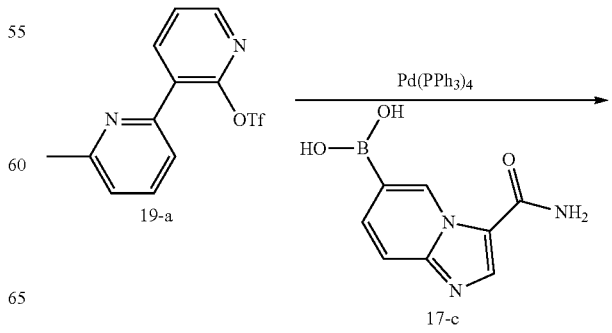

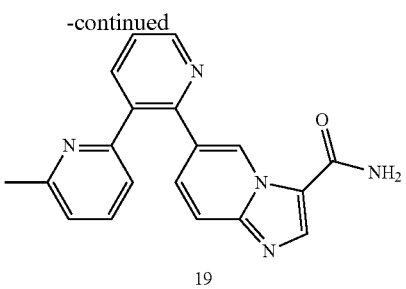

19

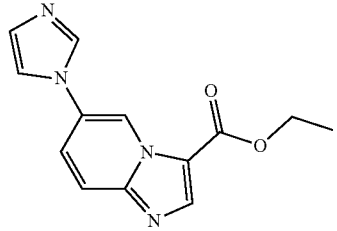

6-a

The conditions and steps used in the chemical reactions involved in the various reaction routes of the present invention can be carried out with reference to the conventional conditions and steps of such reactions in the art, and those literatures can be referred to for details: R. Larock, *Comprehensive Organic Transformations*, VCH Publishers (1989); T. W. Greene and P. G. M. Wuts, *Protective Groups in Organic Synthesis*, 3$^{rd}$ ED., John Wiley and Sons (1999); L. Fieser and M. Fieser, *Fieser and Fieser's Reagents for Organic Synthesis*, John Wiley and Sons (1994); L. Paquette, ed., *Encyclopedia of Reagents for Organic Synthesis*, John Wiley and Sons (1995) and subsequent editions thereof. The present application cites the entire contents of the above literatures. In addition, other target compounds of the present invention can be obtained by further modifying the peripheral positions of the compound obtained by the above methods with reference to the related method of the above literatures.

At least one aromatic heterocyclic compound prepared according to the above methods or a pharmaceutically acceptable salt thereof can be purified by column chromatography, high performance liquid chromatography, crystallization or other proper conditions. The conditions and steps of the purification methods such as column chromatography, high performance liquid chromatography and crystallization can be selected according to the conventional conditions and steps in the art.

The present invention also provides an intermediate compound for preparing the aromatic heterocyclic compound represented by general formula I, which is any of the following compounds:

2-b

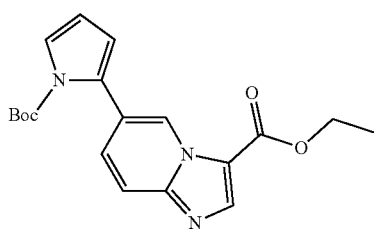

2-a

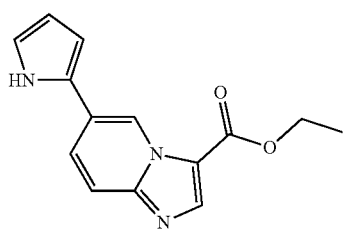

9-b 9-a 10-a 13-b 13-a

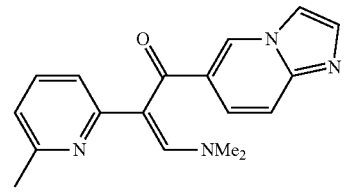

17-a

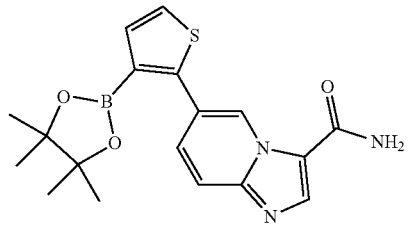

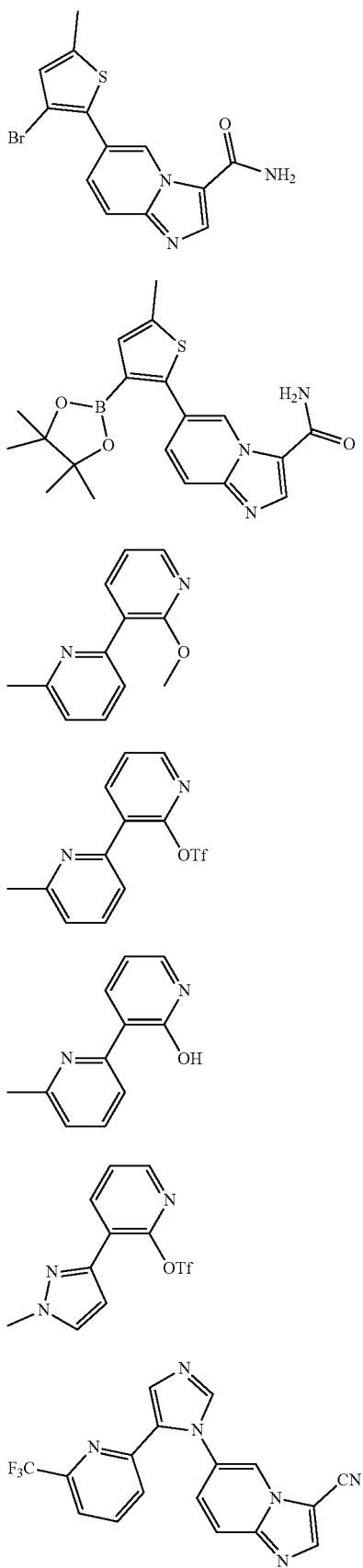
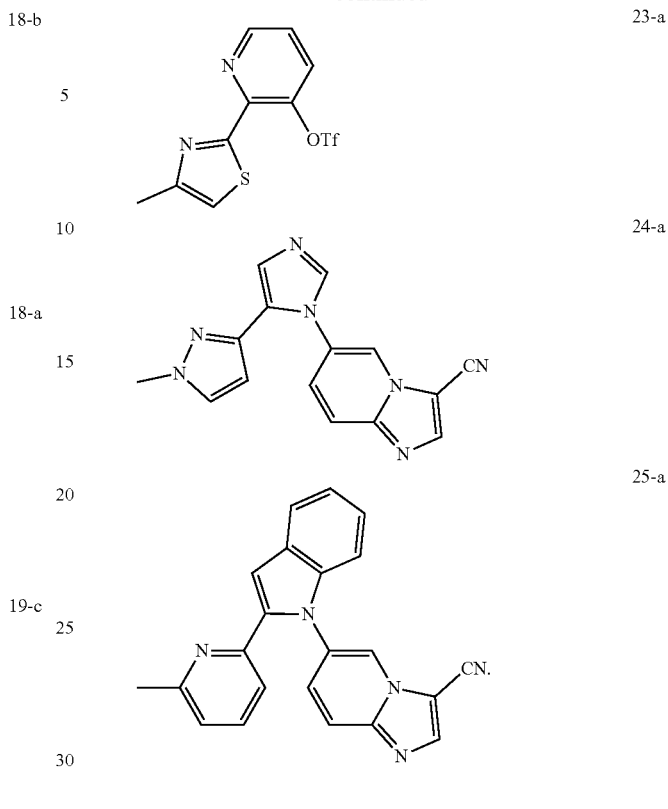

The compounds described herein comprise, but are not limited to, their optical isomers, racemates, and other mixtures. In these cases, single enantiomers or diastereomers, such as optically active structures, can be obtained by asymmetric synthesis or resolution from racemic mixtures or diastereomer mixtures. For the resolution of racemic mixtures or diastereomeric mixtures, they can be separated by traditional methods, such as crystallization using a resolution reagent; or they can be separated by chromatography. For example, chiral high performance liquid chromatography (HPLC) columns. In addition, such compounds comprise Z- and S-types (or cis- and trans-type) compounds containing C═C double bonds. The compounds described herein exist in various tautomers, and the term "compound" includes all tautomeric forms of the compound. The compounds herein also comprise their different crystal forms, including polycrystals and clathrates. Similarly, the term "salt" also includes all isomers of the compound. Racemates, other mixtures, Z- and E-types, tautomers and crystal forms.

The present invention also provides a use of the aromatic heterocyclic compound represented by the general formula I or the pharmaceutically acceptable salt thereof in the manufacture of an ALK5 inhibitor or in the manufacture of a medicament for the treatment and/or prevention ALK5-mediated diseases.

The "ALK5-mediated diseases" include but are not limited to: one or more of cancer, organ fibrosis, viral infection, chronic nephritis, acute nephritis, diabetic nephropathy, osteoporosis, arthritis, wound healing, ulcers, corneal trauma, heart valve stenosis, congestive heart necrosis, neurological impairment, Alzheimer's syndrome, peritoneal or subcutaneous adhesions, atherosclerosis and tumor metastasis growth, preferably cancer and/or organ fibrosis. The cancer includes but is not limited to colon cancer, pancreatic cancer, breast cancer, prostate cancer, lung cancer, brain cancer, ovarian cancer, cervical cancer, testicular cancer, renal cancer, head or neck cancer, bone cancer, skin cancer, rectum cancer, liver cancer, colon cancer, esophageal cancer, gastric cancer, pancreatic cancer, thyroid cancer, bladder cancer, lymphoma, leukemia and melanoma. The organ fibrosis includes but is not limited to renal fibrosis, liver fibrosis and lung fibrosis.

The present invention also provides a pharmaceutical composition comprising one or more of the prophylactically and/or therapeutically effective dose of nitrogen-containing aromatic heterocyclic compound represented by general formula I and the pharmaceutically acceptable salt thereof, and a pharmaceutically acceptable carrier.

In the present invention, the "the prophylactically and/or therapeutically effective dose" refers to (i) an amount of the compounds of the present invention for preventing and/or treating the specific diseases or conditions described in this application, (ii) an amount of the compounds of the present invention that attenuates, improves or eliminates one or more of specific diseases or conditions described in this application, or (iii) an amount of the compounds of the present invention for preventing or delaying the onset of one or more symptoms of the specific diseases or disorders described in this application. The dose for treating human patients may be 0.0001 mg/kg-50 mg/kg, most usually 0.001 mg/kg-10 mg/kg body weight, for example in the range of 0.01 mg/kg-1 mg/kg. Such a dose may be administrated, for example, 1-5 times a day.

According to the therapeutic purpose, the pharmaceutical composition can be made into various types of unit dosage forms, such as tablets, pills, powders, liquids, suspensions, emulsions, granules, capsules, suppositories and injections (solutions and suspensions), etc., preferably tablets, pills, granules and capsules.

To shape the pharmaceutical composition in tablet form, any excipient known and widely used in the art may be applied. For example, carriers such as lactose, white sugar, sodium chloride, glucose, urea, starch, calcium carbonate, kaolin, crystalline cellulose, silicic acid, etc.; adhesive such as water, ethanol, propanol, ordinary syrup, glucose solution, starch solution, gelatin solution, carboxymethyl cellulose, shellac, methyl cellulose and potassium phosphate, polyvinylpyrrolidone, etc.; disintegrants, such as dry starch, sodium alginate, agar powder and kelp powder, sodium bicarbonate, calcium carbonate, fatty acid esters of polyethylene sorbitan, sodium lauryl sulfate, monoglyceryl stearate, starch and lactose, etc.; disintegration inhibitors such as white sugar, glycerol tristearate, coconut oil and hydrogenation oil; adsorption accelerators, such as quaternary ammonium base and sodium lauryl sulfate, etc.; wetting agents, such as glycerin, starch, etc.; adsorbents, such as starch, lactose, kaolin, bentonite and colloidal silicic acid, etc.; and lubricants, such as pure talc, stearate, boric acid powder and polyethylene glycol. Conventional coating materials can also be selected to make sugar-coated tablets, gelatin-coated tablets, enteric-coated tablets, coated tablets, double-layer tablets and multi-layer tablets as required.

In order to shape the pharmaceutical composition in the form of pills, any known and widely used excipients in the art can be applied, for example, carriers such as lactose, starch, coconut oil, hydrogenated vegetable oil, kaolin and talc, etc.; adhesive such as gum arabic powder, tragacanth powder, gelatin and ethanol, etc.; disintegrants, such as agar and kelp powder.

In order to shape the pharmaceutical composition in the form of suppositories, any excipient known and widely used in the art can be applied, for example, polyethylene glycol, coconut oil, higher alcohols, esters of higher alcohols, gelatin and semi-synthetic glycerides, etc.

In order to prepare a pharmaceutical composition in the form of an injection, the solution or suspension can be made into an injection that is isotonic with blood after sterilization (preferably adding an appropriate amount of sodium chloride, glucose or glycerol, etc.). When preparing an injection, any carrier conventionally used in the art may also be applied. For example, water, ethanol, propylene glycol, ethoxylated isostearyl alcohol, polyoxylated isostearyl alcohol and fatty acid esters of polyethylene sorbitan, etc. In addition, conventional dissolving agents, buffers and analgesics can also be added.

In the present invention, the administration method of the pharmaceutical composition is not particularly limited. According to the patient's age, gender and other conditions and symptoms, various formulations can be selected for administration. For example, tablets, pills, solutions, suspensions, emulsions, granules, or capsules can be administered orally; injections can be administered alone or mixed with injection delivery fluids (such as glucose solutions and amino acid solutions) for intravenous injection; suppositories are delivered to the rectum.

Unless otherwise stated, the following terms in the description and claims of the present invention have the following meanings:

A single dash, "-", or a double dash, "=" can be added before and/or after the term of the present invention, indicating a bond sequence of the bond between the named substituent and its parent part; a single dash indicates a single bond, a double dash indicates a double bond or a pair of single bonds in the case of spiro ring substituents. When there is no single dash or double dashes, a single bond can be considered to form between the substituent and its parent part. In addition, the substituent is read "from left to right" unless otherwise indicated. For example, $C_{1-6}$ alkoxycarbonyloxy and —OC(O)$C_{1-6}$ alkyl represent the same function; similarly, arylalkyl, arylalkyl-, and -alkylaryl represent the same function.

The term "alkyl" in the present invention refers to a branched and straight-chain saturated aliphatic hydrocarbon group including 1 to 6 carbon atoms, such as methyl, ethyl, n-propyl, isopropyl, n-butyl, t-butyl, isobutyl, pentyl, hexyl and their various isomers. In the present invention, the "$C_{x1-y1}$" alkyl(x1 and y1 are integers) with a defined carbon number range, such as "$C_{1-6}$ alkyl", has the same definition except that the carbon number range and the definition range of carbon number of "alkyl" in this paragraph is different. When the "alkyl" serves as a linking group between two other groups, it may be linear or branched, examples include but are not limited to —$CH_2$—, —$CH_2CH_2$—, —$CH_2CH_2CHC(CH_3)$— and —$CH_2CH_2(CH_2CH_3)CH_2$—.

The term "cycloalkyl" in the present invention refers to monocyclic or bicyclic cycloalkyl. Monocyclic cycloalkyl is a cyclic hydrocarbon group containing 3 to 10 carbon atoms. These groups may be saturated or unsaturated, but are not aromatic. In certain embodiments, the cycloalkyl group is fully saturated. Bicyclic cycloalkyl is a bridged monocyclic cycloalkyl or fused bicyclic cycloalkyl. The bridged monocyclic cycloalkyl contains a monocyclic cycloalkyl ring, in which two non-adjacent carbon atoms of the monocyclic cycloalkyl ring are connected by an alkylene bridge between one to three additional carbon atoms (ie, bridged group of —($CH_2$)— form, where w is 1, 2 or 3). The fused bicyclic cycloalkyl group includes a monocyclic cycloalkyl ring fused to a phenyl, a monocyclic cycloalkyl, a monocyclic cycloalkenyl, a monocyclic heterocyclyl, or a monocyclic heteroaryl. The bridged or fused bicyclic cycloalkyl is connected to the parent molecular moiety through any carbon atom contained in the monocyclic cycloalkyl ring. Cycloalkyl may be optionally substituted with one or two groups as independent oxo or thio.

In the present invention, the term "cycloalkenyl" refers to monocyclic or bicyclic cycloalkenyl. Monocyclic cycloalkenyl are cyclic hydrocarbon groups containing 3 to 8 carbon atoms, which are unsaturated (ie, contain at least one cyclic carbon-carbon double bond) but are not aromatic. The bicyclic cycloalkenyl ring is a bridged monocyclic ring or a fused bicyclic ring. The bridged monocyclic ring contains a monocyclic cycloalkenyl ring in which two non-adjacent carbon atoms of the monocyclic ring are connected by an alkylene bridge between one to three additional carbon atoms (i.e., bridged group in the form of —(CH$_2$) where w is 1, 2 or 3). The fused bicyclic cycloalkenyl ring system includes a monocyclic cycloalkenyl ring fused to a phenyl, a monocyclic cycloalkyl, a monocyclic cycloalkenyl, a monocyclic heterocyclyl, or a monocyclic heteroaryl. The bridged or fused bicyclic cycloalkenyl is connected to the parent molecular moiety through any carbon atom contained in the monocyclic cycloalkenyl ring. The cycloalkenyl group can be optionally substituted with one or two groups as independent oxo or thio.

In the present invention, the term "alkoxy" refers to a cyclic or acyclic alkyl having the number of carbon atoms connected by an oxygen bridge. Thus, "alkoxy" includes the above definitions of alkyl and cycloalkyl.

In the present invention, the term "alkylthio" refers to a cyclic or acyclic alkyl having the number of carbon atoms connected by a sulfur bridge. Thus, "alkylthio" includes the above definitions of alkyl and cycloalkyl.

In the present invention, the term "alkenyl" refers to a linear, branched or cyclic non-aromatic hydrocarbon group containing a specified number of carbon atoms and at least one carbon-carbon double bond. There is preferably one carbon-carbon double bond, and up to four non-aromatic carbon-carbon double bonds may be present. Thus, "C$_{2-8}$ alkenyl" refers to an alkenyl group having 2-8 carbon atoms. The straight chain, branched chain or ring portion of the alkenyl group may contain a double bond, and if it is indicated as a substituted alkenyl group, it may be substituted.

In the present invention, the term "alkynyl" refers to a linear, branched or cyclic hydrocarbon group containing a specified number of carbon atoms and at least one carbon-carbon triple bond. There can be up to three carbon-carbon triple bonds. Thus, "C$_{2-8}$ alkynyl" refers to an alkynyl group having 2-8 carbon atoms. "C$_{2-6}$ alkynyl" refers to an alkynyl group having 2 to 6 carbon atoms.

In the present invention, the term "aryl" refers to a monocyclic aryl or aromatic bicyclic ring system containing at least one benzene ring or a bicyclic ring system containing only carbon atoms. The bicyclic aryl may be a phenyl fused to a monocyclic cycloalkyl, a monocyclic cycloalkenyl or a monocyclic heterocyclic. The bicyclic aryl is attached to the parent molecule through any carbon atom contained in the phenyl portion of the bicyclic system or any carbon atom contained in a naphthyl or azulenyl. The fused monocyclic cycloalkyl or monocyclic heterocyclyl portion of the bicyclic aryl group can be optionally substituted with one or two oxo and/or thio. In certain embodiments, the bicyclic aryl group is fused to (i) naphthyl or (ii) phenyl ring of a 5-membered or 6-membered monocyclic cycloalkyl, a 5-membered or 6-membered monocyclic cycloalkenyl, or a 5-membered or 6-membered monocyclic heterocyclyl, where the fused cycloalkyl, the fused cycloalkenyl and the fused heterocyclyl can be optionally substituted with one or two groups which are independent oxo or thio.

In the present invention, the term "cyano" refers to —CN.

In the present invention, the term "carboxy" refers to —COOH.

In the present invention, the term "sulfonic acid group" refers to —SOOOH.

In the present invention, the term "halogen" refers to fluorine, chlorine, bromine or iodine.

In the present invention, the term "heteroaryl" refers to a monocyclic heteroaryl or bicyclic ring system containing at least one heteroaryl ring. The monocyclic heteroaryl group may be a 5-membered or 6-membered ring. The 5-membered ring is composed of two double bonds and one, two, three or four nitrogen atoms and one oxygen atom or sulfur atom. The 6-membered ring is composed of three double bonds and one, two, three or four nitrogen atoms. The 5-membered or 6-membered heteroaryl group is connected to the parent molecule through any carbon atom or nitrogen atom contained in the heteroaryl group. The bicyclic heteroaryl group is composed of a monocyclic heteroaryl group fused to a phenyl, a monocyclic cycloalkyl, a monocyclic cycloalkenyl, a monocyclic heterocyclyl or a monocyclic heteroaryl. The cycloalkyl or heterocyclyl portion of the fused bicyclic heteroaryl can be optionally substituted with one or two groups which are independent oxo or thio. When the bicyclic heteroaryl contains a fused cycloalkyl, cycloalkenyl or heterocyclic ring, the bicyclic heteroaryl is connected to the parent molecule through any carbon or nitrogen atom contained in the monocyclic heteroaryl portion of the bicyclic system. When the bicyclic heteroaryl is a monocyclic heteroaryl fused to a benzene ring or a monocyclic heteroaryl, the bicyclic heteroaryl is connected to the parent molecule through any carbon atom or nitrogen atom in the bicyclic ring system. In certain embodiments, the fused bicyclic heteroaryl is that a 5- or 6-membered monocyclic heteroaromatic ring fused to a phenyl, a 5- or 6-membered monocyclic cycloalkyl, a 5- or 6-membered monocyclic cycloalkenyl, a 5- or 6-membered monocyclic heterocyclyl or 5- or 6-membered monocyclic heteroaryl, wherein the fused cycloalkyl, cycloalkenyl and heterocyclyl may be optionally substituted with one or two groups which are independent oxo or thio.

In the present invention, the term "heterocyclyl" or "heterocycle" refers to a monocyclic heterocycle or a bicyclic heterocycle. The monocyclic heterocycle is a 3, 4, 5, 6 or 7-membered ring containing at least one heteroatom selected from O, N and S, wherein the ring is saturated or unsaturated, but not aromatic. The monocyclic heterocycle is connected to the parent molecule through any carbon atom or nitrogen atom contained in the monocyclic heterocycle. The bicyclic heterocycle is a monocyclic heterocycle fused to a phenyl, a monocyclic cycloalkyl, a monocyclic cycloalkenyl, a monocyclic heterocyclyl or a monocyclic heteroaryl. The bicyclic heterocyclic ring is connected to the parent molecule through any carbon or nitrogen atom contained in the monocyclic heterocyclyl portion of the bicyclic ring system. In certain embodiments, the bicyclic heterocyclyl is a 5- or 6-membered monocyclic heterocyclic ring fused to a phenly, a 5- or 6-membered monocyclic cycloalkyl, a 5- or 6-membered monocyclic cycloalkenyl, a 5- or 6-membered monocyclic heterocyclyl or a 5- or 6-membered monocyclic heteroaryl, wherein the bicyclic heterocyclic can be optionally substituted with one or two groups which are independent oxo or thio.

In the present invention, the term "hydroxyl" refers to —OH.

In the present invention, the term "nitro" refers to —NO2.

Any group contains one or more substituents, those skilled in the art can understand, but does not include unrealistically high steric hindrance, synthetically unfeasible and/or inherently unstable substituents.

In the present invention, the term "pharmaceutically acceptable salt" refers to pharmaceutically acceptable salt and solvate with acid or base. Such pharmaceutically acceptable salt includes, but is not limited to, salt with inorganic acid, such as hydrochloride, phosphate, diphosphate, hydrobromide, sulfate, sulfinate, nitrate, and the like; also includes salt with organic acid, such as malate, maleate, fumarate, tartrate, succinate, citrate, acetate, lactate, sulfonate, tosilate, 2-hydroxyethylsulfonate, benzoate, salicylate, stearate and alkanoate such as acetate, salt of HOOC—$(CH_2)_n$—COOH, where n is 0-4, and similar salts. Similarly, pharmaceutically acceptable cation includes but is not limited to sodium, potassium, calcium, aluminum, lithium and ammonium. Those skilled in the art can recognize various synthetic methods that may be used to prepare non-toxic pharmaceutically acceptable salt.

In the present invention, the "solvate" such as "hydrate" is formed by the interaction of the solvent and the compound. The term "compound" should include solvates of compounds (including hydrates of compounds). Similarly, "salt" also includes salt solvates (such as salt hydrates). Suitable solvates are pharmaceutically acceptable, such as hydrates, which include monohydrates and hemihydrates.

On the basis of not violating common knowledge in the art, the above-mentioned preferred conditions can be arbitrarily combined to obtain preferred examples of the present invention.

The reagents and raw materials used in the present invention are commercially available.

In the present invention, the room temperature refers to the ambient temperature, which is 10° C.–35° C.

The positive progress effects of the present invention are that the aromatic heterocyclic substituted olefin compound of the present invention is an ALK5 inhibitor, which can be used in the manufacture of a medicament for the treatment of diseases, such as cancer, renal fibrosis, liver fibrosis, pulmonary fibrosis, viral infection, chronic nephritis, acute nephritis, diabetic nephropathy, osteoporosis, arthritis, wound healing, ulcers, corneal trauma, heart valve stenosis, congestive heart necrosis, neurological impairment, Alzheimer's syndrome, peritoneal or subcutaneous adhesions, atherosclerosis and tumor metastasis growth.

DETAILED DESCRIPTION OF THE PREFERRED EMBODIMENT

The reagents and raw materials (except intermediates) used in the present invention are all obtained through commercial channels. The room temperature in the present invention refers to the ambient temperature, which is 10° C.–35° C. Overnight means 8-15 hours. Reflux refers to the reflux temperature of the solvent under normal pressure.

The following is a list of abbreviations used in the examples:
DMF N,N-dimethylformamide
DMSO dimethyl sulfoxide
DCM dichloromethane
THF tetrahydrofuran
MeOH methanol
PE petroleum ether
EA ethyl acetate
DME ethylene glycol dimethyl ether
$H_2O_2$ hydrogen peroxide
$Na_2CO_3$ sodium carbonate
NB S N-bromosuccinimide
$Pd(dppf)Cl_2$ [1,1'-bis(diphenylphosphino)ferrocene]palladium(II) dichloride dichloromethane complex
$Pd_2(dba)_3$ tridibenzylideneacetone dipalladium
BINAP (±)-2,2'-bis-(diphenylphosphino)-1,1'-binaphthalene
DMF-DMA N,N-dimethylformamide dimethyl acetal
DIBAL-H diisobutylaluminum hydride Synthetic Route of Compound 1

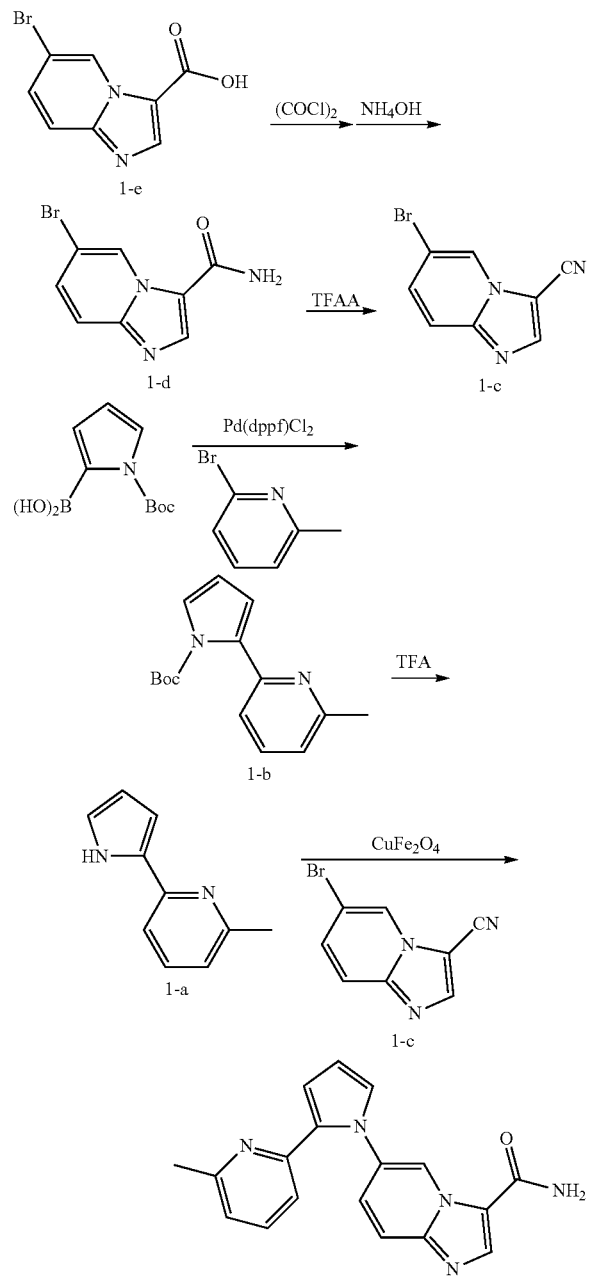

Synthesis of Compound 1-e

Compound 1-e was synthesized according to the method in WO2015/157093.

Synthesis of Compound 1-d 1-e (500 mg, 2.07 mmol) was dissolved in dichloromethane (10 mL). Under ice bath, oxalyl chloride (1 mL) and a drop of DMF were slowly added to the solution. The reactants were raised to room temperature and reacted for 60 minutes. The mixture was concentrated under reduced pressure and diluted with dichloromethane (5 mL). Under ice bath, the solution was slowly added dropwise to ammonia water (5 mL), and the reaction mixture reacted at 0° C. for 10 minutes, and then raised to room temperature and stirred overnight. The liquid was separated, and the aqueous layer was extracted with dichloromethane. The combined organic phases were washed successively with water and brine, dried over anhydrous sodium sulfate, and concentrated to obtain compound 1-d (300 mg, 60%) as a white solid. LC-MS (ESI): m/z=239.9 [M+H]$^+$.

Synthesis of Compound 1-c 1-d (100 mg, 0.42 mmol) was dissolved in dioxane (10 mL). Under ice bath, pyridine (0.34 mL, 4.2 mmol) was added to the solution. After stirring the solution for 5 minutes, trifluoroacetic anhydride (0.29 mL, 2.08 mmol) was slowly added dropwise. The reactants were raised to room temperature and stirred for 5 hours. After the reaction was completed, the reaction was quenched by the addition of water, and the organic solvent was removed by concentration under reduced pressure. The mixture was dissolved in ethyl acetate, washed successively with water and saturated brine, then dried over anhydrous sodium sulfate, and concentrated to obtain compound 1-c (80 mg, 86%) as a white solid. LC-MS (ESI): m/z=221.9 [M+H]$^+$.

Synthesis of Compound 1-b

1-Boc-2-pyrrole-boronic acid (1.11 g, 5.27 mmol), 2-bromo-6-methylpyridine (0.5 mL, 4.39 mmol), Pd(dppf)Cl$_2$ (359 mg, 0.44 mmol), sodium carbonate (1.16 g, 10.99 mmol), 1,4-dioxane (10 mL) and water (2 mL) were added to a reaction flask. The reaction solution was replaced with N$_2$ and reacted at 85° C. overnight. After the reaction was completed, the reaction solution was diluted with ethyl acetate, washed with water, then washed with saturated brine and dried over anhydrous sodium sulfate, then filtered and the filtrate was dried by rotary evaporation. The crude product was separated by silica gel column chromatography (PE:EA=3:1) to obtain compound 1-b (600 mg, 53%) as a white solid. LC-MS (ESI): m/z=259.1 [M+H]$^+$.

Synthesis of Compound 1-a 1-b (600 mg, 2.36 mmol) was dissolved in dichloromethane (10 mL) and trifluoroacetic acid (10 mL), and the mixture was stirred at room temperature overnight. After the reaction was completed, the organic solvent was concentrated under reduced pressure, to which saturated aqueous sodium bicarbonate solution (10 mL) and DCM (10 mL) were added, then the liquid was separated. The aqueous layer was extracted with dichloromethane, and the organic layers were combined, dried over anhydrous sodium sulfate, filtered, and concentrated to obtain 1-a (300 mg, 81%) as a brown solid. LC-MS (ESI): m/z=159.2 [M+H]$^+$.

Synthesis of Compound 1

Compound 1-a (40 mg, 0.25 mmol), 1-c (56 mg, 0.25 mmol), copper ferrite (6 mg, 0.025 mmol), potassium tert-butoxide (57 mg, 0.51 mmol) and anhydrous DMF (10 mL) were added to a reaction flask. The reaction solution was replaced with N2 and stirred at 150° C. overnight. After the reaction was completed, the reaction solution was diluted with ethyl acetate, washed successively with water and saturated brine, then dried over anhydrous sodium sulfate, then filtered and the filtrate was dried by rotary evaporation. The crude product was purified by prep-HPLC to obtain compound 1 (30 mg, 40%) as a white solid. LC-MS (ESI): m/z=318.1 [M+H]$^+$; $^1$H NMR (500 MHz, MeOD): δ 9.55 (d, J=2.0 Hz, 1H), 8.34 (s, 1H), 7.64 (d, J=10.0 Hz, 1H), 7.60 (t, J=8.0 Hz, 1H), 7.36 (dd, J=9.5, 2.0 Hz, 1H), 7.28 (d, J=7.5 Hz, 1H), 7.14 (dd, J=2.0, 1.0 Hz, 1H), 7.01 (d, J=8 Hz, 1H), 6.78 (dd, J=3.5, 1.5 Hz, 1H), 6.43 (dd, J=4, 3 Hz, 1H), 2.21 (s, 3H).

Synthetic Route of Compound 2

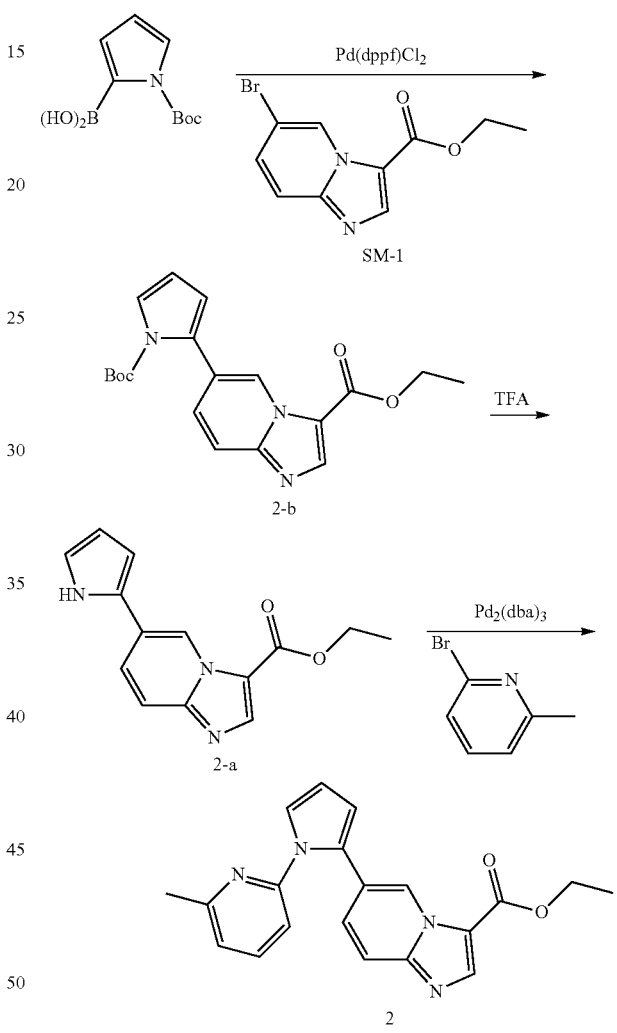

Synthesis of Compound 2-b

1-Boc-2-pyrrole-boronic acid (329 mg, 1.56 mmol), SM-1 (350 mg, 1.3 mmol), Pd(dppf)Cl$_2$ (106 mg, 0.13 mmol), sodium carbonate (345 mg, 3.25 mmol)), 1,4-dioxane (10 mL) and water (2 mL) were added to a reaction flask. The reaction solution was replaced with N$_2$ and reacted at 85° C. overnight. After the reaction was completed, the reaction solution was diluted with ethyl acetate, washed successively with water and saturated brine, then dried over anhydrous sodium sulfate, filtered and the filtrate was dried by rotary evaporation. The crude product was separated by silica gel column chromatography (PE:EA=5:1) to obtain product 2-b (450 mg, 95%) as a white solid. LC-MS (ESI): m/z=356.0 [M+H]$^+$.

Synthesis of Compound 2-a 2-b (450 mg, 1.27 mmol) was dissolved in dichloromethane (10 mL) and trifluoroacetic acid (10 mL), and the mixture was stirred at room temperature overnight. After the reaction was completed, the organic solvent was concentrated under reduced pressure, to which saturated aqueous sodium bicarbonate solution (10 mL) and DCM (10 mL) were added, and the liquid was separated. The aqueous layer was extracted with dichloromethane, and the organic layers were combined and dried over anhydrous sodium sulfate, filtered, and concentrated to give 2-a (300 mg, 92%) as a brown solid. LC-MS (ESI): m/z=256.1 [M+H]$^+$.

Synthesis of Compound 2

Compound 2-a (100 mg, 0.39 mmol), 6-bromo-2-methylpyridine (67 mg, 0.39 mmol), tris(dibenzylideneacetone)dipalladium (36 mg, 0.039 mmol), 1,1'-binaphthalene-2,2'-bisdiphenylphosphine (49 mg, 0.078 mmol), sodium tert-butoxide (75 mg, 0.78 mmol) and toluene (10 mL) were added to a reaction flask. The reaction solution was replaced with N2 and stirred at 120° C. overnight. The reaction solution was diluted with ethyl acetate, washed successively with water and saturated brine, then dried over anhydrous sodium sulfate, filtered and the filtrate was dried by rotary evaporation. The crude product was separated by silica gel column chromatography (PE:EA=1:1) to obtain product 2 (20 mg, 15%) as a brown oil. LC-MS (ESI): m/z=347.0 [M+H]$^+$.

Synthetic Route of Compound 3

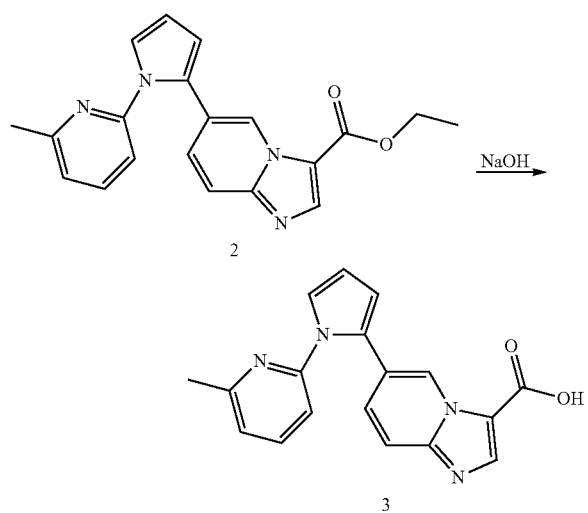

Synthesis of Compound 3

2 (20 mg, 0.057 mmol) was dissolved in methanol (2 mL) and THF (2 mL), aqueous sodium hydroxide solution (2M, 2 mL) was then added, and the mixture was stirred at room temperature overnight. After the reaction was completed, the organic solvent was concentrated under reduced pressure, water (10 mL) and DCM (10 mL) were added, and the liquid was separated, then the organic layer was discarded. The aqueous layer was cooled to 0° C. and neutralized with 2 M hydrochloric acid to a pH of 5-6. Then the aqueous layer was extracted with dichloromethane, and the organic layer was washed successively with water and saturated brine, dried over anhydrous sodium sulfate, then filtered and the filtrate was dried by rotary evaporation to obtain 3 (15 mg, 82%). LC-MS (ESI): m/z=319.0 [M+H]$^+$.

Synthetic Route of Compounds 4 and 5

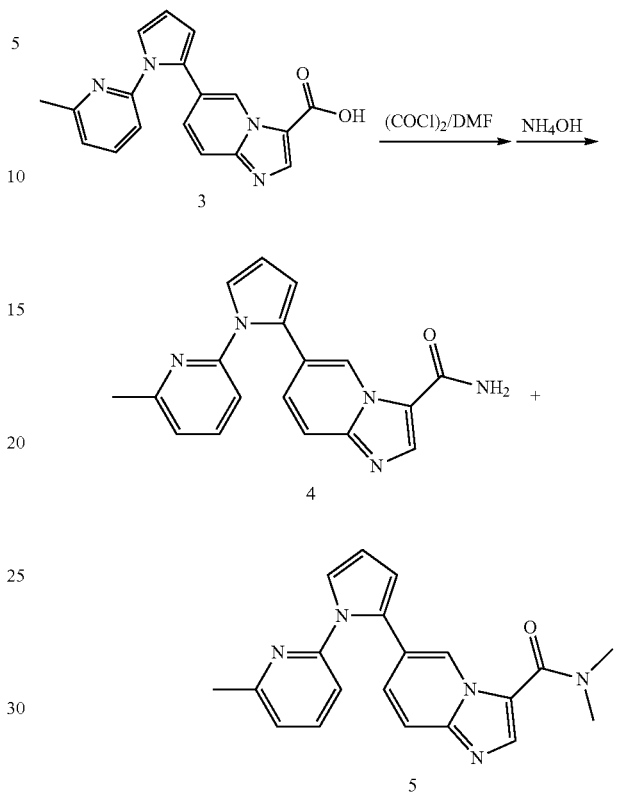

Synthesis of Compounds 4 and 5

3 (15 mg, 0.047 mmol) was dissolved in dichloromethane (10 mL). Under ice bath, oxalyl chloride (1 mL) and a drop of DMF were slowly added to the solution. The reactants were raised to room temperature and reacted for 60 minutes. The mixture was concentrated under reduced pressure and diluted with dichloromethane (5 mL). Under ice bath, the solution was slowly added dropwise to ammonia water (5 mL). The reaction mixture was reacted at 0° C. for 10 minutes, and then raised to room temperature and stirred overnight. The liquid was separated, and the aqueous layer was extracted with dichloromethane. The combined organic phases were washed successively with water and brine, dried over anhydrous sodium sulfate, and concentrated to obtain a crude product. The crude product was subjected to high performance liquid chromatography to obtain 4 as white solid (2 mg, 13%) and 5 (2 mg, 12%).

Compound 4: LC-MS (ESI): LC-MS (ESI): m/z=318.1 [M+H]$^+$; $^1$H NMR (500 MHz, MeOD): δ 9.53 (s, 1H), 8.40 (s, 1H), 7.72 (t, J=7.5 Hz, 1H), 7.63 (s, 1H), 7.39 (s, 1H), 7.34 (dd, J=3, 1.5 Hz, 1H), 7.23 (d, J=7.5 Hz, 1H), 7.03 (d, J=7.5 Hz, 1H), 6.61 (dd, J=3.5, 1.5 Hz, 1H), 6.44 (t, J=3 Hz, 1H), 2.45 (s, 3H).

Compound 5: LC-MS (ESI): m/z=346.0 [M+H]$^+$; $^1$H NMR (500 MHz, MeOD): δ 8.98 (s, 1H), 8.06 (s, 1H), 7.69 (t, J=7.5 Hz, 1H), 7.50 (d, J=9.5 Hz, 1H), 7.33 (dd, J=2.5, 1.5 Hz, 1H), 7.22 (d, J=7.5 Hz, 1H), 7.14 (dd, J=9.0, 1.5 Hz, 1H), 6.99 (d, J=8.0 Hz, 1H), 6.56 (dd, J=3.5, 2 Hz, 1H), 6.41 (t, J=3.5 Hz, 1H), 3.27 (s, 6H), 2.47 (s, 3H).

Synthetic Route of Compound 6

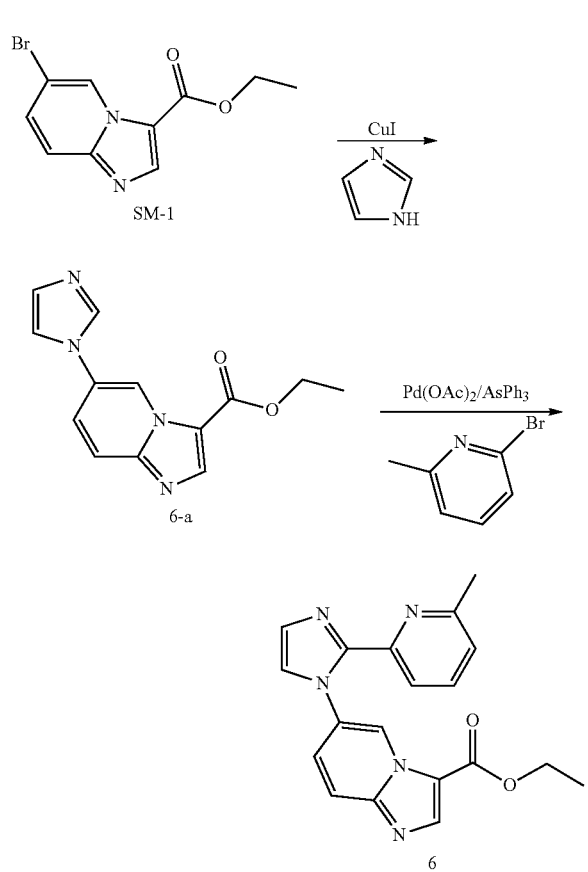

Synthesis of Compound 6-a

Compound imidazole (531 mg, 7.8 mmol), SM-1 (2 g, 7.43 mmol), cuprous iodide (141 mg, 0.74 mmol), potassium carbonate (2 g, 14.86 mmol), L-proline (171.1 mg, 1.48 mmol) and anhydrous dimethyl sulfoxide (10 mL) were added to a reaction flask. The reaction solution was replaced with N2 and stirred at 120° C. overnight. The reaction solution was diluted with ethyl acetate, washed successively with water and saturated brine, dried over anhydrous sodium sulfate, then filtered and the filtrate was dried by rotary evaporation. The crude product was separated by silica gel column chromatography (PE:EA=1:1) to obtain the product 6-a (0.5 g, 26%) as a brown solid. LC-MS (ESI): m/z=257.2 [M+H]$^+$.

Synthesis of Compound 6

Compound 6-a (400 mg, 1.56 mmol), 2-bromo-6-methylpyridine (537 mg, 3.12 mmol), cesium fluoride (474 mg, 3.12 mmol), palladium acetate (35 mg, 0.156 mmol), triphenylarsenic (96 mg, 0.312 mmol) and DMF (10 mL) were added to a reaction flask. The reaction solution was replaced with N$_2$ and stirred at 140° C. overnight. After the reaction was completed, the reaction solution was diluted with ethyl acetate, washed successively with water and saturated brine, dried over anhydrous sodium sulfate, then filtered and the filtrate was dried by rotary evaporation to obtain a crude product. The crude product was subjected to high performance liquid chromatography to obtain compound 6 (30 mg, 5.5%) as a white solid. LC-MS (ESI): m/z=348.1 [M+H]$^+$.

Synthetic Route of Compound 7

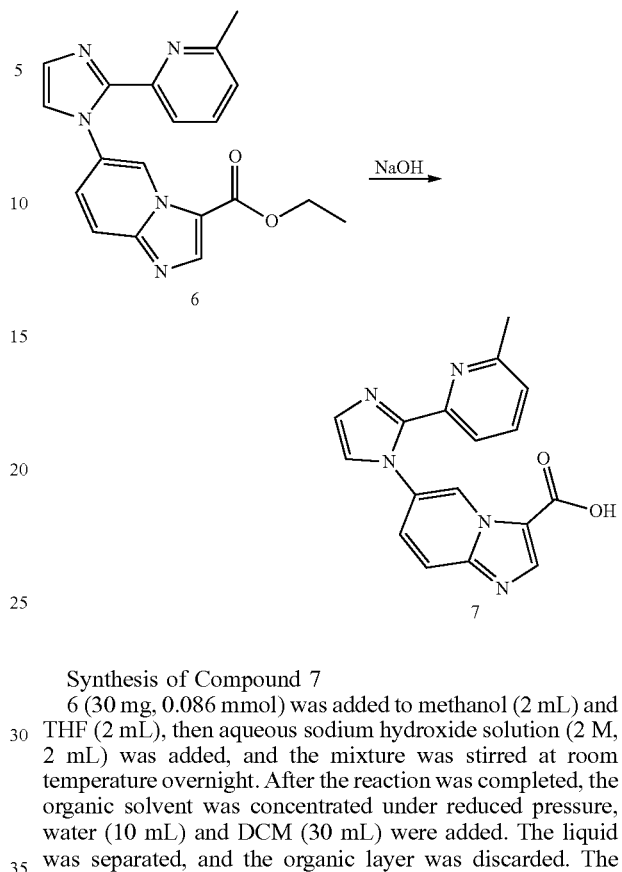

Synthesis of Compound 7

6 (30 mg, 0.086 mmol) was added to methanol (2 mL) and THF (2 mL), then aqueous sodium hydroxide solution (2 M, 2 mL) was added, and the mixture was stirred at room temperature overnight. After the reaction was completed, the organic solvent was concentrated under reduced pressure, water (10 mL) and DCM (30 mL) were added. The liquid was separated, and the organic layer was discarded. The aqueous layer was cooled to 0° C. and neutralized with 2 M hydrochloric acid to a pH of 6-7. The yellowish precipitate was filtered off and dried to obtain compound 7 (20 mg, 72%). LC-MS (ESI): m/z=320.0 [M+H]$^+$.

Synthetic Route of Compound 8

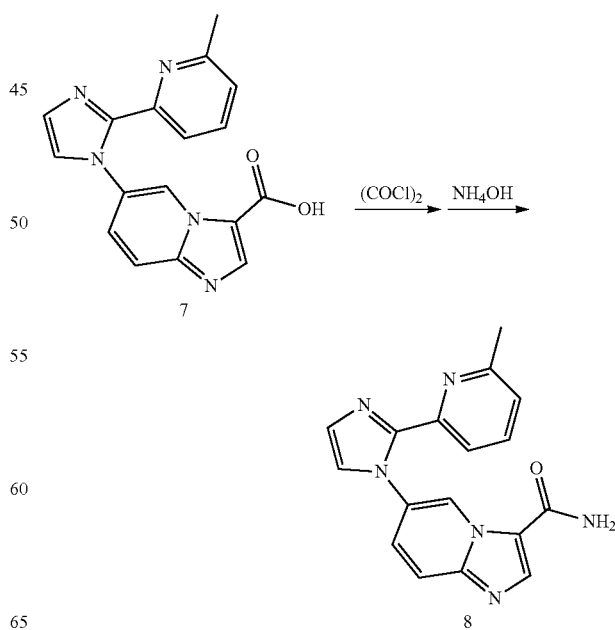

Synthesis of Compound 8

7 (20 mg, 0.063 mmol) was dissolved in dichloromethane (10 mL). Under ice bath, oxalyl chloride (1 mL) and a drop of DMF were slowly added to the solution. The reactants were raised to room temperature and reacted for 60 minutes. The mixture was concentrated under reduced pressure and diluted with dichloromethane (5 mL). Under ice bath, the solution was slowly added dropwise to ammonia water (5 mL), and the reaction mixture reacted at 0° C. for 10 minutes, and then raised to room temperature and stirred overnight. The liquid were separated, and the aqueous layer was extracted with dichloromethane. The combined organic phases were washed successively with water and brine, dried over anhydrous sodium sulfate, and concentrated to obtain a crude product. The crude product was subjected to high performance liquid chromatography to obtain compound 8 (5 mg, 25%) as a white solid. LC-MS (ESI): m/z=319.1 [M+H]$^+$; $^1$H NMR (500 MHz, MeOD): δ 9.65 (s, 1H), 8.38 (s, 1H), 7.72-7.81 (m, 3H), 7.55 (s, 1H), 7.52 (d, J=9.5 Hz, 1H), 7.32 (s, 1H), 7.17 (d, J=7.5 Hz, 1H), 2.12 (s, 3H).

Synthetic Route of Compound 9

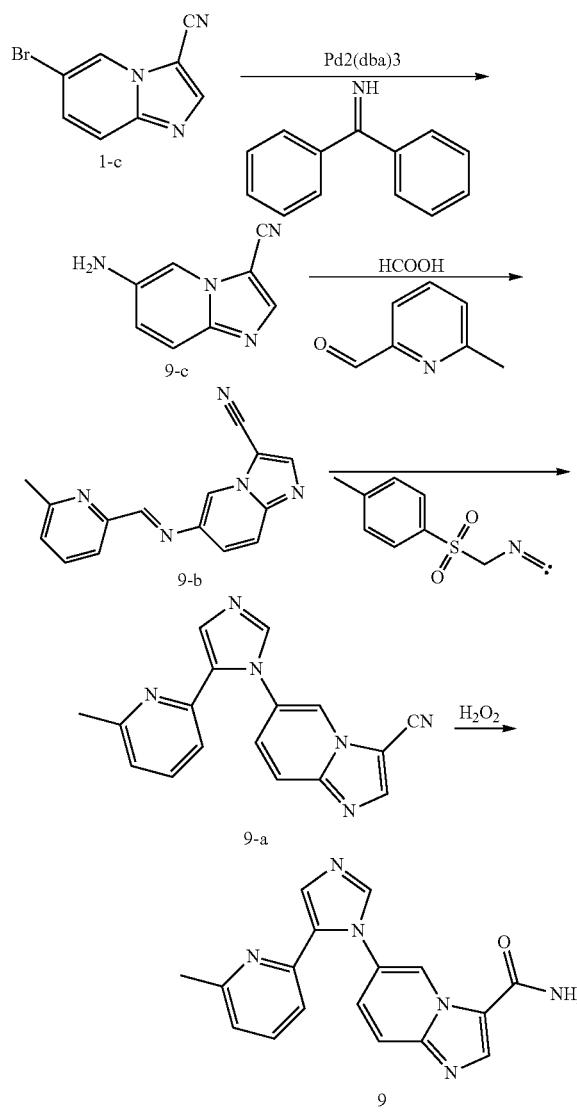

Synthesis of Compound 9-c

Compound 1-c (1.2 g, 5.4 mmol), benzophenone imine (1.47 g, 8.1 mmol), sodium tert-butoxide (1.04 g, 10.81 mmol), Pd$_2$(dba)$_3$ (247.4 mg, 0.27 mmol), 1,1'-binaphthalene-2,2'-bisdiphenylphosphine (336 mg, 0.54 mmol) and toluene (40 mL) were added to a reaction flask. The reaction solution was replaced with N$_2$ and stirred at 100° C. for one hour. After the reaction was completed, it was diluted with ethyl acetate, washed successively with water and saturated brine, dried over anhydrous sodium sulfate, then filtered and the filtrate was dried by rotary evaporation to obtain a black oil. Dilute hydrochloric acid (2M, 10 mL) was added, the reaction solution was stirred for half an hour, neutralized with solid sodium bicarbonate to pH>7, and extracted with dichloromethane. The organic phase was dried, concentrated, and the resulting crude product was subjected to silica gel column chromatography to obtain solid 9-c (0.5 g, 59%). LC-MS (ESI): m/z=159.1 [M+H]$^+$.

Synthesis of Compound 9-b

Compound 6-methyl-2-pyridinecarbaldehyde (200 mg, 1.26 mmol), 9-c (200 mg, 1.26 mmol), methanol (10 mL) and a few drops of formic acid were added to a reaction flask. The reaction solution was stirred at room temperature overnight. After the reaction was completed, it was concentrated, and the resulting solid was washed with ethyl acetate and dried to obtain product 9-b (0.2 g, 61%) which was solid. LC-MS (ESI): m/z=262.1 [M+H]$^+$.

Synthesis of Compound 9

Compound 9-b (50 mg, 0.19 mmol), p-toluenesulfonyl-methylisonitrile (56 mg, 0.287 mmol), potassium carbonate (56 mg, 0.4 mmol), DMF (4.6 mL) and ethylene glycol dimethyl ether (3.75 mL) were added to a reaction flask. The reaction solution was replaced with N2 and stirred at 100° C. for 2 hours. After the reaction was completed, it was concentrated and the resulting oil was re-dissolved in dimethyl sulfoxide (2 mL). Under ice bath, 30% hydrogen peroxide (24.9 mg, 0.73 mmol) was added dropwise to the solution. The mixture was heated to room temperature and stirred overnight. After the reaction was completed, it was filtered, and the filtrate was subjected to high performance liquid chromatography to obtain 9 (15 mg, 26%) as a white solid. LC-MS (ESI): m/z=319.0 [M+H]$^+$; $^1$H NMR (400 MHz, MeOD): δ 9.70 (s, 1H), 8.38 (s, 1H), 8.09 (s, 1H), 7.73 (d, J=9.2, 1H), 7.70 (t, J=8.0 Hz, 1H), 7.62 (s, 1H), 7.46 (dd, J=9.6, 2.0 Hz, 1H), 7.43 (d, J=7.6 Hz, 1H), 7.11 (t, J=8.0 Hz, 1H), 2.21 (s, 3H).

Synthetic Route of Compound 10

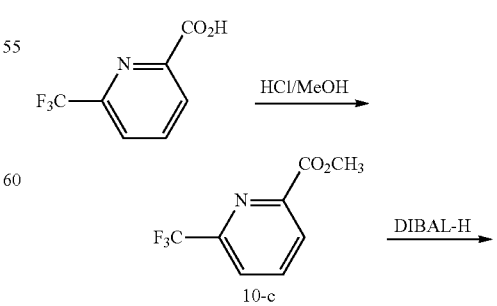

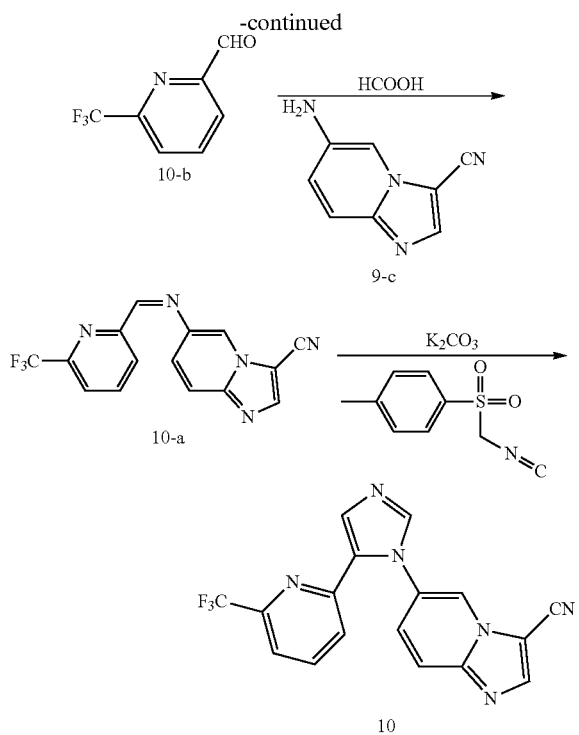

Synthesis of Compound 10-c

At room temperature, concentrated hydrochloric acid (2.0 mL) was added to a solution of 6-trifluoromethylpyridine-2-carboxylic acid (1.91 g, 10.0 mmol) in methanol (20 mL), and the mixture was stirred at 80° C. overnight. After the reaction was completed, the solvent was removed by rotary evaporation, and the residue was dissolved in ethyl acetate (100 mL) solution. The solution was washed with saturated sodium bicarbonate solution (50 mL), then washed with sodium chloride (50 mL), and dried over anhydrous sodium sulfate, then filtered and concentrated to obtain 10-c (1.89 g, 92%) as a white solid. LC-MS (ESI): m/z=206.1 [M+H]$^+$.

Synthesis of Compound 10-b

A solution of 10-c (800 mg, 3.9 mmol) in tetrahydrofuran (10 mL) was cooled to −78° C., and after stirring for 10 minutes, DIBAL-H (5.8 mL, 5.8 mmol, 1.0 M in toluene) was added dropwise. After stirring the solution at −78° C. for 1 hour, the reaction was quenched by addition of methanol (2.0 mL). The reaction solution was diluted with sodium bicarbonate solution (30 mL), extracted with ethyl acetate (30 mL*3) and washed with saline (50 mL), and then dried over anhydrous sodium sulfate, filtered, and concentrated. The crude product was purified by column chromatography (petroleum ether/ethyl acetate=10/1) to obtain 10-b (142 mg, 21%) as a pale yellow solid. LC-MS (ESI): m/z=176.0 [M+H]$^+$.

Synthesis of Compound 10-a 10-b (142 mg, 0.81 mmol) and 9-c (128 mg, 0.81 mmol) were dissolved in methanol (8 mL), a drop of formic acid was added, and the mixture reacted for 3 hours at room temperature. After the reaction was completed, the solvent was removed by rotary evaporation, and the residue was washed with petroleum ether/ethyl acetate (1/1) to obtain 10-a (174 mg, 68%) as a brown solid. LC-MS (ESI): m/z=316.0 [M+H]$^+$.

Synthesis of Compound 10

Under nitrogen atmosphere, 10-a (174 mg, 0.55 mmol), a solution of p-toluenesulfonylmethylisonitrile (162 mg, 0.83 mmol) and potassium carbonate (160 mg, 1.16 mmol) in DMF/DME (2 mL/1.67 mL) was heated to 100° C. and stirred overnight. After the reaction was completed, one third of the reaction solution was taken for filtration, and the crude product was purified by Prep-HPLC to obtain 10 (15 mg+60 mg crude product, 38%) as a white solid. LC-MS (ESI): m/z=355.0 [M+H]$^+$; $^1$H NMR (500 MHz, MeOD): δ8.92 (t, 1H, J=1.0 Hz), 8.38 (s, 1H), 8.13 (s, 1H), 8.05-8.02 (m, 2H), 7.89 (s, 1H), 7.82 (q, 1H, J=0.5, 9.5 Hz), 7.61-7.55 (m, 2H).

Synthetic Route of Compound 11

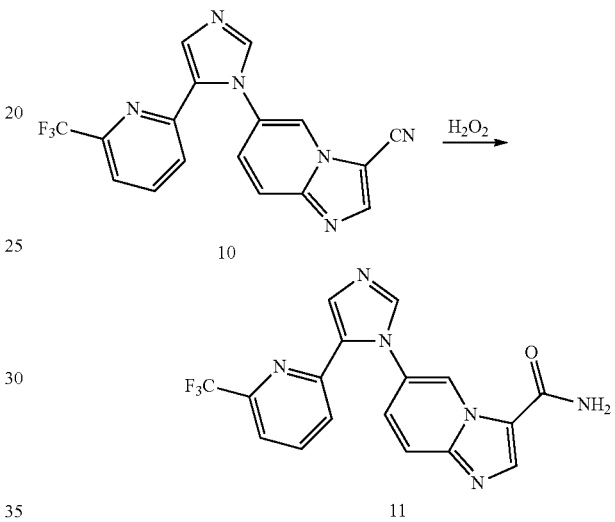

Synthesis of Compound 11

30% Hydrogen peroxide (1 mL) was added to 10 (60 mg, 0.17 mmol) the remaining two-thirds of the DMF/DME reaction solution and the mixture was stirred at room temperature for 2 hours. After the reaction was completed, the reaction solution was filtered. The crude product was purified by Prep-HPLC to obtain 11 (38 mg, 60%) as a white solid. LC-MS (ESI): m/z=373.0 [M+H]$^+$; $^1$H NMR (500 MHz, DMSO-d$_6$): δ9.55 (s, 1H), 8.42 (s, 1H), 8.17 (s, 1H), 8.06 (s, 3H), 7.92 (s, 1H), 7.74 (d, 1H, J=8.5 Hz), 7.63 (s, 1H), 7.46 (d, 2H, J=9.5 Hz).

Synthetic Route of Compound 13

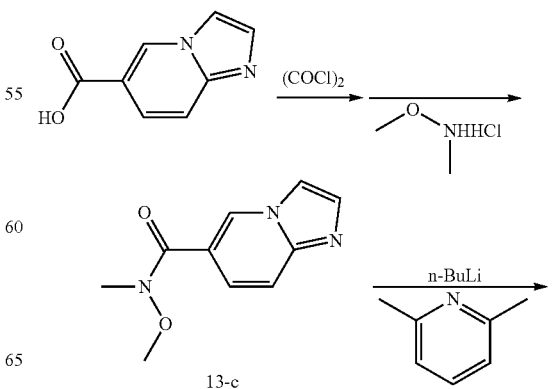

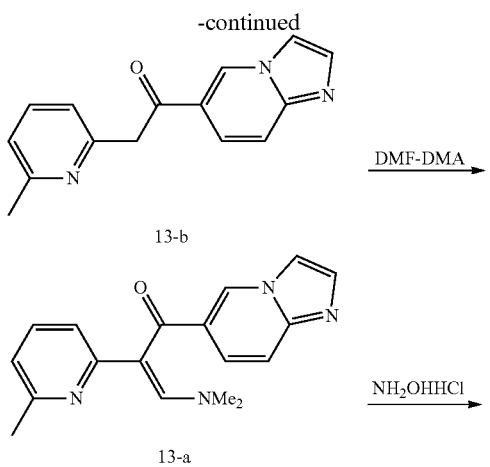

Synthesis of Compound 13-c

Mixture of imidazo[1,2-a]pyridine-6-carboxylic acid (4.86 g, 30.0 mmol) was dissolved in dichloromethane (250 mL). Under ice bath, oxalyl chloride (10 mL) was added to the solution, then DMF (0.5 mL) was slowly added to the reaction solution. The reaction mixture was raised to room temperature and was continued for 4 hours. The reaction solution was concentrated to dryness under reduced pressure, and then diluted with dichloromethane (300 mL). Under ice bath, triethylamine (50 mL) and N,O-dimethylhydroxylamine hydrochloride (6 g, 60.0 mmol) were slowly added to the reaction solution dropwise. The solution was reacted at 0° C. for 10 minutes, and then heated to room temperature and stirred for 2 hours. The dichloromethane was removed through concentration, and then water (100 mL) was added to the aqueous phase to dilute. The solution was stirred vigorously for 1 hour. Finally, the reaction solution was filtered. The filter cake was washed with water and dried to obtain 13-c (4.6 g, 75%) as a white solid. LC-MS (ESI): m/z=206.1 [M+H]+.

Synthesis of Compound 13-b

Mixture of 2,6-dimethylpyridine (8.6 g, 80.0 mmol) was dissolved in tetrahydrofuran (200 mL). Under dry ice bath at −78° C., n-butyllithium (2.5 M, 32 mL, 80.0 mmol) was slowly added dropwise to the solution. The reaction was continued for 2 hours at this temperature. 13-c (4.2 g, 20.0 mmol) was added to the reaction solution. The mixture was reacted at −78° C. for 10 minutes and then raised to room temperature and stirred for 0.5 hour. The organic phase was concentrated and subjected to column chromatography (P/E=3/1) to obtain 13-b as a yellow solid (2.8 g, 56%). LC-MS (ESI): m/z=252.1 [M+H]+.

Synthesis of Compound 13-a

A mixture of compound 13-b (0.5 g, 2.0 mmol) and DMF-DMA (1 mL) was heated to 100° C. After 3 hours of reaction, the mixture was concentrated to obtain the compound 13-a, which was directly used in the next reaction. LC-MS (ESI): m/z=307.3 [M+H]+.

Synthesis of Compound 13

A mixture of compound 13-a (0.62 g, 2.0 mmol), hydroxylamine hydrochloride (0.84 g, 12.0 mmol) and ethanol (10 mL) was heated to 100° C. for 3 hours and concentrated. Saturated sodium bicarbonate (100 mL) was added to the product to alkalize it, and the solution was stirred vigorously for 1 hour. Finally, the reaction solution was filtered. The filter cake was washed with water and dried to obtain solid 13 (0.5 g, 91%). LC-MS (ESI): m/z=277.1 [M+H]+; 1H NMR (500 MHz, MeOD): δ 9.36 (s, 1H), 8.88 (s, 1H), 7.98 (s, 1H), 7.77 (t, J=7.5 Hz, 1H), 7.64 (d, J=9.5 Hz, 1H), 7.60 (dd, J=2.0, 9.5 Hz, 2H), 7.46 (d, J=7.5 Hz, 1H), 7.30 (d, J=8.0 Hz, 1H), 2.59 (s, 3H).

Synthetic Route of Compound 14

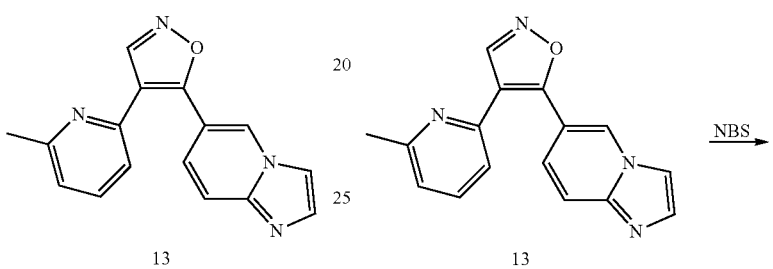

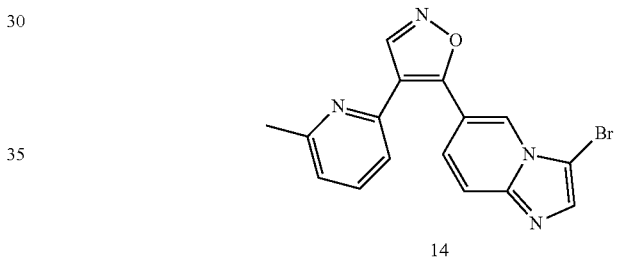

Synthesis of Compound 14

A mixture of compound 13 (0.14 g, 0.5 mmol), NBS (0.1 g, 0.56 mmol) and dichloromethane (10 mL) was reacted at room temperature for 3 hours and concentrated. Water (10 mL) was added to the product and the solution was stirred vigorously for 1 hour. The solution was filtere and the filter cake was washed with water and dried to obtain solid 14 (0.18 g, 100%). LC-MS (ESI): m/z 355 [M+H]+; 1H NMR (400 MHz, MeOD): δ 9.24 (s, 1H), 8.91 (s, 1H), 7.81 (m, 3H), 7.73 (d, J=6.4 Hz, 1H), 7.51 (d, J=6.0 Hz, 1H), 7.32 (d, J=6.0 Hz, 1H), 2.63 (s, 3H).

Synthetic Route of Compound 15

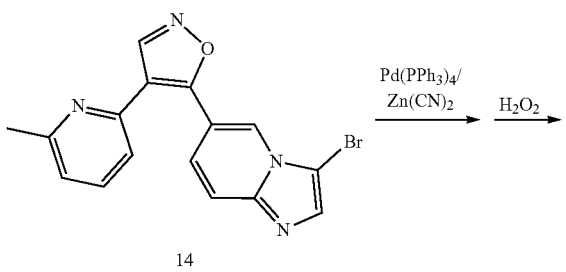

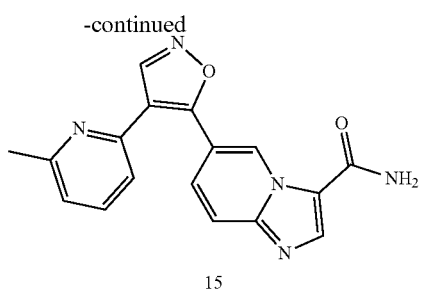

15

Synthesis of Compound 15

A mixture of the compounds zinc cyanide (0.12 g, 1.0 mmol), 14 (0.15 g, 0.42 mmol), tetratriphenylphosphine palladium (0.115 g, 0.1 mmol) and DMF (10 mL) was heated to 150° C. and reacted for 48-hours in a sealed tube under nitrogen atmosphere. The reaction mixture was cooled to room temperature and concentrated, and dilute hydrochloric acid (10 mL, 30 mmol) and ethyl acetate (300 mL*3) were added for extraction. The solution was basified to pH to 8 with aqueous solution of sodium bicarbonate and filtered. The filter cake was dried and purified by preparative high-performance liquid chromatography to obtain compound 15 (0.006 g, 3.7%) as a pale yellow solid. LC-MS (ESI): m/z=320.0 [M+H]$^+$; $^1$H NMR (500 MHz, MeOD): δ 10.03 (s, 1H), 8.25 (s, 1H), 7.93 (t, J=8.0 Hz, 1H), 7.83 (dd, J=9.0, 1.5 Hz, 1H), 7.64 (d, J=9.5 Hz, 1H), 7.54 (d, J=9.5 Hz, 1H), 7.31 (d, J=8.5 Hz, 1H), 7.05 (d, J=7.5 Hz, 1H), 2.57 (s, 3H).

Synthetic Route of Compound 16

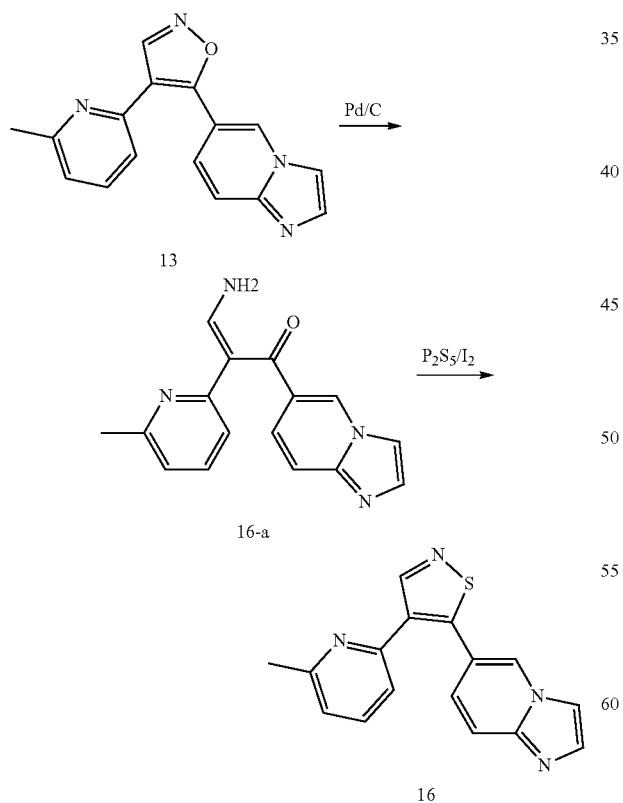

Compound 13 (0.276 g, 1.0 mmol), Pd/C (0.1 g) and ethanol (10 mL) were mixed at room temperature. After being replaced with hydrogen, the mixture was stirred and reacted at room temperature for 3 hours, then filtered and concentrated to obtain solid 16-a (0.26 g, 94%). LC-MS (ESI): m/z=279.1 [M+H]$^+$.

Compound 16-a (0.26 g, 0.93 mmol), iodine (0.5 g, 2.0 mmol), P$_2$S$_5$ (0.44 g, 2.0 mmol) and dichloromethane (60 mL) were mixed at room temperature, and the reaction was stirred at room temperature for 24 hours. The reaction was quenched with saturated sodium bisulfite (60 mL), extracted with dichloromethane (100*3 mL), and the organic phase was concentrated and subjected to column chromatography (P/E=1/3) to obtain solid 16 (0.05 g, 18%). LC-MS (ESI): m/z=293.0 [M+H]$^+$; $^1$H NMR (500 MHz, MeOD): δ 8.84 (s, 1H), 8.76 (s, 1H), 7.93 (s, 1H), 7.70 (t, J=6.0 Hz, 1H), 7.65 (d, J=1.5H, 1H), 7.56 (d, J=9.5 Hz, 1H), 7.27 (s, 1H), 7.26 (s, 1H), 7.15 (d, J=9.5, 1.5 Hz, 1H), 2.53 (s, 3H).

Synthetic Route of Compound 17

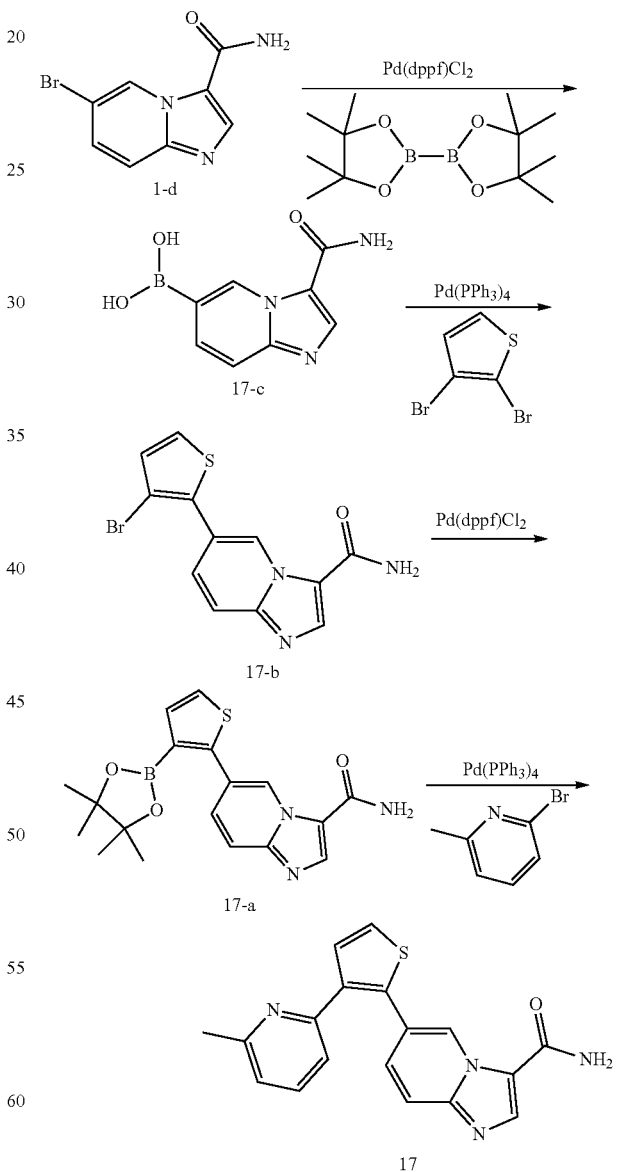

Synthesis of Compound 17-c

A mixture of compound 1-d (7.2 g, 30.1 mmol), diborate (22.86 g, 90 mmol), potassium acetate (8.82 g, 90 mmol), Pd(dppf)Cl$_2$ (0.43 g, 0.53 mmol) and dry dioxane (80 mL) was heated to 100° C. and reacted for 3 hours under nitrogen atmosphere. The reaction was cooled to room temperature and concentrated. Water (200 mL) was added and stirred, then filtered and the filter cake was dried. The obtained solid was dissolved in ethyl acetate (200 mL), and a saturated ethyl acetate hydrochloric acid solution (20 mL) was added under stirring, then filtered and the filter cake was dried to obtain compound 17-c (5.96 g, 97%). LC-MS (ESI): m/z=206 [M+H]$^+$. $^1$H NMR (400 MHz, CD$_3$OD): δ 9.96 (s, 1H), 8.54 (s, 1H), 8.13 (d, J=8.0 Hz, 1H), 7.89 (d, J=8.0 Hz, 1H).

Synthesis of Compound 17-b 2,3-Dibromothiophene (500 mg, 2.07 mmol), 17-c (424 mg, 2.07 mmol), tetrakis(triphenylphosphine) palladium (120 mg, 0.1 mmol), sodium carbonate (878 mg, 8.28 mmol), 1,4-dioxane (20 mL) and water (5 mL) were added to a reaction flask. The reaction mixture was replaced with N$_2$ and reacted at 100° C. overnight. After the reaction was completed, the organic solvent was removed through concentration, and the crude product was purified by column chromatography (DCM:MeOH=30:1) to obtain compound 17-b (0.27 g, 41%) as a white solid. LC-MS (ESI): m/z=321.8 [M+H]$^+$.

Synthesis of Compound 17-a 17-b (0.27 g, 0.84 mmol), bis(pinacolato)diboron (255 mg, 1 mmol), Pd(dppf)Cl$_2$ (31 mg, 0.042 mmol), potassium acetate (165 mg), 1.68 mmol), 1,4-dioxane (10 mL) and toluene (10 mL) were added to a reaction flask. The reaction mixture was replaced with N$_2$ and reacted at 90° C. overnight. After the reaction was completed, the organic solvent was removed through concentration, and the crude product was purified by column chromatography (DCM:MeOH=20:1) to obtain compound 17-a (0.22 g, 71%) as a yellow solid. LC-MS (ESI): m/z=370.0 [M+H]$^+$.

Synthesis of Compound 17

17-a (0.22 g, 0.59 mmol), 2-bromo-6-methylpyridine (123 mg, 0.72 mmol), tetrakis(triphenylphosphine)palladium (69 mg, 0.06 mmol), sodium carbonate (126 mg, 1.19 mmol), 1,4-dioxane (15 mL) and water (3 mL) were added to a reaction flask. The reaction mixture was replaced with N$_2$ and reacted at 90° C. overnight. After the reaction was completed, the organic solvent was removed through concentration, and the crude product was purified by Prep-HPLC to obtain compound 17 (45 mg, 23%) as a white solid. LC-MS (ESI): m/z=335.0 [M+H]$^+$; $^1$H NMR (500 MHz, DMSO): δ 9.61 (s, 1H), 8.35 (s, 1H), 7.99 (brs, 1H), 7.71 (d, J=5.0 Hz, 1H), 7.65 (d, J=9.5 Hz, 1H), 7.58 (t, J=7.5 Hz, 1H), 7.52 (d, J=5.0 Hz, 1H), 7.41 (brs, 1H), 7.25 (dd, J=9.5, 1.5 Hz, 1H), 7.15 (d, J=8.0 Hz, 1H), 7.15 (d, J=8.0 Hz, 1H), 2.38 (s, 3H).

Synthetic Route of Compound 18

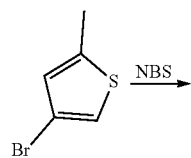

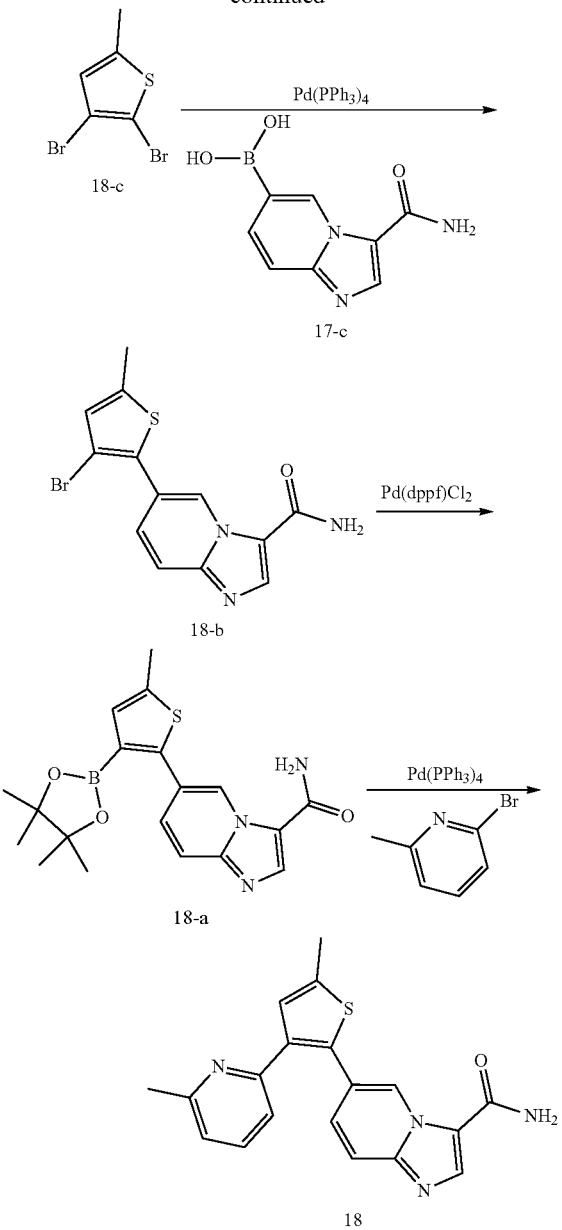

Synthesis of Compound 18-c

4-Bromo-2-methylthiophene (1 g, 5.65 mmol), DMF (5 mL) and NBS (1.1 g, 6.18 mmol) were added to a reaction flask, and the mixture reacted at room temperature overnight. Water (30 mL) was added to the mixture, and then the mixture was extracted with petroleum ether (30 mL). The organic phase was washed successively with water and saturated aqueous sodium chloride solution and dried over anhydrous sodium sulfate. After filtration, the solution was removed by rotary evaporation, the crude product was purified by column chromatography (using pure petroleum ether as mobile phase) to obtain compound 18-c (1.25 g, 86%) as a yellow liquid. $^1$H NMR (500 MHz, CDCl$_3$): δ 6.59 (d, J=1.1 Hz, 1H), 2.41 (d, J=1.0 Hz, 3H).

Synthesis of Compound 18-b 18-c (1 g, 3.9 mmol), 17-c (801 mg, 3.9 mmol), tetrakis (triphenylphosphine) palladium (225 mg, 0.20 mmol), sodium carbonate (1.65 g, 15.6) mmol), 1,4-dioxane (30 mL) and water (5 mL) were added to a reaction flask. The reaction mixture was replaced with N₂ and reacted at 100° C. overnight. After the reaction was completed, the organic solvent was removed through concentration and the crude product was purified by column chromatography (DCM: MeOH=20:1) to obtain compound 18-b (0.51 g, 39%) as a yellow solid. LC-MS (ESI): m/z=335.9 [M+H]⁺.

Synthesis of Compound 18-a 18-b (0.51 g, 1.52 mmol), bis(pinacolato)diboron (0.46 g, 1.82 mmol), Pd(dppf)Cl₂ (56 mg, 0.076 mmol), potassium acetate (298 mg, 3.04 mmol), 1,4-dioxane (30 mL) and toluene (20 mL) were added to a reaction flask. The reaction mixture was replaced with N₂ and reacted at 90° C. overnight. After the reaction was completed, the organic solvent was removed through concentration and the crude product was purified by column chromatography (DCM:MeOH=20:1) to obtain compound 18-a (0.46 g, 79%) as a black solid. LC-MS (ESI): m/z=384.1 [M+H]

Synthesis of Compound 18

18-a (0.46 g, 1.2 mmol), 2-bromo-6-methylpyridine (0.25 g, 1.44 mmol), tetrakis(triphenylphosphine)palladium (69 mg, 0.06 mmol), sodium carbonate (254 mg, 2.4 mmol), 1,4-dioxane (15 mL) and water (3 mL) were added to a reaction flask. The reaction mixture was replaced with N₂ and reacted at 90° C. overnight. After the reaction was completed, the organic solvent was removed through concentration and the crude product was purified by Prep-HPLC to obtain compound 18 (70 mg, 17%) as a yellow solid. LC-MS (ESI): m/z=349.0 [M+H]⁺; ¹H NMR (500 MHz, DMSO-d₆): δ 9.56 (s, 1H), 8.34 (s, 1H), 7.96 (brs, 1H), 7.63 (d, J=9.5 Hz, 1H), 7.56 (t, J=8.0 Hz, 1H), 7.37 (brs, 1H), 7.23 (d, J=1.0 Hz, 1H), 7.21 (dd, J=9.5, 2.0 Hz, 1H), 7.10 (t, J=7.0 Hz, 2H), 2.52 (s, 3H), 2.37 (s, 3H).

Synthetic Route of Compound 19

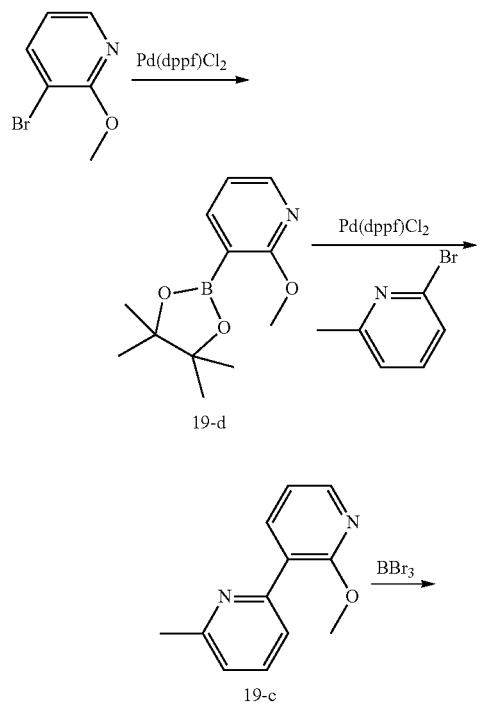

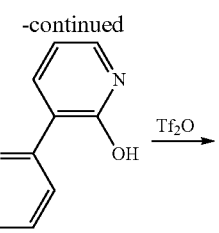

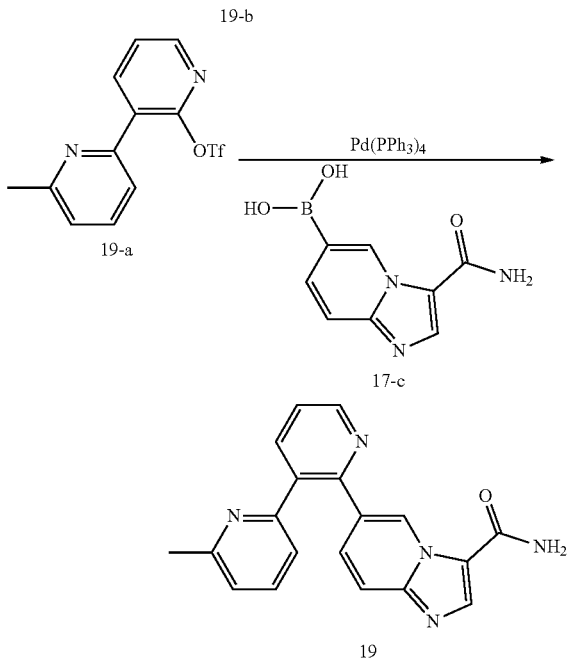

Synthesis of Compound 19-d

3-Bromo-2-methoxypyridine (2 g, 10.6 mmol), bis(pinacolato)diboron (2.74 g, 12.8 mmol), Pd(dppf)Cl₂ (388 mg, 0.53 mmol), potassium acetate (2.08 g, 21.2 mmol) and toluene (20 mL) were added to a reaction flask. The reaction mixture was replaced with N₂ and reacted at 90° C. overnight. After the reaction was completed, the mixture was concentrated, and water (20 mL) was added. The solution was extracted with ethyl acetate (30 mL*2), and the organic phase was dried over anhydrous sodium sulfate. After the organic phase was filtered and concentrated, the crude product was purified by column chromatography (PE:EA=4:1) to obtain crude compound 19-d (2.2 g, 88%) as a yellow oil. LC-MS (ESI): m/z=236.1[M+H]

Synthesis of Compound 19-c 2-bromo-6-methylpyridine (0.9 g, 5.23 mmol), 19-d (1.6 g, 6.8 mmol), Pd(dppf)Cl₂ (191 mg, 0.26 mmol), sodium carbonate (1.11 g, 10.46 mmol), 1,4-dioxane (20 mL) and water (4 mL) were added to a reaction flask. The reaction mixture was replaced with N₂ and reacted at 80° C. overnight. After the reaction was completed, the mixture was concentrated, and water (20 mL) was added. The solution was extracted with ethyl acetate (30 mL*2), and the organic phase was dried over anhydrous sodium sulfate, then filtered and concentrated, the crude product was purified by column chromatography (PE:EA=30:1) to obtain compound 19-c (0.97 g, 92%) as a yellow solid, LC-MS (ESI): m/z=201.1 [M+H]⁺.

Synthesis of Compound 19-b 19-c (0.97 g, 4.84 mmol) was dissolved in dichloromethane (15 mL), cooled in dry ice acetone bath, and a solution of boron tribromide in dichloromethane (1.0 M, 14.5 mL, 14.5 mmol) was slowly added. The temperature was slowly raised to room temperature. After reacting overnight, the reaction was quenched by adding saturated sodium bicarbonate aqueous solution. The solution was extracted with dichloromethane (30 mL*2), and the organic phase was dried over anhydrous sodium sulfate. After the organic phase was filtered and concentrated, the crude product was purified by column chromatography (PE:EA=5:1 to DCM:MeOH=30:1) to obtain compound 19-b (0.33 g, 37%) as a yellow solid. LC-MS (ESI): m/z=187.3 [M+H]$^+$.

Synthesis of Compound 19-a 19-b (0.33 g, 1.77 mmol) and pyridine (0.7 g, 8.85 mmol) were dissolved in dichloromethane (10 mL), cooled in ice water bath, and trifluoromethanesulfonic anhydride (1 g, 3.54 mmol) was slowly added. The mixture was stirred at room temperature overnight. After concentration, the crude product was purified by column chromatography (PE:EA=5:1) to obtain compound 19-a (415 mg, 74%) as a yellow oil. LC-MS (ESI): m/z=319.1[M+H]$^+$.

Synthesis of Compound 19

19-a (215 mg, 0.68 mmol), 17-c (166 mg, 0.81 mmol), tetrakis(triphenylphosphine) palladium (39 mg, 0.034 mmol), sodium carbonate (144 mg, 1.36 mmol), toluene (6 mL), ethanol (6 mL) and water (3 mL) were added to a reaction flask. The reaction mixture was replaced with N2 and reacted at 90° C. overnight. After the reaction was completed, the organic solvent was removed through concentration. Water (20 mL) was added, and the solution was extracted with ethyl acetate (30 mL). The organic phase was washed successively with water and saturated aqueous sodium chloride solution and dried over anhydrous sodium sulfate. After filtration, the solution was dried by rotary evaporation. The crude product was purified by Prep-HPLC to obtain compound 19 (88 mg, 40%) as a white solid. LC-MS (ESI): m/z=330.1 [M+H]$^+$; $^1$H NMR (500 MHz, DMSO-d$_6$): δ 9.63 (s, 1H), 8.77 (dd, J=4.5, 1.5 Hz, 1H), 8.33 (s, 1H), 8.04 (dd, J=7.5, 1.5 Hz, 1H), 7.93 (brs, 1H), 7.55-7.61 (m, 2H), 7.37 (brs, 1H), 7.18 (d, J=8.0 Hz, 1H), 7.13 (dd, J=9.5, 1.5 Hz, 1H), 7.08 (d, J=8.0 Hz, 1H), 2.43 (s, 3H).

Synthetic Route of Compound 20

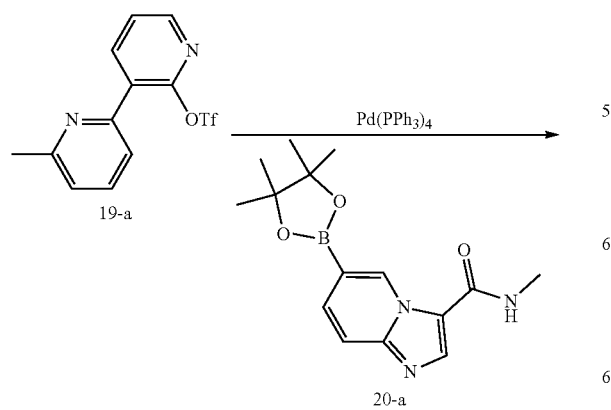

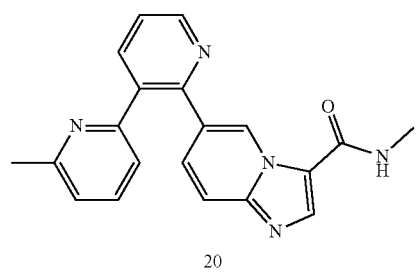

Synthesis of Compound 20-a

Compound 20-a was prepared according to the synthetic route of 17-c by using 1-e as the raw material.

Synthesis of Compound 20

19-a (200 mg, 0.63 mmol), 20-a (208 mg, 0.69 mmol), tetrakis(triphenylphosphine)palladium (36 mg, 0.032 mmol), sodium carbonate (133 mg, 1.26 mmol), toluene (6 mL), ethanol (6 mL) and water (3 mL) were added to a reaction flask. The reaction mixture was replaced with N$_2$ and reacted at 90° C. overnight. After the reaction was completed, the organic solvent was removed through concentration. Water (30 mL) was added, and the solution was extracted with ethyl acetate (30 mL). The organic phase was washed successively with water and saturated aqueous sodium chloride solution and dried over anhydrous sodium sulfate. After filtration, the solution was dried by rotary evaporation. The crude product was purified by Prep-HPLC to obtain compound 20 (52 mg, 24%) which was white solid. LC-MS (ESI): m/z=344.1 [M+H]$^+$; $^1$H NMR (500 MHz, DMSO-d$_6$): δ 9.65 (s, 1H), 8.76 (dd, J=4.5, 1.5 Hz, 1H), 8.38-8.48 (m, 1H), 8.26 (s, 1H), 8.04 (dd, J=7.5, 1.5 Hz, 1H), 7.61-7.55 (m, 2H), 7.51 (d, J=8.5 Hz, 1H), 7.19 (d, J=8.0 Hz, 1H), 7.11-7.05 (m, 2H), 2.80 (d, J=4.5 Hz, 3H), 2.43 (s, 3H).

Synthetic Route of Compound 21

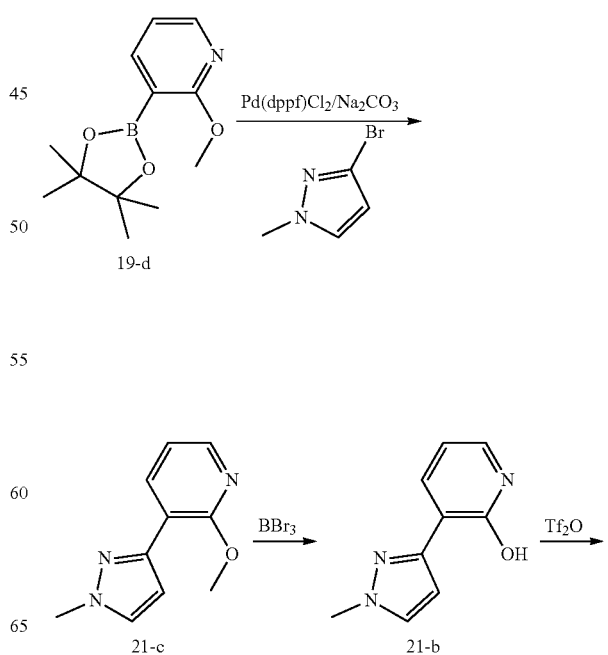

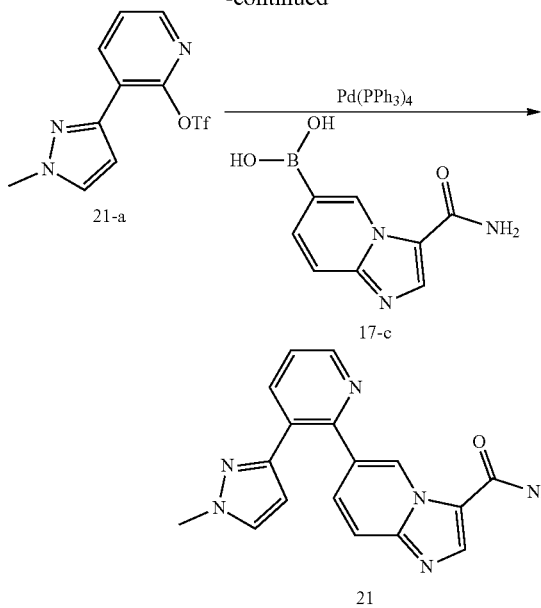

Synthesis of Compound 21

21-a (244 mg, 0.79 mmol), 17-c (195 mg, 0.95 mmol), tetrakis(triphenylphosphine) palladium (46 mg, 0.040 mmol), sodium carbonate (167 mg, 1.58 mmol), toluene (8 mL), ethanol (8 mL) and water (4 mL) were added to a reaction flask. The reaction mixture was replaced with N2 and reacted at 90° C. overnight. After the reaction was completed, the organic solvent was removed through concentration. Water (20 mL) was added, and the solution was extracted with ethyl acetate (30 mL*2). The organic phase was washed successively with water and saturated aqueous sodium chloride solution and dried over anhydrous sodium sulfate. After filtration, the solution was dried by rotary evaporation. The crude product was purified by Prep-HPLC to obtain compound 21 (90 mg, 36%) as a white solid. LC-MS (ESI): m/z=319.1 [M+H]$^+$; $^1$H NMR (500 MHz, DMSO-d$_6$): δ 9.68 (s, 1H), 8.67 (dd, J=4.5, 1.5 Hz, 1H), 8.36 (s, 1H), 8.07 (dd, J=8.0, 1.5 Hz, 1H), 7.98 (brs, 1H), 7.64-7.59 (m, 2H), 7.51 (dd, J=8.0, 4.5 Hz, 1H), 7.40 (brs, 1H), 7.28 (dd, J=9.5, 1.5 Hz, 1H), 5.91 (d, J=2.2 Hz, 1H), 3.83 (s, 3H).

Synthetic Route of Compound 22

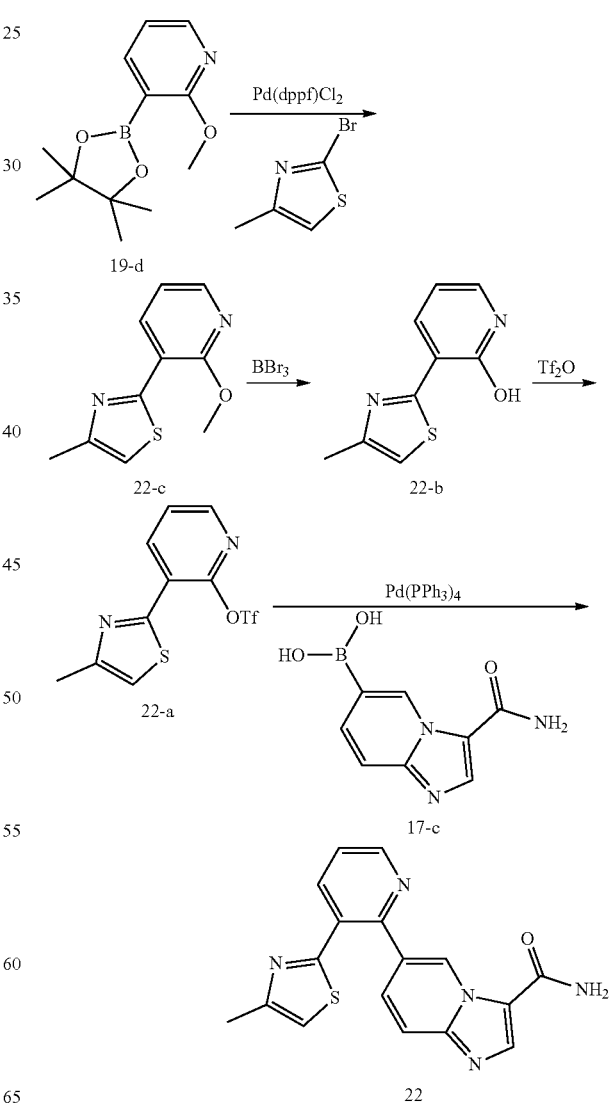

Synthesis of Compound 21-c

3-Bromo-1-methylpyrrole (310 mg, 1.93 mmol), 19-d (543 mg, 2.31 mmol), Pd(dppf)Cl$_2$ (70 mg, 0.095 mmol), sodium carbonate (403 mg, 3.8 mmol), 1,4-dioxane (20 mL) and water (4 mL) were added to a reaction flask. The reaction mixture was replaced with N$_2$ and reacted at 90° C. overnight. After the reaction was completed, the mixture was concentrated. Water (20 mL) was added, and the solution was extracted with ethyl acetate (30 mL*2). The organic phase was dried over anhydrous sodium sulfate. After filtration, the solution was concentrated. The crude product was purified by column chromatography (PE:EA=5:1) to obtain compound 21-c (200 mg, 55%) as a yellow solid. LC-MS (ESI): m/z=190.1 [M+H]$^+$.

Synthesis of Compound 21-b 21-c (200 mg, 1.06 mmol) was dissolved in dichloromethane (10 mL), cooled in dry ice acetone bath, and a solution of boron tribromide in dichloromethane (1.0 M, 2.11 mL, 2.11 mmol) was slowly added. The temperature was slowly raised to room temperature. After reacting overnight, the reaction was quenched by adding saturated sodium bicarbonate aqueous solution. The solution was extracted with dichloromethane (30 mL*2), and the aqueous phase was dried by rotary evaporation. Dichloromethane (20 mL) was added, and the solution was filtered. The combined organic phase was dried over anhydrous sodium sulfate. After filtration, the solution was concentrated. The crude product was purified by column chromatography (DCM:MeOH=20:1) to obtain compound 21-b (139 mg, 74%) as a yellow solid. LC-MS (ESI): m/z=176.1[M+H]$^+$.

Synthesis of Compound 21-a 21-b (139 mg, 0.79 mmol) and pyridine (312 mg, 3.95 mmol) was dissolved in dichloromethane (10 mL), cooled in ice water bath, and trifluoromethanesulfonic anhydride (448 mg, 0.267 mL, 1.59 mmol) was slowly added, the mixture was stirred at room temperature overnight. After concentration, the crude product was purified by column chromatography (PE:EA=1:1) to obtain compound 21-a (244 mg, 100%) as a yellow oil. LC-MS (ESI): m/z=308.0 [M+H]$^+$.

Synthesis of Compound 22-c

Compound 2-bromo-4-methylthiazole (225 mg, 1.26 mmol), 19-d (440 mg, 1.87 mmol), Pd(dppf)Cl$_2$ (92 mg, 0.12 mmol), Na$_2$CO$_3$ (265 mg, 2.5 mmol), dioxane (15 mL) and water (3 mL) were added to a reaction flask. The reaction solution was replaced with N$_2$ and stirred at 80° C. overnight. The reaction solution was concentrated, and the crude product was separated by silica gel column chromatography (PE:EA=10:1) to obtain product 22-c (225 mg, 86%) as a yellow solid. LC-MS (ESI): m/z=207.1 [M+H]$^+$.

Synthesis of Compound 22-b

Compound 22-c (225 mg, 1.1 mmol) was dissolved in dry dichloromethane (10 mL), cooled to −78° C. in dry ice/acetone bath, and dichloromethane solution of boron tribromide (1.0M, 1.2 mL, 1.2 mmol) was slowly added to a reaction bottle. After the completion of the addition, the temperature of the reaction solution was slowly raised to room temperature and the solution was stirred overnight. The reaction solution was slowly added dropwise with saturated sodium bicarbonate aqueous solution under ice bath to separate the organic phase. The aqueous layer was extracted with dichloromethane (30 mL*2), dried over anhydrous sodium sulfate, and concentrated to obtain compound 22-b as a yellow solid (100 mg, 48%). LC-MS (ESI): m/z=324.9 [M+H]$^+$.

Synthesis of Compound 22-a 22-b (100 mg, 0.52 mmol) and pyridine (123 mg, 1.56 mmol) were dissolved in dichloromethane (15 mL), cooled in ice water bath, and trifluoromethanesulfonic anhydride (220 mg, 0.78 mmol) was slowly added. After the mixture was stirred at room temperature overnight, the mixture was concentrated. Water (20 mL) was added, and the solution was extracted with dichloromethane (20 mL*2), the combined organic phase was dried over anhydrous sodium sulfate, filtered, concentrated and purified by Prep-TLC (PE:EA=10:1) to obtain compound 22-a (20 mg, 12%) as a yellow solid. LC-MS (ESI): m/z=324.9 [M+H]$^+$.

Synthesis of Compound 22

22-a (20 mg, 0.06 mmol), 17-c (13 mg, 0.06 mmol), Pd(dppf)Cl$_2$ (4 mg, 0.006 mmol), sodium carbonate (13 mg, 0.12 mmol), 1,4-dioxane (10 mL) and water (2 mL) were added to a reaction flask. The reaction mixture was replaced with N2 and reacted at 80° C. overnight. After the reaction was completed, it was concentrated, and the crude product was purified by Prep-HPLC to obtain compound 22 (4 mg, 20%) as a white solid. LC-MS (ESI): m/z=336.0 [M+H]$^+$; $^1$H NMR (400 MHz, MeOD) δ 9.72 (s, 1H), 8.79 (dd, J=4.8, 1.6 Hz, 1H), 8.38-8.27 (m, 2H), 7.73-7.60 (m, 2H), 7.49 (dd, J=9.3, 1.8 Hz, 1H), 7.21 (s, 1H), 2.41 (s, 3H).

Synthetic Route of Compound 23

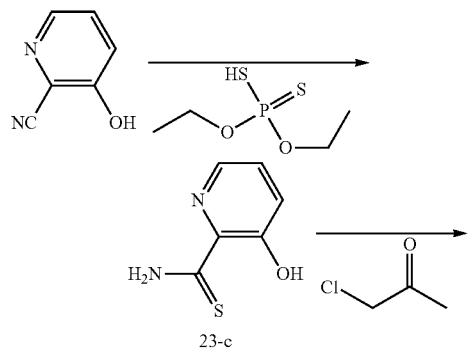

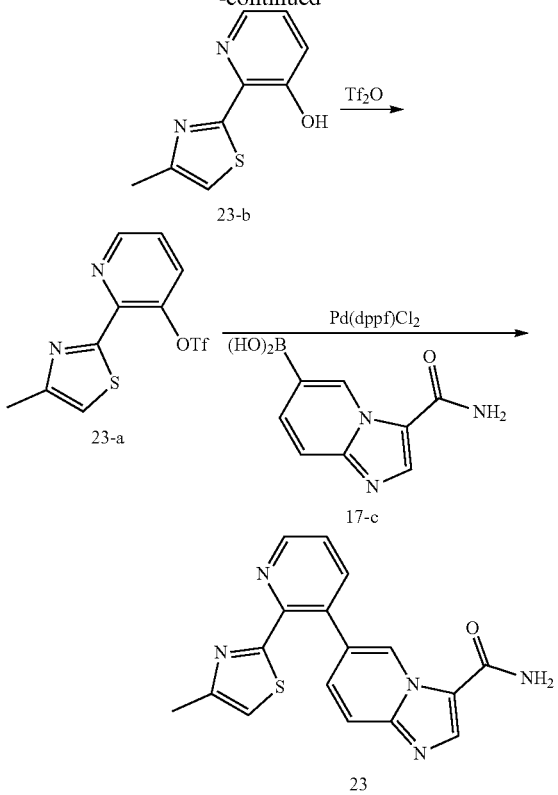

Synthesis of Compound 23-c

2-Cyano-3-hydroxypyridine (500 mg, 4.16 mmol), diethyl dithiophosphate (853 mg, 4.58 mmol) and water (6 mL) were added to a 20 mL microwave tube. The microwave tube was sealed, and the reaction solution was stirred at 90° C. overnight. After the reaction was completed, the mixture was filtered, and the filter cake was dried to obtain compound 23-c (535 mg, 83%) as a yellow solid. LC-MS (ESI): m/z=155.1 [M+H]+; $^1$H NMR (500 MHz, DMSO-d$_6$): δ 12.85 (s, 1H), 10.02-10.39 (m, 2H), 8.18 (dd, J=4.0, 1.5 Hz, 1H), 7.55 (dd, J=8.5, 4.0 Hz, 1H), 7.46 (dd, J=8.5, 1.5 Hz, 1H).

Synthesis of Compound 23-b

Compound 23-c (500 mg, 3.24 mmol), chloroacetone (0.52 mL, 6.49 mmol) and ethanol (20 mL) were added to a reaction flask. The reaction solution was heated to reflux and stirred overnight. After the reaction was completed and concentrated, the crude product was separated by silica gel column chromatography (PE:EA=5:1) to obtain product 23-b (0.55 g, 88%) as a white solid. LC-MS (ESI): m/z=193.0 [M+H]$^+$.

Synthesis of Compound 23-a

Pyridine (93 mg, 1.17 mmol) and 23-b (150 mg, 0.78 mmol) was dissolved in dichloromethane (10 mL), cooled in ice water bath, and trifluoromethanesulfonic anhydride (0.2 mL, 1.17 mmol) was slowly added. The mixture was stirred at room temperature overnight. Water (10 mL) was added, and the organic layer was separated. The aqueous layer was extracted with dichloromethane (10 mL*2). The combined organic phase was dried over anhydrous sodium sulfate, concentrated, and purified by column chromatography (PE:EA=5:1) to obtain compound 23-a (150 mg, 59%). LC-MS (ESI): m/z=325.0 [M+H]$^+$.

Synthesis of Compound 23

23-a (150 mg, 0.46 mmol), 17-c (94.8 mg, 0.46 mmol), [1,1'-bis(diphenylphosphino)ferrocene]dichloropalladium (II) (33.8 mg, 0.046 mmol), sodium carbonate (147.1 mg, 1.39 mmol), dioxane (10.0 mL) and water (2.0 mL) were added to a reaction flask. The reaction solution was replaced with $N_2$ and reacted at 85° C. overnight. After the reaction was completed, the solution was concentrated to obtain a crude product. The crude product was separated by high performance liquid preparative chromatography to obtain product 23 (75 mg, 48%) as a white solid. LC-MS (ESI): m/z=336.0 [M+H]+; $^1$H NMR (500 MHz, DMSO-$d_6$): δ 9.47 (s, 1H), 8.72 (dd, J=4.5, 1.5 Hz, 1H), 8.37 (s, 1H), 8.00 (brs, 1H), 7.97 (dd, J=7.5, 2.5 Hz, 1H), 7.65 (d, J=9.0 Hz, 1H), 7.60 (dd, J=8, 4.5 Hz, 1H), 7.40 (brs, 1H), 7.35 (dd, J=9.0, 1.5 Hz, 1H), 7.33 (s, 1H), 2.05 (s, 3H).

Synthetic Route of Compound 24

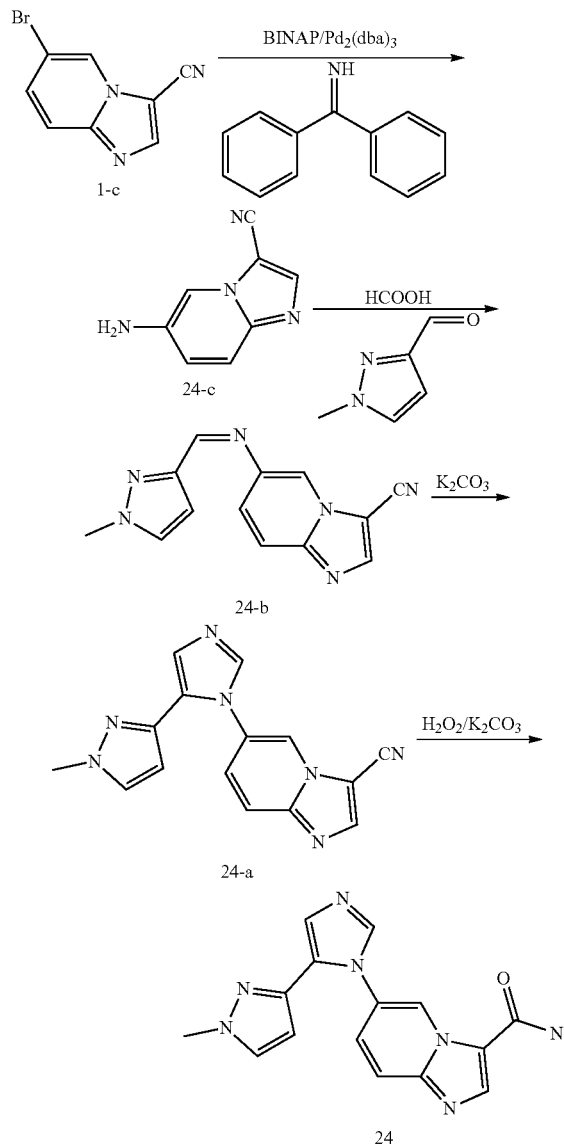

Synthesis of Compound 24-c

A mixture of compound 24-d (2.2 g, 10.0 mmol), benzophenonimine (1.8 g, 10.0 mmol), $Pd_2(dba)_3$ (0.23 g, 0.4 mmol), BINAP (0.25 g, 0.4 mmol), sodium tert-butoxide (2.0 g, 20.0 mmol) and toluene (100 mL) was heated to 100° C. and reacted for 1 hour under nitrogen atmosphere. The reaction was cooled to room temperature and concentrated. Dilute hydrochloric acid (100 mL, 300 mmol) and ethyl acetate (30 mL*3) were added for extraction. The aqueous phase was basified to pH to 8 by aqueous sodium bicarbonate solution, filtered and the filter cake was dried to obtain 24-c (1.28 g, 80%) as a gray solid. LC-MS (ESI): m/z=159.1 [M+H]+.

Synthesis of Compound 24-b

A mixture of compound 24-c (0.16 g, 1.0 mmol), methanol (20 mL), 1-methylpyrrole-3-carbaldehyde (0.14 g, 1.27 mmol) and formic acid (0.20 mL) was stirred at room temperature for 3 hours. The reaction solution was concentrated, and ethyl acetate (5 mL) and petroleum ether (30 mL) were added. The solution was filtered to obtain solid 24-b (0.25 g, 100%). LC-MS (ESI): m/z=251.1 [M+H]+.

Synthesis of Compound 24-a

A mixture of compound p-toluenesulfonylmethylisonitrile (0.38 g, 2.0 mmol), 24-b (0.25 g, 1.0 mmol), potassium carbonate (0.28 g, 2.0 mmol), DME (4 mL) and DMF (10 mL) was heated to 100° C. for 12 hours in a sealed tube under nitrogen atmosphere. The reaction was cooled to room temperature and concentrated, then washed with ethyl acetate (300 mL). After filtration, the solution was concentrated to obtain compound 24-a, which was directly used in the next step. LC-MS (ESI): m/z=290.2 [M+H]+.

Synthesis of Compound 24

30% $H_2O_2$ (3 mL) was slowly added dropwise to a mixture of compound 24-a (0.14 g, 0.5 mmol), DMSO (4 mL) and potassium carbonate (0.138 g, 1.0 mmol) at 0° C. After reacting for 3 hours, the solution was concentrated, then diluted with water (10 mL) and filtered. The filter cake was slurried with ethyl acetate (10 mL) to obtain 24 (0.059 g, 38%) as a gray solid. LC-MS (ESI): m/z=308.0 [M+H]+; $^1$H NMR (500 MHz, MeOD): δ 9.72 (d, J=1.5 Hz, 1H), 8.38 (s, 1H), 8.02 (s, 1H), 7.75 (d, J=9.5 Hz, 1H), 7.53 (d, J=2.0 Hz, 1H), 7.48 (dd, J=9.5, 2.0 Hz, 1H), 7.39 (s, 1H), 6.17 (d, J=2.5 Hz, 1H), 3.81 (s, 3H).

Synthetic Route of Compound 25

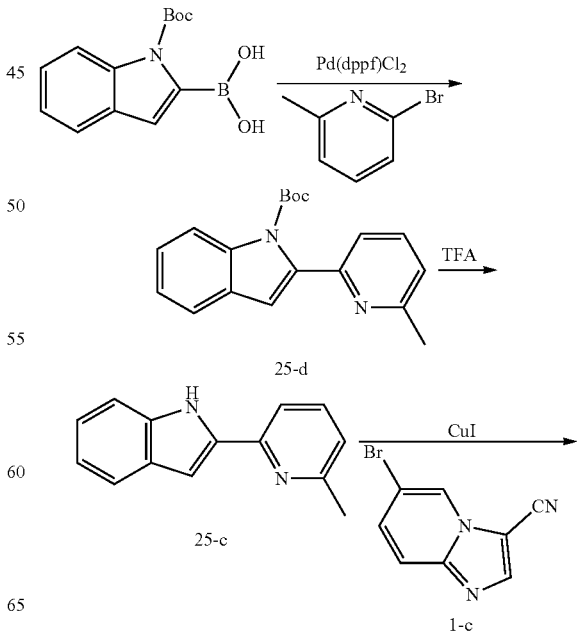

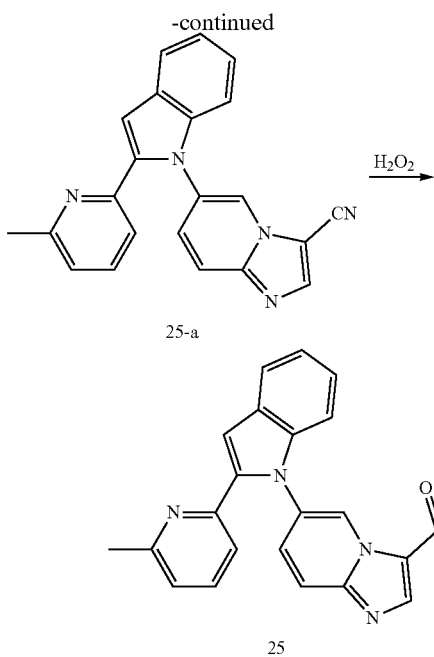

Synthesis of Compound 25

Under ice bath, hydrogen peroxide (19.5 mg, 0.57 mmol) was added dropwise to a solution of 25-a (50 mg, 0.143 mmol) and potassium carbonate (3 mg, 0.021 mmol) in dimethyl sulfoxide (2 mL). The mixture was raised to room temperature and stirred overnight. After the reaction was completed, water (5 mL) was slowly added to quench the reaction. The solution was stirred for half an hour and white precipitate was precipitated. After filtration, the solid was collected and dried to obtain compound 25 (10 mg, 19%) as a white solid. LC-MS (ESI): m/z=368.0 [M+H]$^+$; $^1$H NMR (500 MHz, MeOD): δ 9.62 (d, J=1.5 Hz, 1H), 8.38 (s, 1H), 7.72-7.77 (m, 2H), 7.66 (t, J=7.5 Hz, 1H), 7.50 (d, J=8.0 Hz, 1H), 7.47 (dd, J=9.5, 2.0 Hz, 1H), 7.30 (d, J=8.5 Hz, 1H), 7.26 (t, J=7.0 Hz, 1H), 7.22 (t, J=8.0 Hz, 1H), 7.18 (s, 1H), 7.09 (d, J=8.0 Hz, 1H), 2.23 (s, 3H).

Synthetic Route of Comparative Compound 12

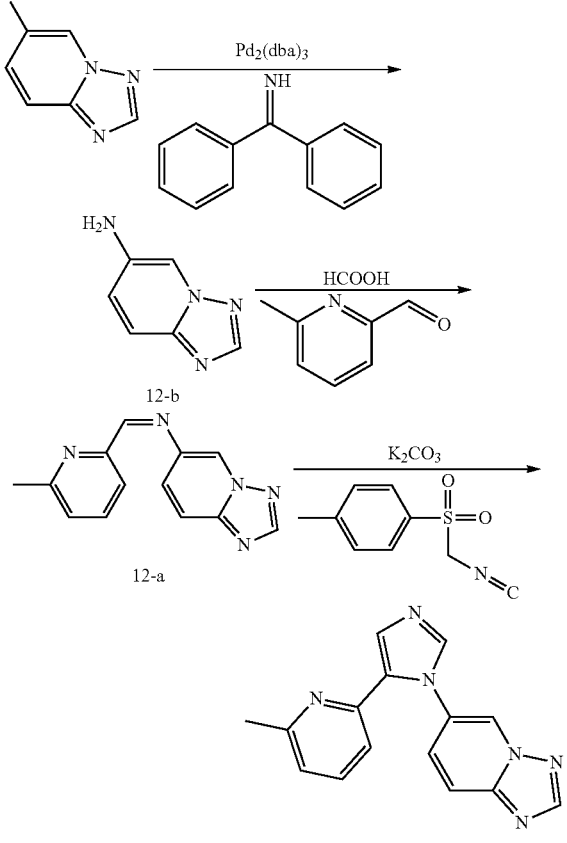

Synthesis of Compound 25-d

Boc-indole-2-boronic acid (1.4 g, 5.36 mmol), 2-bromo-6-methylpyridine (922 mg, 5.36 mmol), Pd(dppf)Cl$_2$ (438 mg, 0.54 mmol), sodium carbonate (1.7 g, 16.08 mmol), dioxane (10 mL) and water (2 mL) were added to a reaction flask. The reaction solution was replaced with N$_2$ and reacted at 85° C. overnight. After the reaction was completed, the reaction solution was diluted with ethyl acetate, washed successively with water and saturated brine, dried over anhydrous sodium sulfate. After filtration, the solution was dried by rotary evaporation. The crude product was separated by silica gel column chromatography (PE:EA=10:1) to obtain the product 25-d (1 g, 60%) as a white solid. LC-MS (ESI): m/z=309.1 [M+H]$^+$.

Synthesis of Compound 25-c 25-d (1 g, 3.24 mmol) was dissolved in dichloromethane (20 mL) and trifluoroacetic acid (10 mL), and the mixture was stirred at room temperature overnight. After the reaction was completed, the organic solvent was removed through concentration under reduced pressure, saturated aqueous sodium bicarbonate solution (10 mL) and DCM (10 mL) were added, and the solution was separated. The aqueous layer was extracted with dichloromethane, and the organic layers were combined, dried over anhydrous sodium sulfate, filtered, and concentrated to obtain 25-c (400 mg, 59%) as a white solid. LC-MS (ESI): m/z=209.1 [M+H]$^+$.

Synthesis of Compound 25-a

Compound 25-c (50 mg, 0.24 mmol), 1-c (53.3 mg, 0.24 mmol), cuprous iodide (5 mg, 0.024 mmol), N,N'-dimethyl-1,2-ethanediamine (4.2 mg, 0.048 mmol), potassium phosphate (102 mg, 0.48 mmol) and toluene (2 mL) were added to a reaction flask. The reaction solution was replaced with N$_2$ and stirred at 110° C. overnight. After the reaction was completed, it was diluted with ethyl acetate, washed successively with water and saturated brine, dried over anhydrous sodium sulfate. After filtration, the solution was dried by rotary evaporation. The crude product was separated by silica gel column chromatography (PE:EA=1:1) to obtain compound 25-a (50 mg, 60%) as a white solid. LC-MS (ESI): m/z=350.1 [M+H]$^+$.

Synthesis of Compound 12-b

Compound 6-bromo-[1,2,4]triazolo[1,5-a]pyridine (0.7 g, 3.54 mmol), benzophenonimine (961 mg, 5.30 mmol), sodium tert-butoxide (679.5 mg, 7.07 mmol), Pd$_2$(dba)$_3$ (162 mg, 0.18 mmol), 1,1'-binaphthalene-2,2'-bisdiphenylphosphine (220 mg, 0.35 mmol) and toluene (40 mL) were added to a reaction flask. The reaction solution was replaced with N$_2$ and stirred at 100° C. for one hour. After the reaction was completed, the reaction solution was diluted with ethyl acetate, washed successively with water and saturated brine, dried over anhydrous sodium sulfate, filtered, and dried by rotary evaporation to obtain a black oil. Dilute hydrochloric acid (2 M, 10 mL) was added to the black oil, the solution was stirred for half an hour, then neutralized with solid sodium bicarbonate to pH>7 and extracted with dichloromethane. The organic phase was dried, concentrated, and the resulting crude product was purified by silica gel column chromatography to obtain 12-b (0.3 g, 63%) as a brown solid. LC-MS (ESI): m/z=135.1 [M+H]$^+$.

Synthesis of Compound 12-a

Compound 6-methyl-2-pyridinecarboxaldehyde (45 mg, 0.37 mmol), 12-b (50 mg, 0.37 mmol), methanol (10 mL) and a few drops of formic acid were added to a reaction flask. The reaction solution was stirred at room temperature overnight. After the reaction was completed, the solid was washed with ethyl acetate and dried to obtain product 12-a (50 mg, 56%) as a white solid. LC-MS (ESI): m/z=238.1 [M+H]$^+$.

Synthesis of Comparative Compound 12

Compound 12-a (50 mg, 0.21 mmol), p-toluenesulfonylmethylisonitrile (62 mg, 0.32 mmol), potassium carbonate (61 mg, 0.44 mmol), DMF (4.6 mL) and ethylene glycol dimethyl ether (3.75 mL) were added to a reaction flask. The reaction solution was replaced with $N_2$ and stirred at 100° C. overnight. After the reaction was completed, the mixture was filtered, and the filtrate was subjected to high performance liquid preparative chromatography to obtain solid 12 (15 mg, 26%). LC-MS (ESI): m/z=277.1 [M+H]$^+$; $^1$H NMR (500 MHz, MeOD): δ 9.16 (s, 1H), 8.54 (s, 1H), 8.10 (s, 1H), 7.82 (d, J=9.5, 1H), 7.69 (t, J=8.0 Hz, 1H), 7.62-7.66 (m, 2H), 7.49 (d, J=8.0 Hz, 1H), 7.11 (t, J=7.5 Hz, 1H), 2.27 (s, 3H).

Effect Embodiment 1 Evaluation Experiment of ALK5 Enzyme Activity Inhibition $IC_{50}$ 1×kinase buffer preparation: 40 mM Tris (pH 7.5), 20 mM $MgCl_2$, 0.10% BSA, 1 mM DTT.

Compound preparation: The final detection concentration of the compound was 10 μM, which was configurated to a 100-fold concentration, i.e., 1 mM. In the second well of the 384-well plate, 100 μL of 100-fold compound was added, and 60 μL of 100% DMSO was added to other wells. 30 μL of compound from the second well was taken and added to the third well, and a 3-fold dilution was made in sequence, a total of 10 concentrations were diluted. 50 nL of compound was transferred to the reaction plate with echo.

Kinase reaction: Kinase was added to 1×kinase buffer to form a 2×enzyme solution. The final concentration of kinase solution was ALK5:25 nM. The polypeptide TGFbR1 (purchased from Signal Chem, catalog number T36-58) and ATP were added to 1×kinase buffer to form a 2×substrate solution. The final concentration of the substrate solution was 0.1 mg/mL peptide TGFbR1, 7 μM ATP. 2.5 μL of 2×enzyme solution was added to the 384-well reaction plate (there was already 50 nL of 100% DMSO dissolved compound), and 1×kinase buffer was added to the negative control well. The plate was incubated at room temperature for 10 minutes. 2.5 μL of 2× substrate solution was added to the 384-well reaction plate. The 384-well plate was covered and incubated at 30° C. for 1 hour. ADP-Glo reagent (purchased from Promege, catalog number v9102) was equilibrated to room temperature. 5 μL of ADP-Glo reagent was transferred to the reaction well of the 384-well plate to stop the reaction.

Detection of reaction results: 10 μL of kinase detection reagent was transferred to each reaction well, the plate was shaken for 1 minute and placed at room temperature for 30 minutes. The sample luminescence value was read at Synegy.

Curve fitting: The data of the luminescence reading from the Synegy program were copied. The value of the luminescence reading was converted into the percentage of inhibition by a formula (inhibition percent=(max-sample RLU)/(max-min)*100, wherein "min" was a fluorescence reading of the control sample without enzyme; "max" was the fluorescence reading of sample with DMSO as a control). The data were imported into MS Excel and GraphPad Prism was used for curve fitting. The IC$_{50}$ value was calculated.

TABLE 1

$IC_{50}$ results of some compounds of the present invention on ALK5 activity

| Compound No. | ALK5 $IC_{50}$ (nM) | Compound No. | ALK5 $IC_{50}$ (nM) |
| --- | --- | --- | --- |
| SB431542 | 108 | 1 | 13 |
| 4 | 19 | 5 | 105 |
| 8 | 7 | 9 | 136 |
| 16 | 165 | 17 | 5.2 |
| 18 | 9.4 | 19 | 75 |
| 20 | 76 | 23 | 21 |
| 25 | 14 | Comparative compounds 12 | 6111 |
| Comparative compounds 10 | >10000 | / | / |

Wherein, SB431542 (CAS number: 301836-41-9) is a known ALK5 inhibitor, and its structure is as follows:

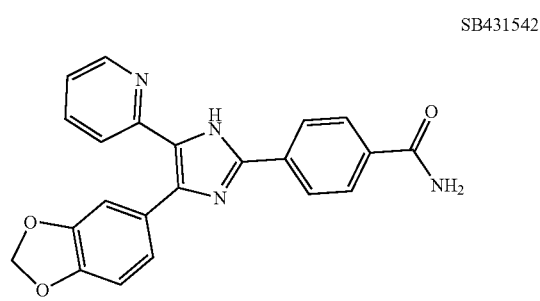 [SMILES: NC(=O)c1ccc(-c2nc(-c3ccc4c(c3)OCO4)c(-c3ccccn3)[nH]2)cc1]

SB431542

From the results of the above test, it can be confirmed that the compounds of the present invention have a significant inhibitory effect on ALK5 activity.

Although the specific embodiments of the present invention have been described above, those skilled in the art should understand that these are only illustrative examples, and various changes or modification can be made to these embodiments without departing from the principle and essence of the present invention. Therefore, the protection scope of the present invention is defined by the appended claims.

The invention claimed is:

1. An aromatic heterocyclic compound represented by the general formula I or a pharmaceutically acceptable salt thereof:

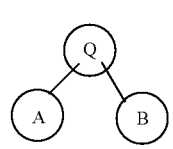

I wherein,

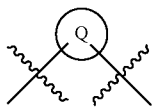

is

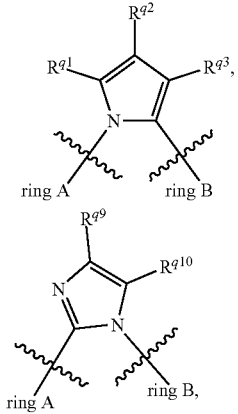
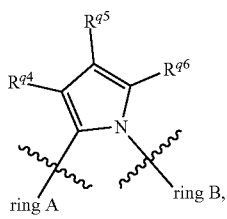
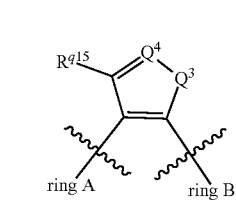

or

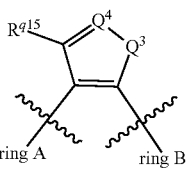

in ring Q, $R^{q1}$, $R^{q2}$, $R^{q3}$, $R^{q4}$, $R^{q5}$, $R^{q6}$, $R^{q9}$, $R^{q10}$, and $R^{q15}$ are each independently hydrogen, deuterium, halogen, sulfonic acid group, substituted or unsubstituted $C_{1-6}$ alkyl, substituted or unsubstituted $C_{2-8}$ alkenyl, substituted or unsubstituted $C_{2-8}$ alkynyl, substituted or unsubstituted $C_{3-10}$ cycloalkyl, substituted or unsubstituted $C_{2-8}$ heterocycloalkyl, substituted or unsubstituted $C_{6-20}$ aryl, substituted or unsubstituted $C_{2-10}$ heteroaryl, cyano, cyano, —$OR^{61}$, —$SR^{62}$, —$NR^{a63}R^{a64}$, —$C(O)R^{65}$, —$C(O)OR^{66}$, —$OC(O)R^{67}$, —$OC(O)OR^{68}$, —$C(O)NR^{a69}R^{a610}$, —$N(R^{611})C(O)R^{612}$, $S(O)R^{613}$, —$S(O)_2R^{614}$, —$S(O)_2NR^{a615}R^{a616}$, —$OC(O)NR^{a617}R^{a618}$, —$N(R^{619})C(O)OR^{620}$, —$N(R^{621})C(O)NR^{a622}R^{a623}$, —$N(R^{624})S(O)_2R^{625}$ or —$OP(O)(OR^{626})_2$; $R^{61}$, $R^{62}$, $R^{a63}$, $R^{a64}$, $R^{65}$, $R^{66}$, $R^{67}$, $R^{68}$, $R^{a69}$, $R^{a610}$, $R^{611}$, $R^{612}$, $R^{613}$, $R^{614}$, $R^{a615}$, $R^{a616}$, $R^{a617}$, $R^{a618}$, $R^{619}$, $R^{620}$, $R^{621}$, $R^{a622}$, $R^{a623}$, $R^{624}$, $R^{625}$ and $R^{626}$ are each independently hydrogen, substituted or unsubstituted $C_{1-6}$ alkyl, substituted or unsubstituted $C_{2-8}$ alkenyl, substituted or unsubstituted $C_{2-8}$ alkynyl, substituted or unsubstituted $C_{3-10}$ cycloalkyl, substituted or unsubstituted $C_{2-8}$ heterocycloalkyl, substituted or unsubstituted $C_{6-20}$ aryl, or substituted or unsubstituted $C_{2-10}$ heteroaryl;

in $R^{q1}$, $R^{q2}$, $R^{q3}$, $R^{q4}$, $R^{q5}$, $R^{q6}$, $R^{q9}$, $R^{q10}$ and $R^{q15}$, substituents in the substituted $C_{1-6}$ alkyl, substituted $C_{2-8}$ alkenyl, substituted $C_{2-8}$ alkynyl, substituted $C_{3-10}$ cycloalkyl, substituted $C_{2-8}$ heterocycloalkyl, substituted $C_{6-20}$, substituted aryl or substituted $C_{2-10}$ heteroaryl are each independently one or more of the following groups: deuterium, halogen, $C_{1-6}$ alkyl, halogen substituted $C_{1-6}$ alkyl, $C_{2-8}$ alkenyl, $C_{2-8}$ alkynyl, $C_{3-10}$ cycloalkyl, $C_{2-8}$ heterocycloalkyl, $C_{6-20}$ aryl, $C_{2-10}$ heteroaryl, cyano, —$OR^{71}$, —$SR^{72}$, —$NR^{a73}R^{a74}$, —$C(O)R^{75}$, —$C(O)OR^{76}$, —$OC(O)R^{77}$, —$OC(O)OR^{78}$, —$C(O)NR^{a79}R^{a710}$, —$N(R^{711})C(O)R^{712}$, $S(O)R^{713}$, —$S(O)_2R^{714}$, —$S(O)_2NR^{a715}R^{a716}$, —$OC(O)NR^{a717}R^{a718}$, —$N(R^{719})C(O)OR^{720}$, —$N(R^{721})C(O)NR^{a722}R^{a723}$, —$N(R^{724})S(O)_2R^{725}$ or —$OP(O)(OR^{726})_2$; when there are multiple substituents, the substituents are the same or different; $R^{71}$, $R^{72}$, $R^{a73}$, $R^{a74}$, $R^{75}$, $R^{76}$, $R^{77}$, $R^{78}$, $R^{a79}$, $R^{a710}$, $R^{711}$, $R^{712}$, $R^{713}$, $R^{714}$, $R^{a715}$, $R^{a716}$, $R^{a717}$, $R^{a718}$, $R^{719}$, $R^{720}$, $R^{721}$, $R^{a722}$, $R^{a723}$, $R^{724}$, $R^{725}$ and $R^{726}$ are each independently $C_{1-6}$ alkyl, halogen substituted $C_{1-6}$ alkyl, $C_{2-8}$ alkenyl, $C_{2-8}$ alkynyl, $C_{3-10}$ cycloalkyl, $C_{2-8}$ heterocycloalkyl, $C_{6-20}$ aryl or $C_{2-10}$ heteroaryl;

in $R^{61}$, $R^{62}$, $R^{a63}$, $R^{a64}$, $R^{65}$, $R^{66}$, $R^{67}$, $R^{68}$, $R^{a69}$, $R^{a610}$, $R^{611}$, $R^{612}$, $R^{613}$, $R^{a614}$, $R^{a615}$, $R^{a616}$, $R^{a617}$, $R^{a618}$, $R^{619}$, $R^{620}$, $R^{621}$, $R^{a622}$, $R^{a623}$, $R^{624}$, $R^{625}$ and $R^{626}$, substituents in the substituted $C_{1-6}$ alkyl, substituted $C_{2-8}$ alkenyl, substituted $C_{2-8}$ alkynyl, substituted $C_{3-10}$ cycloalkyl, substituted $C_{2-8}$ heterocycloalkyl, substituted $C_{6-20}$ aryl or substituted $C_{2-10}$ heteroaryl are each independently one or more of the following groups: deuterium, halogen, cyano, $C_{1-6}$ alkyl, halogen substituted $C_{1-6}$ alkyl, $C_{2-8}$ alkenyl, $C_{2-8}$ alkynyl, $C_{3-10}$ cycloalkyl, $C_{2-8}$ heterocycloalkyl, $C_{6-20}$ aryl, $C_{2-10}$ heteroaryl, —$OR^c$—$SR^{c1}$, —$NR^{b1}R^{b2}$, —$C(O)R^{c2}$, —$C(O)OR^{c3}$, —$OC(O)R^{c4}$, —$OC(O)OR^{c5}$, —$C(O)NR^{b3}R^{b4}$, —$N(R^{c6})C(O)OR^{c7}$, $S(O)R^{c8}$, —$S(O)_2R^{c9}$, —$S(O)_2NR^{b5}R^{b6}$, —$N(R^{c10})C(O)R^{c11}$, —$N(R^{c12})C(O)NR^{b7}R^{b8}$ or —$N(R^{c13})S(O)_2R^{c14}$; $R^c$, $R^{c1}$, $R^{b1}$, $R^{b2}$, $R^{c2}$, $R^{c3}$, $R^{c4}$, $R^{c5}$, $R^{b3}$, $R^{b4}$, $R^{c6}$, $R^{c7}$, $R^{c8}$, $R^{c9}$, $R^{b5}$, $R^{b6}$, $R^{c10}$, $R^{c11}$, $R^{c12}$, $R^{b7}$, $R^{b8}$, $R^{c13}$ and $R^{c14}$ are each independently hydrogen, hydroxyl, $C_{1-6}$ alkyl, halogen substituted $C_{1-6}$ alkyl, $C_{3-10}$ cycloalkyl, $C_{2-8}$ heterocycloalkyl, $C_{6-20}$ aryl or $C_{2-10}$ heteroaryl;

$Q^3$ is S;

$Q^4$ is $CR^{q23}$; $R^{q23}$ and $R^{q1}$ have the same definition;

or two adjacent $R^{qx}$ and the atoms to which they are connected form a ring structure; the ring structure is substituted or unsubstituted $C_{3-10}$ cycloalkyl, substituted or unsubstituted $C_{2-8}$ heterocycloalkyl, substituted or unsubstituted $C_{6-20}$ aryl, or substituted or unsubstituted $C_{2-10}$ heteroaryl; in the ring structure, substituents in the substituted $C_{3-10}$ cycloalkyl, substituted $C_{2-8}$ heterocycloalkyl, substituted $C_{6-20}$ aryl or substituted $C_{2-10}$ heteroaryl are each independently one or more of the following groups: deuterium, halogen, cyano, $C_{1-6}$ alkyl, halogen substituted $C_{1-6}$ alkyl, $C_{2-8}$ alkenyl, $C_{2-8}$ alkynyl, —$OR^{a15}$, —$SR^{a16}$, —$C(O)OR^{a17}$, —$COR^{a18}$, —$C(O)NH_2$, $C_{3-10}$ cycloalkyl, $C_{2-8}$ heterocycloalkyl, $C_{6-20}$ aryl, $C_{2-10}$ heteroaryl; $R^{a15}$, $R^{a16}$, $R^{a17}$ and $R^{a18}$ are each independently hydrogen or $C_{1-6}$ alkyl; when there are multiple substituents, the substituents are the same or different;

the two adjacent $R^{qx}$ refer to $R^{q1}$ and $R^{q2}$; $R^{q2}$ and $R^{q3}$; $R^{q4}$ and $R^{q5}$; $R^{q5}$ and $R^{q6}$; $R^{q9}$ and $R^{q10}$; when $Q^4$ is $CR^{q23}$, two adjacent $R^{qx}$ can also be $R^{q15}$ and $R^{q23}$;

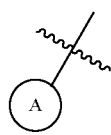

is

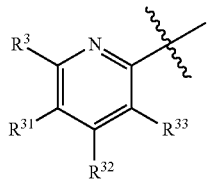

in ring A, $R^3$, $R^{31}$, $R^{32}$ and $R^{33}$ are each independently hydrogen, halogen, cyano, nitro, —$NR^{a3}R^{a4}$, —$OR^{a5}$, —$SR^{a6}$, —$C(O)OR^{a7}$, —$C(O)NR^{a8}R^{a9}$, —$COR^{a10}$, substituted or unsubstituted $C_{1-6}$ alkyl, substituted or unsubstituted $C_{2-8}$ alkenyl, substituted or unsubstituted $C_{2-8}$ alkynyl, substituted or unsubstituted $C_{3-10}$ cycloalkyl, substituted or unsubstituted $C_{2-8}$ heterocycloalkyl, substituted or unsubstituted $C_{4-8}$ cycloalkenyl, substituted or unsubstituted $C_{6-20}$ aryl, or substituted or unsubstituted $C_{2-10}$ heteroaryl;

$R^{a4}$, $R^{a5}$, $R^{a6}$, $R^{a7}$, $R^{a9}$ and $R^{a10}$ are each independently hydrogen, substituted or unsubstituted $C_{1-6}$ alkyl, $C_{2-8}$ alkenyl, $C_{2-8}$ alkynyl, $C_{3-10}$ cycloalkyl, $C_{2-8}$ heterocycloalkyl, $C_{6-20}$ aryl or $C_{2-10}$ heteroaryl; $R^{a3}$ and $R^{a8}$ are each independently hydrogen, hydroxyl, $C_{1-6}$ alkoxy, substituted or unsubstituted $C_{1-6}$ alkyl, $C_{2-8}$ alkenyl, $C_{2-8}$ alkynyl, $C_{3-10}$ cycloalkyl, $C_{2-8}$ heterocycloalkyl, $C_{6-20}$ aryl or $C_{2-10}$ heteroaryl;

in $R^3$, $R^{31}$, $R^{32}$, and $R^{33}$, substituents in the substituted $C_{1-6}$ alkyl, substituted $C_{2-8}$ alkenyl, substituted $C_{2-8}$ alkynyl, substituted $C_{3-10}$ cycloalkyl, substituted $C_{2-8}$ heterocycloalkyl, substituted $C_{4-8}$ cycloalkenyl, substituted $C_{6-20}$ aryl or substituted $C_{2-10}$ heteroaryl, and substituents in the substituted $C_{1-6}$ alkyl in $R^{a3}$, $R^{a4}$, $R^{a5}$, $R^{a6}$, $R^{a7}$, $R^{a8}$, $R^{a9}$ and $R^{a10}$ are each independently one or more of the following groups: deuterium, halogen, cyano, $C_{1-6}$ alkyl, halogen substituted $C_{1-6}$ alkyl, $C_{2-8}$ alkenyl, $C_{2-8}$ alkynyl, —$OR^{a15}$, —$SR^{a16}$, —$C(O)OR^{a17}$, —$COR^{a18}$, —$C(O)NH_2$, $C_{3-10}$ cycloalkyl, $C_{2-8}$ heterocycloalkyl, $C_{6-20}$ aryl or $C_{2-10}$ heteroaryl; $R^{a15}$, $R^{a16}$, $R^{a17}$ and $R^{a18}$ are each independently hydrogen or $C_{1-6}$ alkyl; when there are multiple substituents, the substituents are the same or different;

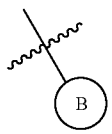

is

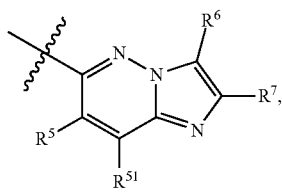

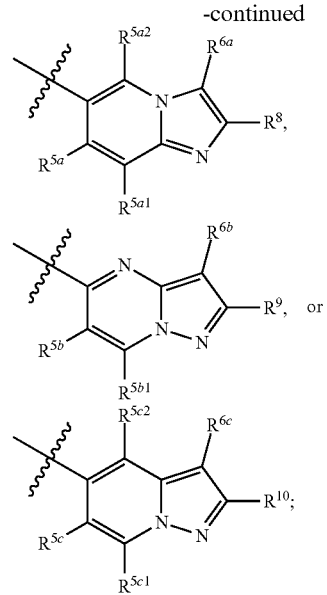

in ring B, $R^5$, $R^{51}$, $R^{5a}$, $R^{5a1}$, $R^{5a2}$, $R^{5b}$, $R^{5b1}$, $R^{5c}$, $R^{5c1}$, and $R^{5c2}$ are each independently hydrogen, deuterium or halogen;

$R^6$, $R^{6a}$, $R^{6b}$, and $R^{6c}$ are each independently halogen, —$C(O)OR^{66}$ or —$C(O)NR^{a69}R^{a610}$; $R^{66}$ is hydrogen or $C_{1-6}$ alkyl; $R^{a69}$ and $R^{a610}$ are hydrogen;

$R^7$, $R^8$, $R^9$, and $R^{10}$ are each independently hydrogen, deuterium or halogen; or in the above groups or substituents, when $NR^XR^Y$ is present, then $R^X$, $R^Y$ and N to which they are attached form substituted or unsubstituted 3-8 membered heterocyclyl together; heteroatom in the 3-8 membered heterocyclyl is selected from N, N and O, N and S, or N, O and S; the number of heteroatom is 1, 2, 3 or 4; substituents in the substituted 3-8 membered heterocyclyl are one or more of the following groups: deuterium, halogen, cyano, $C_{1-6}$ alkyl, $C_{2-8}$ alkenyl, $C_{2-8}$ alkynyl, —$OR^{a81}$, —$SR^{a82}$, —$C(O)OR^{a83}$, —$COR^{a84}$, —$C(O)NH_2$, $C_{3-10}$ cycloalkyl, $C_{2-8}$ heterocycloalkyl, $C_{6-20}$ aryl or $C_{2-10}$ heteroaryl; $R^{a81}$, $R^{a82}$, $R^{a83}$ and $R^{a84}$ are each independently hydrogen or $C_{1-6}$ alkyl; —$NR^XR^Y$ is —$NR^{a3}R^{a4}$, —$NR^{a8}R^{a9}$, —$NR^{a63}R^{a64}$, —$NR^{a69}R^{a610}$, —$NR^{a615}R^{a616}$, —$NR^{a617}R^{a618}$, —$NR^{a622}R^{a623}$, —$NR^{a73}R^{a74}$, —$NR^{a79}R^{a710}$, —$NR^{a715}R^{a716}$, —$NR^{a717}R^{a718}$, —$NR^{a722}R^{a723}$, —$NR^{b1}R^{b2}$, —$NR^{b3}R^{b4}$, —$NR^{b5}R^{b6}$ or —$NR^{b7}R^{b8}$.

2. The aromatic heterocyclic compound represented by the general formula I or the pharmaceutically acceptable salt thereof as defined in claim 1, wherein the halogen is F, Cl, Br or I;

or, the $C_{1-6}$ alkyl in the substituted or unsubstituted $C_{1-6}$ alkyl and the $C_{1-6}$ alkyl are independently $C_{1-4}$ alkyl;

or, the $C_{2-8}$ alkenyl in the substituted or unsubstituted $C_{2-8}$ alkenyl and the $C_{2-8}$ alkenyl are independently $C_{2-4}$ alkenyl;

or, the $C_{2-8}$ alkynyl in the substituted or unsubstituted $C_{2-8}$ alkynyl and the $C_{2-8}$ alkynyl are independently $C_{2-4}$ alkynyl;

or, the $C_{3-10}$ cycloalkyl in the substituted or unsubstituted $C_{3-10}$ cycloalkyl and the $C_{3-10}$ cycloalkyl are independently cyclopropyl, cyclobutyl, cyclopentyl, cyclohexyl, cycloheptyl, cyclooctyl, cyclononyl, cyclodecyl, bicyclo [3.1.1] heptyl, bicyclo [2.2.1] heptyl, bicyclo [2.2.2] octyl, bicyclo [3.2.2] nonyl, bicyclo [3.3.1] nonyl or bicyclo [4.2.1] nonyl;

or, the $C_{2-8}$ heterocycloalkyl in the substituted or unsubstituted $C_{2-8}$ heterocycloalkyl and the $C_{2-8}$ heterocycloalkyl are independently azetidinyl, azepanyl, aziridine, diazcycloheptyl, 1,3-dioxanyl, 1,3-dioxopenyl, 1,3-dithiopentyl, 1,3-dithianyl, imidazolinyl, imidazolidinyl, isothiazolidinyl, isothiazolyl, isoxazolinyl, morpholinyl, oxadiazolinyl, oxadiazolidinyl, oxazolinyl, oxazolidinyl, piperazinyl, piperidinyl, pyranyl, pyrazolinyl, pyrazolidinyl, pyrrolinyl, pyrrolidinyl, tetrahydrofuranyl, tetrahydrothienyl, thiadiazolinyl, thiadiazolidinyl, thiazolinyl, thiazolidinyl, thiomorpholinyl, 1,1-dioxothiomorpholinyl, thiopyranyl, trithianyl, 2,3-dihydrobenzofuran-2-yl, 2,3-dihydrobenzofuran-3-yl, indoline-1-yl, indoline-2-yl, indoline-3-yl, 2,3-dihydrobenzothiophene-2-yl, decahydroquinolinyl, decahydroisoquinolinyl, octahydro-1H-indolyl or octahydrobenzofuranyl;

or, the $C_{4-8}$ cycloalkenyl in the substituted or unsubstituted $C_{4-8}$ cycloalkenyl and the $C_{4-8}$ cycloalkenyl are independently cyclobutenyl, cyclopentenyl, cyclohexenyl, cycloheptenyl, cyclooctenyl, norbornenyl or bicyclo [2.2.2] octenyl;

or, the $C_{6-20}$ aryl in the substituted or unsubstituted $C_{6-20}$ aryl or the $C_{6-20}$ aryl are independently phenyl, naphthyl, anthryl, phenanthryl, azulenyl, indan-1-yl, indan-2-yl, indan-3-yl, indan-4-yl, 2,3-indoline-4-yl, 2,3-indoline-5-yl, 2,3-indoline-6-yl, 2,3-indoline-7-yl, inden-1-yl, inden-2-yl, inden-3-yl, inden-4-yl, dihydronaphthalene-2-yl, dihydronaphthalene-3-yl, dihydronaphthalene-4-yl, dihydronaphthalene-1-yl, 5,6,7,8-tetrahydronaphthalene-1-yl, 5,6,7,8-tetrahydronaphthalene-2-yl, 2,3-dihydrobenzofuran-4-yl, 2,3-dihydrobenzofuran-5-yl, 2,3-dihydrobenzofuran-6-yl, 2,3-dihydrobenzofuran-7-yl, benzo[d][1,3]dioxol-4-yl, benzo[d][1,3]dioxol-5-yl, 2H-benzofuran-2-one-5-yl, 2H-benzofuran-2-one-6-yl, 2H-benzofuran-2-one-7-yl, 2H-benzofuran-2-one-8-yl, isoindoline-1,3-dione-4-yl, isoindoline-1,3-dione-5-yl, inden-1-one-4-yl, inden-1-one-5-yl, inden-1-one-6-yl, inden-1-one-7-yl, 2,3-dihydrobenzo[b][1,4]dioxane-5-yl, 2,3-dihydrobenzo[b][1,4]dioxane-6-yl, 2H-benzo [b][1,4]oxazine3(4H)-one-5-yl, 2H-benzo [b][1,4] oxazine 3(4H)-one-6-yl, 2H-benzo [b][1,4] oxazine 3(4H)-one-7-yl, 2H-benzo [b][1,4]oxazine3(4H)-one-8-yl, benzo[d]oxazine-2(3H)-one-5-yl, benzo[d]oxazine-2(3H)-one-6-yl, benzo[d]oxazine-2(3H)-one-7-yl, benzo[d]oxazine-2(3H)-one-8-yl, quinazolin-4(3H)-one-5-yl, quinazolin-4(3H)-one-6-yl, quinazolin-4(3H)-one-7-yl, quinazolin-4(3H)-one-8-yl, quinoxalin-2(1H)-one-5-yl, quinoxalin-2(1H)-one-6-yl, quinoxaline-2(1H)-one-7-yl, quinoxaline-2(1H)-one-8-yl, benzo[d]thiazol-2(3H)-one-4-yl, benzo[d]thiazol-2(3H)-one-5-yl, benzo[d]thiazo-2(3H)-one-6-yl or benzo[d]thiazole-2(3H)-one-7-yl;

or, the $C_{2-10}$ heteroaryl in the substituted or unsubstituted $C_{2-10}$ heteroaryl and the $C_{2-10}$ heteroaryl are independently furanyl, imidazolyl, isoxazolyl, isothiazolyl, oxadiazolyl, oxazolyl, pyridyl, pyridazinyl, pyrimidinyl, pyrazinyl, pyrazolyl, pyrrolyl, tetrazolyl, thiadiazolyl, thiazolyl, thienyl, triazolyl, triazinyl, benzimidazolyl, benzofuranyl, benzothienyl, benzoxadiazolyl, benzothiazolyl, cinnolinyl, 5,6-dihydroquinolin-2-yl, 5,6-dihydroquinolin-1-yl, furopyridinyl, indazolyl, indolyl, isoquinolinyl, naphthyridinyl, purinyl, quinolinyl, 5,6,7,8-tetrahydroquinolin-2-yl, 5,6,7,8-tetrahydroquinolin-3-yl, 5,6,7,8-tetrahydroquinolin-4-yl, 5,6,7,8-tetrahydroisoquinolin-1-yl, thienopyridyl, 4,5,6,7-tetrahydro[c][1,2,5]oxadiazolyl or 6,7-dihydropyro[c][1,2,5]oxadiazol-4(5H) one.

3. The aromatic heterocyclic compound represented by the general formula I or the pharmaceutically acceptable salt thereof as defined in claim 1, wherein in ring Q, $R^{q1}$, $R^{q2}$, $R^{q3}$, $R^{q4}$, $R^{q5}$, $R^{q6}$, $R^{q9}$, $R^{q10}$, and $R^{q15}$ are each independently hydrogen, deuterium, halogen, sulfonic acid group, $C_{1-6}$ alkyl, $C_{2-8}$ alkenyl, $C_{2-8}$ alkynyl, $C_{3-10}$ cycloalkyl, $C_{2-8}$ heterocycloalkyl, $C_{6-20}$ aryl, $C_{2-10}$ heteroaryl, cyano, —$OR^{61}$, —$SR^{62}$, —$NR^{a63}R^{a64}$, —$C(O)R^{65}$, —$C(O)OR^{66}$, —$OC(O)R^{67}$, —$OC(O)OR^{68}$, —$C(O)NR^{a69}R^{a610}$, —$N(R^{611})C(O)R^{612}$, $S(O)R^{613}$, —$S(O)_2R^{614}$, —$S(O)_2NR^{a615}R^{a616}$, —$OC(O)NR^{a617}R^{a618}$, —$N(R^{619})C(O)OR^{620}$, —$N(R^{621})C(O)NR^{a622}R^{a623}$, —$N(R^{624})S(O)_2R^{625}$ or —$OP(O)(OR^{626})_2$;

or, in ring A, $R^3$, $R^{31}$, $R^{32}$, and $R^{33}$ are independently hydrogen, halogen, cyano, nitro, —$NR^{a3}R^{a4}$, —$OR^{a5}$, —$SR^{a6}$, —$C(O)OR^{a7}$, —$C(O)NR^{a8}R^{a9}$, —$COR^{a10}$, substituted or unsubstituted $C_{1-6}$ alkyl, substituted or unsubstituted $C_{2-8}$ heterocycloalkyl, substituted or unsubstituted $C_{6-20}$ aryl, or substituted or unsubstituted $C_{2-10}$ heteroaryl.

4. The aromatic heterocyclic compound represented by the general formula I or the pharmaceutically acceptable salt thereof as defined in claim 3, wherein in ring Q, $R^{q1}$, $R^{q2}$, $R^{q3}$, $R^{q4}$, $R^{q5}$, $R^{q6}$, $R^{q9}$, $R^{q10}$, and $R^{q15}$ are each independently hydrogen, deuterium, halogen or $C_{1-6}$ alkyl;

or, in ring A, $R^3$, $R^{31}$, $R^{32}$, and $R^{33}$ are each independently hydrogen, halogen, —$OR^{a5}$, —$SR^{a6}$, —$C(O)NR^{a8}R^{a9}$, or substituted or unsubstituted $C_{1-6}$ alkyl.

5. The aromatic heterocyclic compound represented by the general formula I or the pharmaceutically acceptable salt thereof as defined in claim 1, wherein in ring Q, $R^{q1}$, $R^{q2}$, $R^{q3}$, $R^{q4}$, $R^{q5}$, $R^{q6}$, $R^{q9}$, $R^{q10}$, and $R^{q15}$ are each independently hydrogen or $C_{1-6}$ alkyl;

or, in ring A, $R^3$, $R^{31}$, $R^{32}$, and $R^{33}$ are each independently hydrogen, halogen, trifluoromethyl, difluoromethyl, deuterated methyl, methyl or methoxy.

6. The aromatic heterocyclic compound represented by the general formula I or the pharmaceutically acceptable salt thereof as defined in claim 1, wherein

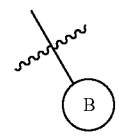

is

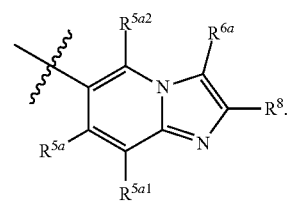

7. The aromatic heterocyclic compound represented by the general formula I or the pharmaceutically acceptable salt thereof as defined in claim 1, wherein ring Q is

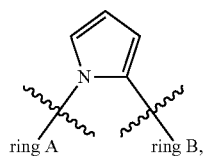 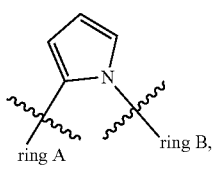

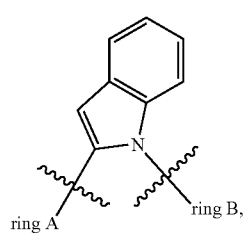 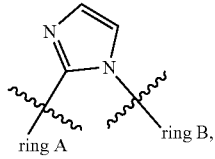

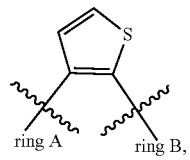 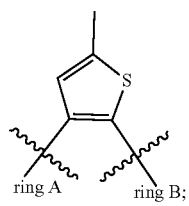

or,

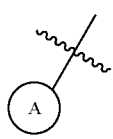

is

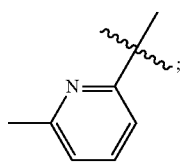 [SMILES: *c1cccc(C)n1]

or,

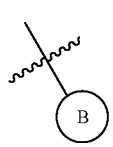

is

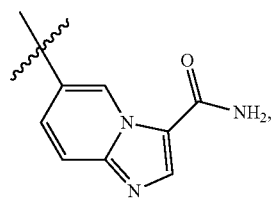

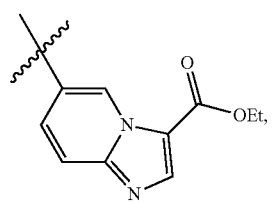

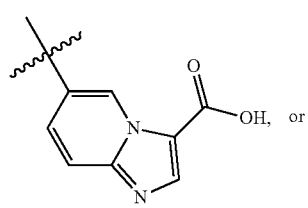

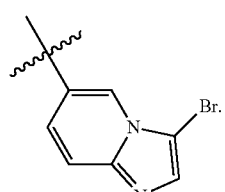

8. The aromatic heterocyclic compound represented by the general formula I or the pharmaceutically acceptable salt thereof as defined in claim 1, wherein the aromatic heterocyclic compound represented by the general formula I is any one of the following compounds:

1

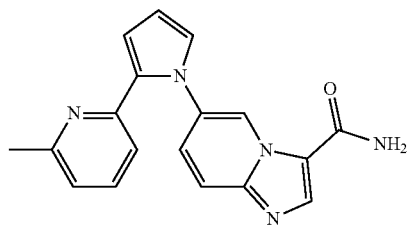

2

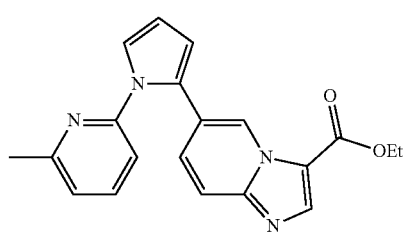

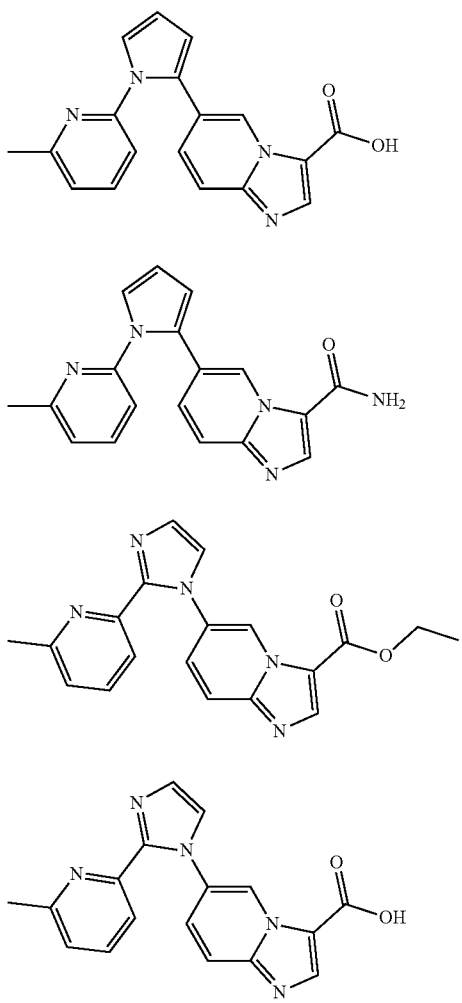

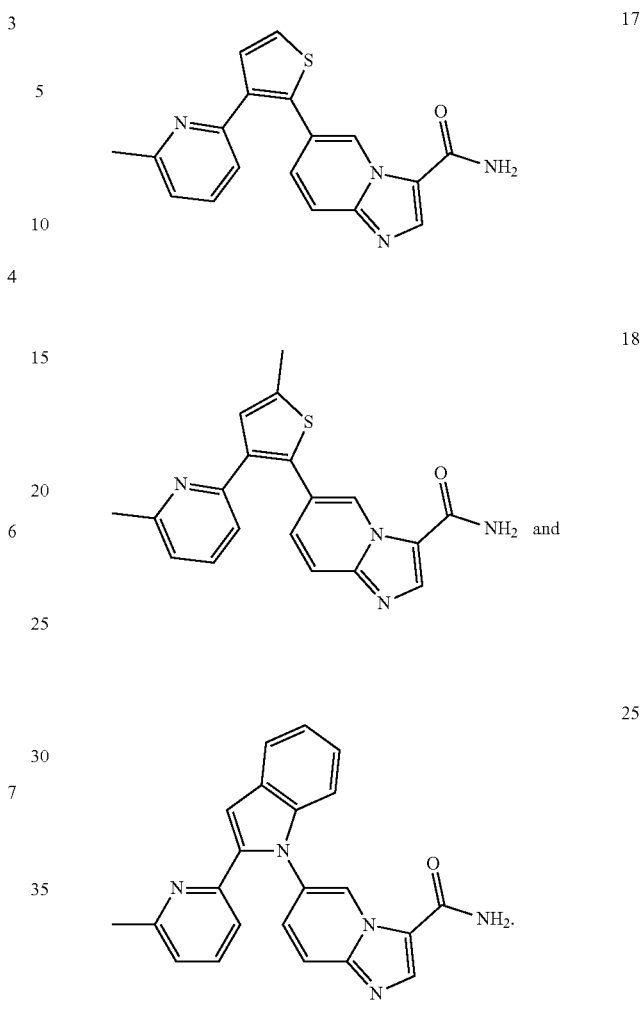

9. A method for preparing the aromatic heterocyclic compound represented by general formula I as defined in claim 1, comprising the following steps: coupling compound I-A with compound I-B to obtain the aromatic heterocyclic compound represented by general formula I;

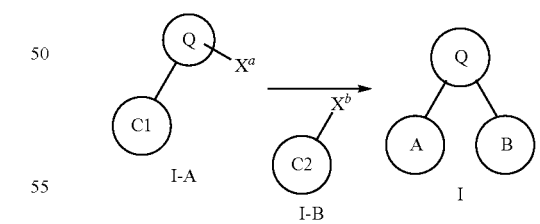

wherein, one of $X^a$ and $X^b$ is H, and the other is halogen;
or, one of $X^a$ and $X^b$ is an organotin reagent or an organoboron reagent, and the other is halogen;
or one of $X^a$ and $X^b$ is —OPG1, and PG1 is p-toluenesulfonyl or methanesulfonyl; and the other is organotin reagent or organoboron reagent;
one of ring C1 and ring C2 is ring A, and the other is ring B; ring A, ring B and ring Q are as defined in claim 1.

10. An intermediate compound for preparing the aromatic heterocyclic compound represented by general formula I as defined in claim 1, which is any of the following compounds:

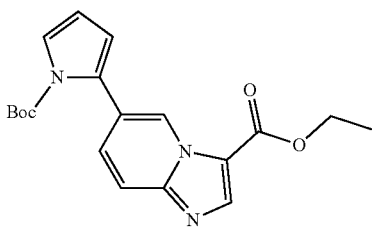
2-b

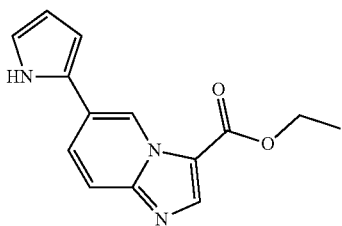
2-a

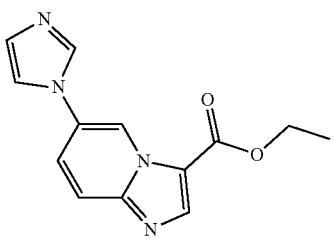
6-a

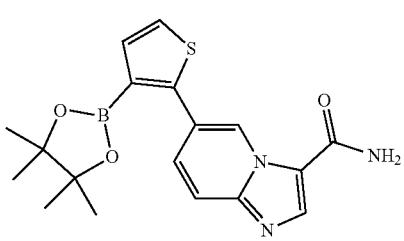
17-a

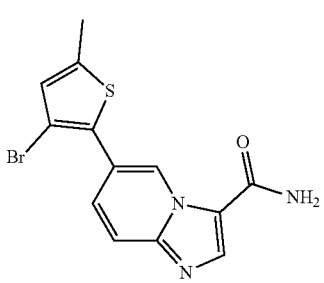
18-b

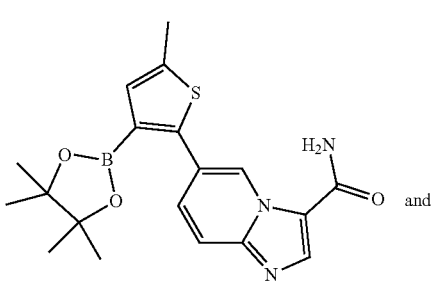
18-a

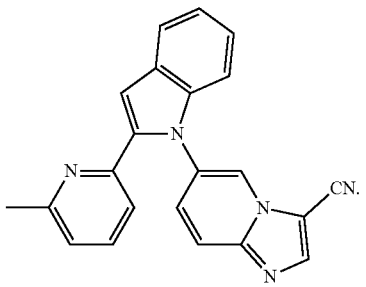
25-a

11. A method for inhibiting ALK5 in a subject in need thereof, comprising: administering an effective amount of the aromatic heterocyclic compound represented by the general formula I or the pharmaceutically acceptable salt thereof as defined in claim 1 to the subject.

12. A pharmaceutical composition comprising one or more of the prophylactically and/or therapeutically effective dose of nitrogen-containing aromatic heterocyclic compound represented by general formula I and the pharmaceutically acceptable salt thereof as defined in claim 1, and a pharmaceutically apreviocceptable carrier.

13. A method for treating ALK5-mediated diseases in a subject in need thereof, comprising: administering an effective amount of the aromatic heterocyclic compound represented by the general formula I or the pharmaceutically acceptable salt thereof as defined in claim 1 to the subject, wherein the ALK5-mediated disease is one or more of colon cancer, pancreatic cancer, breast cancer, prostate cancer, lung cancer, brain cancer, ovarian cancer, cervical cancer, testicular cancer, renal cancer, head or neck cancer, bone cancer, skin cancer, rectal cancer, liver cancer, rectal cancer, esophageal cancer, gastric cancer, pancreatic cancer, thyroid cancer, bladder cancer, lymphoma, leukemia and melanoma.

14. The aromatic heterocyclic compound represented by the general formula I or the pharmaceutically acceptable salt thereof as defined in claim 2, wherein
the halogen is F, Cl, Br or I;
or, the $C_{1-6}$ alkyl in the substituted or unsubstituted $C_{1-6}$ alkyl and the $C_{1-6}$ alkyl are independently methyl, ethyl, n-propyl, isopropyl, n-butyl, isobutyl, or tert-butyl;
or, the $C_{2-8}$ alkenyl in the substituted or unsubstituted $C_{2-8}$ alkenyl and the $C_{2-8}$ alkenyl are independently vinyl, propenyl, allyl,

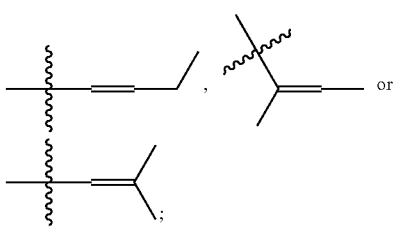

or, the $C_{2-8}$ alkynyl in the substituted or unsubstituted $C_{2-8}$ alkynyl and the $C_{2-8}$ alkynyl are independently ethynyl, propynyl, butynyl or 3-methylpropynyl.

15. The aromatic heterocyclic compound represented by the general formula I or the pharmaceutically acceptable salt thereof as defined in claim 4, wherein in ring A, $R^3$, $R^{31}$, $R^{32}$, and $R^{33}$ are each independently hydrogen, halogen, —$OR^{a5}$, or substituted or unsubstituted $C_{1-6}$ alkyl; wherein, $R^{a5}$ is hydrogen or $C_{1-6}$ alkyl, and substituents in the substituted $C_{1-6}$ alkyl are one or more of the following substituents: deuterium or halogen.

16. The aromatic heterocyclic compound represented by the general formula I or the pharmaceutically acceptable salt thereof as defined in claim 15, wherein in ring A, $R^3$, $R^{31}$, $R^{32}$, and $R^{33}$ are each independently hydrogen, $C_{1-6}$ alkyl or $C_{1-6}$ alkyl substituted with halogen, and the number of the halogen is one or more than one.

\* \* \* \* \*